(12) United States Patent
Kim et al.

(10) Patent No.: US 11,208,462 B2
(45) Date of Patent: Dec. 28, 2021

(54) CILIARY NEUROTROPHIC FACTOR RECEPTOR LIGAND-BINDING AGENTS AND METHODS OF USING THE SAME

(71) Applicant: The Board of Trustees of the Leland Stanford Junior University, Stanford, CA (US)

(72) Inventors: Jun Woo Kim, Mountain View, CA (US); Jennifer R. Cochran, Stanford, CA (US); Eric Alejandro Sweet, San Francisco, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/465,754

(22) PCT Filed: Dec. 6, 2017

(86) PCT No.: PCT/US2017/064883
§ 371 (c)(1),
(2) Date: May 31, 2019

(87) PCT Pub. No.: WO2018/106790
PCT Pub. Date: Jun. 14, 2018

(65) Prior Publication Data
US 2019/0359683 A1  Nov. 28, 2019

Related U.S. Application Data

(60) Provisional application No. 62/481,027, filed on Apr. 3, 2017, provisional application No. 62/430,757, filed on Dec. 6, 2016.

(51) Int. Cl.
*C07K 14/715* (2006.01)
*A61P 35/00* (2006.01)
(Continued)

(52) U.S. Cl.
CPC ............ *C07K 14/715* (2013.01); *A61P 35/00* (2018.01); *C07K 14/52* (2013.01);
(Continued)

(58) Field of Classification Search
CPC .... C07K 14/71; C07K 14/715; C07K 14/475; C07K 14/52; A61P 35/00; A61K 38/00;
(Continued)

(56) References Cited

U.S. PATENT DOCUMENTS

| 5,426,177 A * | 6/1995 | Davis | C07K 14/705 530/395 |
|---|---|---|---|
| 5,648,334 A * | 7/1997 | Davis | C12Q 1/6883 514/8.4 |

(Continued)

OTHER PUBLICATIONS

Wagner et al., The Amino Acid Exchange R28E in Ciliary Neurotrophic Factor (CNTF) Abrogates Interleukin-6 Receptor-dependent but Retains CNTF Receptor-dependent Signaling . . . , Journal of Biological Chemistry 289(26):18442-18450, Jun. 27, 2014. (Year: 2014).*

(Continued)

*Primary Examiner* — Kimberly Ballard
(74) *Attorney, Agent, or Firm* — Brian E. Davy; Bozicevic, Field & Francis LLP

(57) ABSTRACT

Provided are agents that specifically bind a ligand of ciliary neurotrophic factor receptor (CNTFR). In certain aspects, an agent of the present disclosure is a soluble CNTFR polypeptide. The soluble CNTFR polypeptide may have an altered (e.g., reduced) binding affinity for one or more ligand-CNTFR complex subunits, an altered (e.g., increased) binding affinity for one or more CNTFR ligands, or any combination thereof. Compositions that include the agents of the present disclosure are also provided, as are methods of using the agents (e.g., for treating a cell prolif- (Continued)

erative disorder) and methods of identifying an individual as having a cell proliferative disorder associated with CNTFR signaling.

20 Claims, 31 Drawing Sheets

Specification includes a Sequence Listing.

(51) Int. Cl.
  *A61K 38/00* (2006.01)
  *C07K 14/52* (2006.01)
  *C07K 16/28* (2006.01)
  *C12Q 1/6886* (2018.01)
  *G01N 33/574* (2006.01)
(52) U.S. Cl.
  CPC ........ *C07K 16/2866* (2013.01); *C12Q 1/6886* (2013.01); *G01N 33/57492* (2013.01); *A61K 38/00* (2013.01); *C07K 2317/76* (2013.01); *C07K 2317/92* (2013.01); *C07K 2319/30* (2013.01)
(58) Field of Classification Search
  CPC ................ A61K 38/177; A61K 38/179; A61K 38/1793; C12Q 1/6866; G01N 33/57492
  See application file for complete search history.

(56) References Cited

U.S. PATENT DOCUMENTS

| 6,756,357 | B1 * | 6/2004 | Laufer ................. | A61P 25/28 514/8.4 |
| 2008/0254451 | A1 | 10/2008 | Chumakov et al. | |

OTHER PUBLICATIONS

Davis et al. (1993) "Released form of CNTF Receptor alpha Component as a soluble Mediator of CNTF responses" Science, 259(9):1736-1739.
Kim et al. (2019) "Antitumor activity of an engineered decoy receptor targeting CLCF1-CNTFR signaling in lung adenocarcinoma" Nature Medicine, 25(11):1783-1795.
Lelievre et al. (2001) "Signaling pathways recruited by the cardiotrophin-like cytokine/cytokine-like factor-1 composite cytokine: Specific requirement of the membrane-bound form of ciliary neurotrophic factor receptor alpha component" J. of Biol. Chem., 276(25):22476-22484.
Perret et al. (2004) "Two Different Contact Sites Are Recruited by Cardiotrophin-like Cytokine (CLC) to Generate the CLC/CLF and CLC/sCNTFR[alpha] Composite Cytokines" J. of Biol. Chem., 279(42):43961-43970.
Rousseau et al. (2008) "Ciliary Neurotrophic Factor, Cardiotrophin-like Cytokine, and Neuropoietin Share a Conserved Binding Site on the Ciliary Neurotrophic Factor Receptor [alpha] Chain" Journal of Biological Chemistry, 283(44):30341-30350.
Vejby Larsen et al. (2016) "Cytokine-Like Factor 1, an Essential Facilitator of Cardiotrophin-Like Cytokine:Ciliary Neurotrophic Factor Receptor [alpha] Signaling and sorLA-Mediated Turnover" Molecular and Cellular Biology, 36 (8):1272-1286.
Auguste et al. (1996) "Alanine Substitution for Thr268 and Asp269 of Soluble Ciliary Neurotrophic Factor (CNTF) Receptor α Component Defines a Specific Antagonist for the CNTF Response" J. Biol. Chem., 271(42):26049-26056.
Burger et al. (2003) "Functional significance of novel neurotrophin-1/B cell-stimulating factor-3 (cardiotrophin-like cytokine) for human myeloma cell growth and survival" British J. of Haematology, 123:869-878.
Looyenga et al. (2012) "STAT3 Is Activated by JAK2 Independent of Key Oncogenic Driver Mutations in Non-Small Cell Lung Carcinoma" PLoS ONE, 7(2):e30820, 12pgs.
Lu et al. (2012) "CNTF receptor subunit α as a marker for glioma tumor-initiating cells and tumor grade" J. Neurosurg., 117(6):1022-1031.
Márquez et al. (2106) "Targeting Epithelial-Stromal Interactions for Lung Cancer Therapy" Center for Molecular Medicine Cologne, 3pgs., 32nd Ernst Klenk Symposium in Molecular Medicine, Dec. 8-10, Cologne, Germany.
Sweet-Cordero and Cochran (2016) "Upstage Lung Cancer" http://upstageluncancer.org/research/alejandro-sweet-cordero/ 2pgs.
Taga et al. (1992) "Functional inhibition of hematopoietic and neurotrophic cytokines by blocking the interleukin 6 signal transducer gp130" PNAS, 89:10998-11001.
Vicent et al. (2012) "Cross-species functional analysis of cancer-associated fibroblasts identifies a critical role for CLCF1 and IL6 in non-small cell lung cancer in vivo" Cancer Res., 72(22):1-21.
Márquez et al. (2017) "Analysis of Epithelial-Stromal Interactions and their Relevance to Lung Cancer" Journal of Thoracic Oncology 12:1 S828-S829.
Dietel et al. (2016) "Diagnostic procedures for non-small-cell lung cancer (NSCLC): recommendations of the European Expert Group" Thorax, 71:177-184.

* cited by examiner

| Residue no. | 36 | 61 | 88 | 107 | 132 | 140 | 144 | 146 | 163 | 166 | 168 | 169 | 174 | 184 | 189 | 190 | 201 | 220 | 224 | 235 | 237 | 243 | 250 | 255 | 258 | 271 | 283 | 287 | 304 | 308 | 333 |
|---|---|---|---|---|---|---|---|---|---|---|---|---|---|---|---|---|---|---|---|---|---|---|---|---|---|---|---|---|---|---|---|
| WT | E | G | A | L | P | T | T | L | R | Y | M | T | S | H | H | N | I | R | V | P | S | F | I | Q | E | Y | K | I | E | H | K |
| 1 | | | S | | S | | | | | | | | | | | | | | | | | | | | | | | | | | |
| 2 | | | S | | | | | | | | | | | | | | | | | | | | | | | | | | | | |
| 3 | | | | | | | | | S | | | | P | | | | | | | | | | | | | | | | | | |
| 4 | | | | | | | | | S | | | | P | | | | | | | | | | L | | | | | | | | |
| 5 | | | | | | | | | | | | | P | C | | | | | | | | | | | G | | | | | | |
| 6 | | | | | | | | | | | | | P | | R | | | | | | | | L | | | | | | | | |
| 7 | | G | | | | | | | | | T | | | G | | | | | A | | | | V | | G | | | | | | |
| 8 | | | | | | | | | | C | | | | | | | | | S | | F | | | | | M | | | | | |
| 9 | | | | | | | | | | V | | | | | | | | | | | | | | | | | | | | | |
| 10 | V | | | | | L | | Q | | | | | | | | | | | | | | | | | | | | F | | | |
| 11 | | T | | | | | | | | | | | | | | | | | | | | | | | | | | F | | | |
| 12 | | | | | | | | | | | | | | | N | D | V | | | | | | | | | | | | G | | |
| 13 | | | | | | | | | | | | | L | | | | | | | | | | | | | | | | | R | |
| 14 | | | | | | | | | | | | | P | N | R | | | | | | | | | | | | | | | | R |
| 15 | | | | | | | | | | | | | P | | | | | | | | | | | | | | | | G | | |
| 16 | | | | | | | | | | | | | P | | | | | | | | | | V | | G | | | | | | |
| 17 | | | | | | | S | | | | | | P | | | | | | | | | | | | | | | F | | | |
| 18 | | | | | | | | | | | | | P | | | | | | | | | | | | | | | | G | | |

FIG. 8

| | RESIDUE NO. | | | | | | | | | | | | | | | | | | | | |
|---|---|---|---|---|---|---|---|---|---|---|---|---|---|---|---|---|---|---|---|---|---|
| | 59 | 63 | 69 | 75 | 94 | 110 | 156 | 167 | 191 | 228 | 235 | 237 | 243 | 266 | 287 | 289 | 304 | 311 | 317 | 323 | 333 |
| WT | V | D | L | V | S | R | K | R | A | T | P | S | F | T | T | I | E | T | E | T | K |
| 1 | | | | | | | | | E | | | F | | | | | | | | | |
| 2 | | | F | | N | Q | | | | | | F | | | | | | | | | |
| 3 | | | | A | | | | | | | | F | | | | | | | | | |
| 4 | | | | | | | | | | | | Y | | | | | | | | | |
| 5 | | | | | | | | | | | | F | | | | | | | | | |
| 6 | | | | | | | | | | | | F | | | | | | | | | |
| 7 | | N | F | | N | Q | | | A | | | F | | | A | | | | | | |
| 8 | | | | | | | | | | | | F | | | | | | | | | |
| 9 | | | | | | | | | | | | F | | | | | | | | | |
| 10 | L | | F | | | | | | | | | F | | | | | | | | | |
| 11 | | | | | | | | | | | | F | L | | | | | | | | |
| 12 | | | | | | | | | | | | F | | A | | | | | | | |
| 13 | | | | | | | | | | | | F | | | | | | | | | |
| 14 | | | | | | | | H | | | | F | | | | | A | G | | | M |
| 15 | | | | | | | | | | | S | F | | | F | | | A | G | | |
| 16 | | | | | | | | H | | | S | F | | | F | | | | | | |
| 17 | | | | | | | | | | | | F | | | | | | | | | |
| 18 | | | | | | | E | | | | | F | | | | | | | G | A | |

FIG. 9

| Residue no. | 40 | 63 | 69 | 70 | 75 | 77 | 88 | 94 | 107 | 110 | 126 | 140 | 144 | 146 | 156 | 163 | 166 | 167 | 169 | 174 | 177 | 184 | 189 | 190 | 201 | 220 | 228 | 235 | 237 | 243 | 245 | 250 | 255 | 258 | 271 | 283 | 287 | 300 | 306 | 311 | 316 | 317 | 323 | 331 | 333 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| WT | V | D | L | N | V | H | A | S | L | R | Y | T | T | L | K | R | M | T | Y | S | H | N | R | T | P | S | F | R | L | Q | E | Y | K | I | T | P | T | E | E | T | T | K |
| 1 | | | | | | | | | | | | | | | | | | | | | | | | | | | F | H | | | | | | | | | | | | | A | | | | |
| 2 | | | | | | | | | | | F | | | | S | | | | | | | | | | | | | | | | | | | | | | | | | | | | | | |
| 3 | | | | | | | | | | | | S | Q | | | | | | | | | | | | | | | | | | | | | | | F | M | | | | | | | | |
| 4 | | | | | | | | | | | | | | | | | | | | | H | | | A | | | | F | | | | | | | | | F | | | | | | | | |
| 5 | | | | | | | | | | | | | | | | | | | | | | | | | | | | F | L | | | | | | | | F | | | | | | | | |
| 6 | | N | | | | | A | Q | | | | | | | | | | | R | | | | | | | | | | F | | | | | | | | F | | | | | | | | |
| 7 | | | | | | | | | Q | | | | | | | | | | | | | N | D | V | | | | F | | | | | | | | | F | | | | | | | | |
| 8 | | | | | | | R | | | | | | | | | | | | | | | | | | | | | F | | | | | | | | | M | | A | | | | | | |
| 9 | | | | | | | | | Q | | | | | | | | | | | | H | | | | | | | F | | | | | | | | | F | | | | | | | | |
| 10 | | | | | | K | | | | | | | | | | | | T | | | | | | | | | | F | | | | | V | | | | F | | | | | G | | | |
| 11 | | | | | | | | | | | | | | | | | | | P | | C | | | | | | | F | | | G | | | | | | F | | | | | | | | |
| 12 | | | | | | | | | | | | | | | | | | | | | | | | | | | | F | | | | | | | | | F | | | | | | R | | |
| 13 | | | | | | | | | Q | | | | | | S | V | | | | | | | | | | | | F | | | | | | | | | F | | | | | | | | |
| 14 | | | | | | | | | | | | | | | | | | | | | | | | | | S | | F | | | | | | | | | F | | | | | | | | |
| 15 | L | F | | | | | | | | | | | | | | | | T | | | | | | | | | | F | | | | | | | | | F | | | | | | | | |
| 16 | L | | T | T | | | | | | | | | | | | | | | | | | | | A | | | | F | | | | | | | | | F | | | | A | | | | |
| 17 | | | | | | | | | Q | | | | | | S | V | | | | | | | | | | | | F | | | | | | | | | F | | G | | | | | | |
| 18 | | | | | | | | | | | | | | | | | | | | | | | | | | | | F | L | | | | | | | | F | | | | | | | | |
| 19 | | | | | | | | | | | | | | | | | H | | | | | | | | | | | F | | | | | | | | | F | | | | | G | | | R |
| 20 | | | | | | | | | | | | | | | E | | | | | R | | | | | | | | F | L | | R | | | | | | C | M | | | | | | | |
| 21 | | | | | | | | | | | | | | | | | | | | | | | | | | S | | F | | | | | | | | | F | | | | | | | | |
| 22 | | | | | | | | | | | | | | | | | | T | | | R | | | | | | | F | | | | | | | | | F | L | | | | | | | |

| | RESIDUE NO. | | | | Kd (nM) |
|---|---|---|---|---|---|
| | 110 | 174 | 237 | 287 | |
| WT | R | T | S | I | -- |
| VARIANT 1 | | | F | | 4100 ± 400 |
| VARIANT 2 | | P | F | | 890 ± 20 |
| VARIANT 3 | | P | F | F | 49 ± 6 |
| VARIANT 4 | Q | P | F | F | 19 ± 3 |
| VARIANT 5 | | | F | F | 740 ± 70 |

SEQUENCE LISTING

```
<160> NUMBER OF SEQ ID NOS: 4

<210> SEQ ID NO 1
<211> LENGTH: 372
<212> TYPE: PRT
<213> ORGANISM: Homo sapiens

<400> SEQUENCE: 1

Met Ala Ala Pro Val Pro Trp Ala Cys Cys Ala Val Leu Ala Ala Ala
1               5                   10                  15

Ala Ala Val Val Tyr Ala Gln Arg His Ser Pro Gln Glu Ala Pro His
                20                  25                  30

Val Gln Tyr Glu Arg Leu Gly Ser Asp Val Thr Leu Pro Cys Gly Thr
            35                  40                  45

Ala Asn Trp Asp Ala Ala Val Thr Trp Arg Val Asn Gly Thr Asp Leu
        50                  55                  60

Ala Pro Asp Leu Leu Asn Gly Ser Gln Leu Val Leu His Gly Leu Glu
65                  70                  75                  80

Leu Gly His Ser Gly Leu Tyr Ala Cys Phe His Arg Asp Ser Trp His
                85                  90                  95

Leu Arg His Gln Val Leu Leu His Val Gly Leu Pro Pro Arg Glu Pro
                100                 105                 110

Val Leu Ser Cys Arg Ser Asn Thr Tyr Pro Lys Gly Phe Tyr Cys Ser
            115                 120                 125

Trp His Leu Pro Thr Pro Thr Tyr Ile Pro Asn Thr Phe Asn Val Thr
        130                 135                 140

Val Leu His Gly Ser Lys Ile Met Val Cys Glu Lys Asp Pro Ala Leu
145                 150                 155                 160

Lys Asn Arg Cys His Ile Arg Tyr Met His Leu Phe Ser Thr Ile Lys
                165                 170                 175

Tyr Lys Val Ser Ile Ser Val Ser Asn Ala Leu Gly His Asn Ala Thr
                180                 185                 190

Ala Ile Thr Phe Asp Glu Phe Thr Ile Val Lys Pro Asp Pro Pro Glu
            195                 200                 205
```

```
Asn Val Val Ala Arg Pro Val Pro Ser Asn Pro Arg Arg Leu Glu Val
    210                 215                 220

Thr Trp Gln Thr Pro Ser Thr Trp Pro Asp Pro Glu Ser Phe Pro Leu
225                 230                 235                 240

Lys Phe Phe Leu Arg Tyr Arg Pro Leu Ile Leu Asp Gln Trp Gln His
                245                 250                 255

Val Glu Leu Ser Asp Gly Thr Ala His Thr Ile Thr Asp Ala Tyr Ala
                260                 265                 270

Gly Lys Glu Tyr Ile Ile Gln Val Ala Ala Lys Asp Asn Glu Ile Gly
            275                 280                 285

Thr Trp Ser Asp Trp Ser Val Ala Ala His Ala Thr Pro Trp Thr Glu
290                 295                 300

Glu Pro Arg His Leu Thr Thr Glu Ala Gln Ala Ala Glu Thr Thr Thr
305                 310                 315                 320

Ser Thr Thr Ser Ser Leu Ala Pro Pro Thr Thr Lys Ile Cys Asp
                325                 330                 335

Pro Gly Glu Leu Gly Ser Gly Gly Pro Ser Ala Pro Phe Leu Val
            340                 345                 350

Ser Val Pro Ile Thr Leu Ala Leu Ala Ala Ala Ala Thr Ala Ser
                355                 360                 365

Ser Leu Leu Ile
    370

<210> SEQ ID NO 2
<211> LENGTH: 342
<212> TYPE: PRT
<213> ORGANISM: Artificial Sequence
<220> FEATURE:
<223> OTHER INFORMATION: Synthetic Sequence

<400> SEQUENCE: 2

Met Ala Ala Pro Val Pro Trp Ala Cys Cys Ala Val Leu Ala Ala Ala
1               5                   10                  15

Ala Ala Val Val Tyr Ala Gln Arg His Ser Pro Gln Glu Ala Pro His
            20                  25                  30

Val Gln Tyr Glu Arg Leu Gly Ser Asp Val Thr Leu Pro Cys Gly Thr
        35                  40                  45

Ala Asn Trp Asp Ala Ala Val Thr Trp Arg Val Asn Gly Thr Asp Leu
50                  55                  60

Ala Pro Asp Leu Leu Asn Gly Ser Gln Leu Val Leu His Gly Leu Glu
65                  70                  75                  80

Leu Gly His Ser Gly Leu Tyr Ala Cys Phe His Arg Asp Ser Trp His
                85                  90                  95

Leu Arg His Gln Val Leu Leu His Val Gly Leu Pro Pro Gln Glu Pro
            100                 105                 110

Val Leu Ser Cys Arg Ser Asn Thr Tyr Pro Lys Gly Phe Tyr Cys Ser
        115                 120                 125

Trp His Leu Pro Thr Pro Thr Tyr Ile Pro Asn Thr Phe Asn Val Thr
130                 135                 140

Val Leu His Gly Ser Lys Ile Met Val Cys Glu Lys Asp Pro Ala Leu
145                 150                 155                 160

Lys Asn Arg Cys His Ile Arg Tyr Met His Leu Phe Ser Pro Ile Lys
                165                 170                 175

His Asn Val Ser Ile Ser Val Ser Asn Ala Leu Gly His Asn Ala Thr
            180                 185                 190
```

```
Ala Ile Thr Phe Asp Glu Phe Thr Ile Val Lys Pro Asp Pro Pro Glu
        195                 200                 205

Asn Val Val Ala Arg Pro Val Pro Ser Asn Pro Arg Arg Leu Glu Val
    210                 215                 220

Thr Trp Gln Thr Pro Ser Thr Trp Pro Asp Pro Glu Phe Phe Pro Leu
225                 230                 235                 240

Lys Phe Phe Leu Arg Tyr Arg Pro Leu Ile Leu Asp Gln Trp Gln His
                245                 250                 255

Val Glu Leu Ser Asp Gly Thr Ala His Thr Ile Ala Ala Ala Tyr Ala
                260                 265                 270

Gly Lys Glu Tyr Ile Ile Gln Val Ala Ala Lys Asp Asn Glu Phe Gly
        275                 280                 285

Thr Trp Ser Asp Trp Ser Val Ala Ala His Ala Thr Pro Trp Thr Glu
        290                 295                 300

Glu Pro Arg His Leu Thr Thr Glu Ala Gln Ala Ala Glu Thr Thr Thr
305                 310                 315                 320

Ser Thr Thr Ser Ser Leu Ala Pro Pro Thr Thr Lys Ile Cys Asp
                325                 330                 335

Pro Gly Glu Leu Gly Ser
            340

<210> SEQ ID NO 3
<211> LENGTH: 227
<212> TYPE: PRT
<213> ORGANISM: Homo sapiens

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205
```

His Glu Ala Leu His Asn His Tyr Thr Gln Lys Ser Leu Ser Leu Ser
210                 215                 220

Pro Gly Lys
225

<210> SEQ ID NO 4
<211> LENGTH: 578
<212> TYPE: PRT
<213> ORGANISM: Artificial Sequence
<220> FEATURE:
<223> OTHER INFORMATION: Synthetic Sequence

<400> SEQUENCE: 4

Met Ala Ala Pro Val Pro Trp Ala Cys Cys Ala Val Leu Ala Ala Ala
1               5                   10                  15

Ala Ala Val Val Tyr Ala Gln Arg His Ser Pro Gln Glu Ala Pro His
            20                  25                  30

Val Gln Tyr Glu Arg Leu Gly Ser Asp Val Thr Leu Pro Cys Gly Thr
        35                  40                  45

Ala Asn Trp Asp Ala Ala Val Thr Trp Arg Val Asn Gly Thr Asp Leu
    50                  55                  60

Ala Pro Asp Leu Leu Asn Gly Ser Gln Leu Val Leu His Gly Leu Glu
65                  70                  75                  80

Leu Gly His Ser Gly Leu Tyr Ala Cys Phe His Arg Asp Ser Trp His
                85                  90                  95

Leu Arg His Gln Val Leu Leu His Val Gly Leu Pro Pro Gln Glu Pro
            100                 105                 110

Val Leu Ser Cys Arg Ser Asn Thr Tyr Pro Lys Gly Phe Tyr Cys Ser
        115                 120                 125

Trp His Leu Pro Thr Pro Thr Tyr Ile Pro Asn Thr Phe Asn Val Thr
130                 135                 140

Val Leu His Gly Ser Lys Ile Met Val Cys Glu Lys Asp Pro Ala Leu
145                 150                 155                 160

Lys Asn Arg Cys His Ile Arg Tyr Met His Leu Phe Ser Pro Ile Lys
                165                 170                 175

His Asn Val Ser Ile Ser Val Ser Asn Ala Leu Gly His Asn Ala Thr
            180                 185                 190

Ala Ile Thr Phe Asp Glu Phe Thr Ile Val Lys Pro Asp Pro Pro Glu
        195                 200                 205

Asn Val Val Ala Arg Pro Val Pro Ser Asn Pro Arg Arg Leu Glu Val
    210                 215                 220

Thr Trp Gln Thr Pro Ser Thr Trp Pro Asp Pro Glu Phe Phe Pro Leu
225                 230                 235                 240

Lys Phe Phe Leu Arg Tyr Arg Pro Leu Ile Leu Asp Gln Trp Gln His
                245                 250                 255

Val Glu Leu Ser Asp Gly Thr Ala His Thr Ile Ala Ala Ala Tyr Ala
            260                 265                 270

Gly Lys Glu Tyr Ile Ile Gln Val Ala Ala Lys Asp Asn Glu Phe Gly
        275                 280                 285

Thr Trp Ser Asp Trp Ser Val Ala Ala His Ala Thr Pro Trp Thr Glu
    290                 295                 300

Glu Pro Arg His Leu Thr Thr Glu Ala Gln Ala Ala Glu Thr Thr Thr
305                 310                 315                 320

Ser Thr Thr Ser Ser Leu Ala Pro Pro Pro Thr Thr Lys Ile Cys Asp
                325                 330                 335

```
Pro Gly Glu Leu Gly Ser Arg Arg Leu Glu Pro Arg Gly Pro Thr Ile
            340                 345                 350

Lys Pro Cys Pro Pro Cys Lys Cys Pro Ala Pro Asn Leu Leu Gly Gly
        355                 360                 365

Pro Ser Val Phe Ile Phe Pro Pro Lys Ile Lys Asp Val Leu Met Ile
    370                 375                 380

Ser Leu Ser Pro Ile Val Thr Cys Val Val Val Asp Val Ser Glu Asp
385                 390                 395                 400

Asp Pro Asp Val Gln Ile Ser Trp Phe Val Asn Asn Val Glu Val His
                405                 410                 415

Thr Ala Gln Thr Gln Thr His Arg Glu Asp Tyr Asn Ser Thr Leu Arg
            420                 425                 430

Val Val Ser Ala Leu Pro Ile Gln His Gln Asp Trp Met Ser Gly Lys
        435                 440                 445

Glu Phe Lys Cys Lys Val Asn Asn Lys Asp Leu Pro Ala Pro Ile Glu
    450                 455                 460

Arg Thr Ile Ser Lys Pro Lys Gly Ser Val Arg Ala Pro Gln Val Tyr
465                 470                 475                 480

Val Leu Pro Pro Pro Glu Glu Glu Met Thr Lys Lys Gln Val Thr Leu
            485                 490                 495

Thr Cys Met Val Thr Asp Phe Met Pro Glu Asp Ile Tyr Val Glu Trp
                500                 505                 510

Thr Asn Asn Gly Lys Thr Glu Leu Asn Tyr Lys Asn Thr Glu Pro Val
            515                 520                 525

Leu Asp Ser Asp Gly Ser Tyr Phe Met Tyr Ser Lys Leu Arg Val Glu
    530                 535                 540

Lys Lys Asn Trp Val Glu Arg Asn Ser Tyr Ser Cys Ser Val Val His
545                 550                 555                 560

Glu Gly Leu His Asn His His Thr Thr Lys Ser Phe Ser Arg Thr Pro
                565                 570                 575

Gly Lys
```

CILIARY NEUROTROPHIC FACTOR RECEPTOR LIGAND-BINDING AGENTS AND METHODS OF USING THE SAME

CROSS REFERENCE TO RELATED APPLICATIONS

This application claims the benefit of U.S. Provisional Patent Application No. 62/430,757, filed Dec. 6, 2016, and U.S. Provisional Patent Application No. 62/481,027, filed Apr. 3, 2017, which applications are incorporated herein by reference in their entirety.

INTRODUCTION

Ciliary neurotrophic factor (CNTF) was identified as a survival factor for chick ciliary neurons and belongs to the interleukin (IL)-6 family of structurally related hemato- and neuropoietic cytokines (IL-6, IL-11, cardiotrophin-like cytokine factor 1 (CLCF1), leukemia inhibitory factor (LIF), oncostatin M (OSM), cardiotrophin-1 (CT-1)). Cellular responses to CNTF and IL-6 type cytokines are elicited by different multi-unit receptor complexes that include the membrane-spanning 130-kDa glycoprotein, gp130. CNTF first binds in a 1:1 stoichiometry to the GPI-anchored CNTF receptor (CNTFR), which is not involved in signal transduction. Binding of CNTF to the membrane-bound or soluble CNTFR induces a heterodimer of the signal transducing n-receptors gp130 and LIF receptor (LIFR), which triggers intracellular signaling cascades.

Cancer is initiated and progresses within a microenvironment that is itself altered as a consequence of the tumorigenic process. Stromal cells in contact with cancer cells secrete growth factors and cytokines that may act directly by signaling to tumor cells or indirectly by recruiting other stromal components to promote tumor progression. An important aspect of this process is the expansion of cancer-associated fibroblasts (CAFs). CAFs are a diverse population of stromal cells with distinct characteristics in different tumors and tissues.

CAFs support the growth of cancer cells (e.g., lung cancer cells) in vivo by secretion of soluble factors that stimulate the growth of tumor cells. One such soluble factor is cardiotrophin-like cytokine factor 1 (CLCF1). CLCF1 produced by cells in the stroma is received as a growth signal by tumor cells expressing a receptor for this protein—CNTFR. For example, functional studies have identified a role for CLCF1-CNTFR signaling in promoting growth of non-small cell lung cancer (NSCLC).

SUMMARY

Provided are agents that specifically bind a ligand of ciliary neurotrophic factor receptor (CNTFR). In certain aspects, an agent of the present disclosure is a soluble CNTFR polypeptide. The soluble CNTFR polypeptide may have an altered (e.g., reduced) binding affinity for one or more ligand-CNTFR complex subunits, an altered (e.g., increased) binding affinity for one or more CNTFR ligands, or any combination thereof. Compositions that include the agents of the present disclosure are also provided, as are methods of using the agents (e.g., for treating a cell proliferative disorder) and methods of identifying an individual as having a cell proliferative disorder associated with CNTFR signaling.

BRIEF DESCRIPTION OF THE FIGURES

FIG. 7 shows variants isolated from the intermediate affinity population after 3 rounds of sorting of the randomly mutagenized CNTFR library against CLCF1.

FIG. 8 shows variants isolated from the highest affinity population after 3 rounds of sorting of the randomly mutagenized CNTFR library against CLCF1.

FIG. 9 shows variants isolated from the highest affinity population after 3 rounds of sorting of the shuffled CNTFR library against CLCF1.

Figure 1:
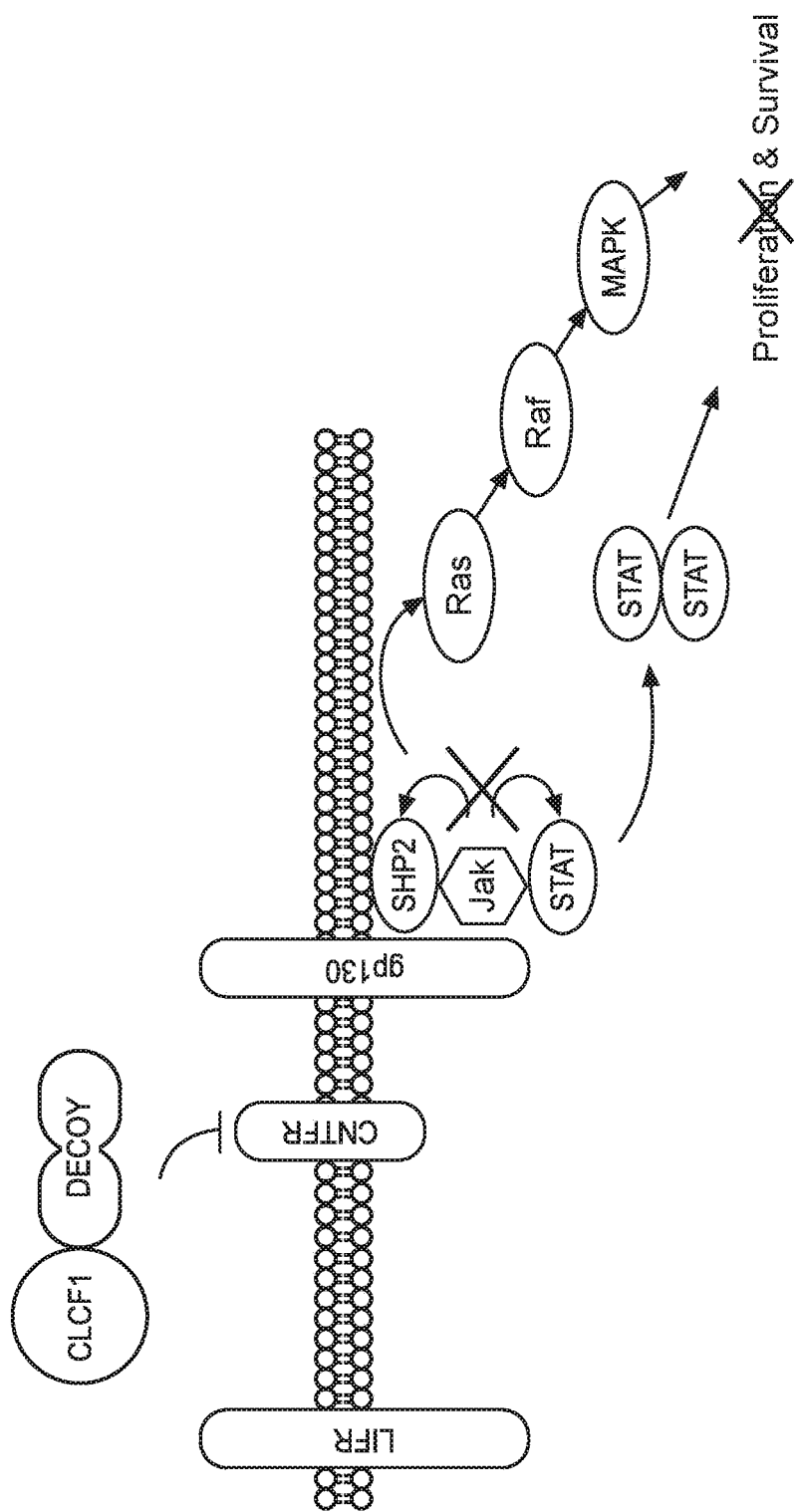
FIG. 1 schematically illustrates a strategy to inhibit downstream CNTFR signaling pathways according to one embodiment of the present disclosure. In this embodiment, the agent that specifically binds a ligand of CNTFR is a soluble CNTFR "decoy receptor" that inhibits CLCF1 from interacting with membrane bound CNTFR, preventing activation of CLCF1-CNTFR mediated signaling pathways such as the JAK STAT pathway and the MAPK/ERK pathway.

Unless defined otherwise, all technical and scientific terms used herein have the same meaning as commonly understood by one of ordinary skill in the art to which the agents, compositions and methods belong. Although any agents, compositions and methods similar or equivalent to those described herein can also be used in the practice or testing of the agents, compositions and methods, representative illustrative agents, compositions and methods are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present agents, compositions and methods are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the agents, compositions and methods, which are, for clarity, described in the context of separate embodiments, may also be provided in combination in a single embodiment. Conversely, various features of the agents, compositions and methods, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present agents, compositions and methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

CNTFR Ligand-Binding Agents

As summarized above, aspects of the present disclosure include agents that specifically bind a ligand of ciliary neurotrophic factor receptor (CNTFR). CNTFR (also referred to as CNTF receptor subunit a) is a member of the type 1 cytokine receptor family. CNTFR is the ligand-specific component of a tripartite receptor for ciliary neurotrophic factor (CNTF), as well as other ligands such as cardiotrophin-like cytokine factor 1 (CLCF1) and neuropoetin (NP). Binding of ligand to CNTFR recruits the transmembrane components of the receptor, gp130 and leukemia inhibitory factor receptor (LIFR), facilitating signal transduction.

As used herein, an "agent that specifically binds a ligand of ciliary neurotrophic factor receptor (CNTFR)" is an agent that exhibits a binding affinity to one or more CNTFR ligands (e.g., one or more of CLCF1, CNTFR, and/or NP) with a $K_D$ of less than or equal to about $10^{-5}$ M, less than or equal to about $10^{-6}$ M, less than or equal to about $10^{-7}$ M, less than or equal to about $10^{-8}$ M, or less than or equal to about $10-9$ M, $10^{-10}$ M, $10^{-11}$ M, or $10^{-12}$ M or less. Such affinities may be readily determined using conventional techniques, such as by equilibrium dialysis; by using surface plasmon resonance (SPR) technology (e.g., the BIAcore 2000 instrument, using general procedures outlined by the manufacturer); by radioimmunoassay; or by another method set forth in the examples below or known to the skilled artisan.

The agents of the present disclosure may be any suitable type of agent that specifically binds a CNTFR ligand, including but not limited to, aptamers, antibodies, and the like. In certain aspects, the agent is a soluble CNTFR polypeptide.

Non-limiting embodiments of CNTFR ligand-binding agents of the present disclosure will now be described in detail.

Soluble CNTFR Polypeptides

As summarized above, in certain aspects, the agent that specifically binds a ligand of CNTFR is a soluble CNTFR polypeptide. By "soluble CNTFR polypeptide" is meant a CNTFR polypeptide that is not integrated into a cell membrane. The wild-type human CNTFR amino acid sequence (UniProtKB—P26992) is provided in Table 1 below.

TABLE 1

| Wild-Type Human CNTFR Amino Acid Sequence (Non-Soluble) |  |
|---|---|
|  | Amino Acid Sequence |
| Wild-Type Human CNTFR (non-soluble) (SEQ ID NO: 1) | MAAPVPWACCAVLAAAAAVVYAQRHSPQEAPHVQYERLGSDVTLPCGTA NWDAAVTWRVNGTDLAPDLLNGSQLVLHGLELGHSGLYACFHRDSWHLR HQVLLHVGLPPREPVLSCRSNTYPKGFYCSWHLPTPTYIPNTFNVTVLH GSKIMVCEKDPALKNRCHIRYMHLFSTIKYKVSISVSNALGHNATAITF DEFTIVKPDPPENVVARPVPSNPRRLEVTWQTPSTWPDPESFPLKFFLR YRPLILDQWQHVELSDGTAHTITDAYAGKEYIIQVAAKDNEIGTWSDWS VAAHATPWTEEPRHLTTEAQAAETTTSTTSSLAPPPTTKICDPGELGS<u>G</u> <u>GGPSAPFLVSVPITLALAAAAATASSLLI</u> |

According to certain embodiments, the soluble CNTFR polypeptide is not integrated into a cell membrane by virtue of the polypeptide having one or more solubility-conferring mutations. As used throughout the present disclosure, a "mutation" or "mutations" may include one or more amino acid substitutions, one or more amino acid deletions (e.g., truncations), one or more amino acid insertions, or any combination thereof, in the relevant polypeptide, e.g., a CNTFR polypeptide of the present disclosure.

The one or more solubility-conferring mutations may be located in any suitable region(s) of the CNTFR polypeptide. In certain aspects, the soluble CNTFR polypeptide includes one or more solubility-conferring mutations in the domain that anchors wild-type CNTFR to the cell membrane. This domain contains a lipidation site (S342) that is post-translationally modified with glycosylphosphatidylinositol (GPI), which anchors the protein to the cell membrane. The wild-type human CNTFR domain that anchors CNTFR to the cell membrane can be defined as consisting of amino acids 343-372 as set forth in SEQ ID NO:1 (underlined in Table 1). Under certain conditions, this portion of CNTFR is enzymatically modified to release CNTFR from the cell membrane. According to some embodiments, a soluble CNTFR polypeptide of the present disclosure includes a substitution mutation at S342 that precludes post-translational modification with GPI, thereby conferring solubility. Wild-type human CNTFR also includes a signal peptide consisting of amino acids 1-22 of SEQ ID NO:1 (underlined in Table 1).

According to certain embodiments, the CNTFR domain that anchors CNTFR to the cell membrane includes one or more amino acid substitutions that result in the CNTFR polypeptide losing its ability to be anchored to a cell membrane, thereby conferring solubility. Alternatively, or additionally, the soluble CNTFR polypeptide may include a truncation (e.g., in the CNTFR domain that anchors CNTFR to the cell membrane) that results in the CNTFR polypeptide losing its ability to be anchored to a cell membrane, thereby conferring solubility. In certain aspects, the soluble CNTFR polypeptide lacks the CNTFR domain that anchors CNTFR to the cell membrane. For example, the soluble CNTFR polypeptide may lack amino acids 343-372 set forth in SEQ ID NO:1.

In addition to optionally including one or more solubility-conferring mutations, a soluble CNTFR polypeptide of the present disclosure may include one or more mutations that confer one or more other desirable properties upon the polypeptide. Other desirable properties of interest include, but are not limited to, altered (e.g., greater) binding affinity for a CNTFR ligand, altered (e.g., greater) specificity for a particular CNTFR ligand of interest as compared to one or more other CNTFR ligands, altered (e.g., reduced) binding affinity for a ligand-CNTFR complex subunit (e.g., gp130, LIFR, and/or the like), relative to a wild-type CNTF receptor, e.g., a receptor having the amino acid sequence set forth in SEQ ID NO:1 or a mature form thereof.

By "greater binding affinity" or "increased binding affinity" is meant that the soluble CNTFR polypeptide exhibits tighter binding (as indicated by a lower $K_D$ value) to a molecule (e.g., a CNTFR ligand such as CLCF1) as compared to a wild-type CNTF receptor. By "lower binding affinity" or "reduced binding affinity" is meant that the soluble CNTFR polypeptide exhibits less tight binding (as indicated by a higher $K_D$ value) to a molecule (e.g., a ligand-CNTFR complex subunit such as LIFR, gp130, or both) as compared to a wild-type CNTF receptor.

Methods are available for measuring the binding affinity of a CNTFR ligand-binding agent (e.g., a soluble CNTFR polypeptide) to a molecule of interest, e.g., a CNTFR ligand, a ligand-CNTFR complex subunit such as LIFR, gp130, or the like. For example, surface plasmon resonance (SPR) technology (e.g., using a BIAcore™ 2000 instrument), KinExA® kinetic exclusion assay (Sapidyne Instruments), Bio-Layer Interferometry (BLI) technology (e.g., ForteBio Octet®), or other similar assay/technology may be employed to determine whether a CNTFR ligand-binding agent exhibits a desired binding affinity. Suitable approaches for measuring binding affinity in the context of the present disclosure include, e.g., those described in Hunter, S. A. and Cochran, J. R. (2016) *Methods Enzymol.* 580:21-44.

In some embodiments, in a direct binding assay, an equilibrium binding constant ($K_D$) may be measured using a CNTFR polypeptide conjugated to a fluorophore or radio-isotope, or a CNTFR polypeptide that contains an N- or C-terminal epitope tag for detection by a labeled antibody. If labels or tags are not feasible or desired, a competition binding assay can be used to determine the half-maximal inhibitory concentration ($IC_{50}$), the amount of unlabeled CNTFR polypeptide at which 50% of the maximal signal of the labeled competitor is detectable. A $K_D$ value can then be calculated from the measured $IC_{50}$ value.

As summarized above, in certain aspects, a soluble CNTFR polypeptide of the present disclosure includes one or more mutations that alters (e.g., reduces) the binding affinity of the soluble CNTFR polypeptide for a ligand-CNTFR complex subunit relative to a wild-type CNTF receptor, e.g., a receptor having the amino acid sequence set forth in SEQ ID NO:1 or a mature form thereof. By "ligand-CNTFR complex subunit" is meant a protein that associates with wild-type CNTFR upon binding of CNTFR to ligand. Non-limiting examples of ligand-CNTFR complex subunits include leukemia inhibitory factor receptor (LIFR) and glycoprotein 130 (gp130). In certain aspects, the one or more mutations reduces the binding affinity of the soluble CNTFR polypeptide for LIFR, gp130, or both. Such one or more mutations may prevent the soluble CNTFR polypeptide from acting as an agonist upon binding to ligand, e.g., when it is desirable to reduce CNTFR-mediated signaling (e.g., to reduce cell proliferation).

According to certain embodiments, when the soluble CNTFR polypeptide exhibits reduced binding affinity for a ligand-CNTFR complex subunit, the binding affinity of the soluble CNTFR polypeptide has a $K_D$ value that is 100 nM or greater in the presence of 10 nM of CLCF1.

In certain aspects, a soluble CNTFR polypeptide of the present disclosure has reduced binding affinity for LIFR and includes a mutation (e.g., an amino acid substitution) at amino acid position 177, 178, or both, relative to a CNTFR polypeptide having the amino acid sequence set forth in SEQ ID NO:1. An example mutation at position 177 is Y177H. Another example mutation at position 177 is Y177A. An example mutation at position 178 is K178N. Another example mutation at position 178 is K178A. As demonstrated in the Examples section below, the present inventors have determined that such mutations result in the soluble CNTFR polypeptide being an inhibitor of CNTFR signaling, whereas a soluble CNTFR polypeptide having unaltered affinity for ligand-CNTFR complex subunits acts as an agonist by virtue of its ability to recruit, e.g., LIFR and gp130 upon binding ligand. In certain aspects, a soluble CNTFR polypeptide of the present disclosure includes the mutations Y177H and K178N, or the mutations Y177A and K178A, or the mutations Y177H and K178A, or the mutations Y177A and K178N.

According to certain embodiments, a soluble CNTFR polypeptide of the present disclosure has reduced binding affinity for gp130 and includes a mutation (e.g., an amino acid substitution) at amino acid position 268, 269, or both, relative to a CNTFR polypeptide having the amino acid sequence set forth in SEQ ID NO:1. An example mutation at position 268 is T268A. An example mutation at position 269 is D269A. In certain aspects, a soluble CNTFR polypeptide of the present disclosure includes the mutations T268A and D269A.

As summarized above, a soluble CNTFR polypeptide of the present disclosure may include one or more mutations that alters (e.g., increases) the binding affinity and/or specificity of the soluble CNTFR polypeptide for a CNTFR ligand of interest (e.g., CLCF1, NP, CNTF, or another CNTFR ligand of interest) relative to a wild-type CNTF receptor, e.g., a receptor having the amino acid sequence set forth in SEQ ID NO:1 or a mature form thereof. According to certain embodiments, when the soluble CNTFR polypeptide exhibits increased binding affinity for a CNTFR ligand, the binding affinity of the soluble CNTFR polypeptide for the ligand has a $K_D$ value that is 10 nM or less.

According to certain embodiments, a soluble CNTFR polypeptide of the present disclosure includes one or more mutations that increases binding affinity and/or specificity for CLCF1. In certain aspects, such a soluble CNTFR polypeptide includes a mutation (e.g., an amino acid substitution) at amino acid position 110, 174, 237, 287, or any combination thereof, relative to a CNTFR polypeptide having the amino acid sequence set forth in SEQ ID NO:1. An example mutation at position 110 is R110Q. An example mutation at position 174 is T174P. An example mutation at position 237 is S237F. Another example mutation at position 237 is S237Y. An example mutation at position 287 is I287F. In certain aspects, a soluble CNTFR polypeptide of the present disclosure includes one or any combination (e.g., each) of the mutations R110Q, T174P, S237F/S237Y, and I287F.

In some embodiments, a soluble CNTFR polypeptide of the present disclosure includes a mutation (e.g., an amino acid substitution) at amino acid position 110, 174, 177, 178, 237, 268, 269, 287, or any combination thereof, relative to a CNTFR polypeptide having the amino acid sequence set forth in SEQ ID NO:1.

In certain aspects, a soluble CNTFR polypeptide of the present disclosure includes one or any combination (e.g., each) of the mutations R110Q, T174P, Y177H/Y177A, K178N/K178A, S237F/S237Y, T268A, D269A, and I287F.

A soluble CNTFR polypeptide according to one embodiment of the present disclosure includes the amino acid sequence set forth in Table 2 below (SEQ ID NO:2). In Table 2, mutations are bold/underlined. In this example, the soluble CNTFR polypeptide includes a C-terminal truncation of amino acids 343-372 relative to a wild-type CNTF receptor having the amino acid sequence set forth in SEQ ID NO:1. In certain aspects, such a soluble CNTFR polypeptide does not include a signal peptide (underlined in Table 2).

Soluble CNTFR polypeptides of the present disclosure include (or correspond to) any of the CNTFR polypeptides presented in the Experimental section below and any of FIG. 7, FIG. 8 and FIG. 9.

According to certain embodiments, a soluble CNTFR polypeptide of the present disclosure includes an amino acid sequence that has 70% or greater, 75% or greater, 80% or greater, 85% or greater, 90% or greater, 95% or greater, or 99% or greater identity to amino acids 23-342 of SEQ ID NO:1 or SEQ ID NO:2, or a fragment thereof, such as a fragment having a length of from 250 to 319 amino acids, 250 to 260 amino acids, 260 to 270 amino acids, 270 to 280 amino acids, 280 to 290 amino acids, 290 to 300 amino acids, 300 to 310 amino acids, or 310 to 319 amino acids. In addition to being soluble, such a CNTFR polypeptide may include one or more desirable features, such as reduced binding affinity for one or more ligand-CNTFR complex subunits (e.g., LIFR, gp130, or both), increased binding affinity/specificity for a CNTFR ligand (e.g., CLCF1), reduced binding affinity for a CNTFR ligand (e.g., CNTF, NP, etc.), and any combination thereof.

Antibodies

In certain aspects, the agent that specifically binds a ligand of CNTFR is an antibody. The terms "antibody", "antibodies" and "immunoglobulin" include antibodies or immunoglobulins of any isotype, whole antibodies (e.g., antibodies composed of a tetramer which in turn is composed of two dimers of a heavy and light chain polypeptide); single chain antibodies; fragments of antibodies (e.g., fragments of whole or single chain antibodies) which retain specific binding to the CNTFR ligand (e.g., CLCF1, NP and/or CNTF), including, but not limited to Fab, Fab', Fv, scFv, and diabodies; chimeric antibodies; and humanized antibodies, e.g., humanized whole antibodies or humanized antibody fragments).

The "Fab" fragment contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

"Single-chain Fv" or "scFv" antibody fragments comprise the $V_H$ and $V_L$ domains of an antibody, where these domains are present in a single polypeptide chain. In some embodiments, the Fv polypeptide further comprises a polypeptide linker between the $V_H$ and $V_L$ domains, which enables the sFv to form the desired structure for antigen binding.

TABLE 2

Amino Acid Sequence of an Example Soluble CNTFR Polypeptide

| | Amino Acid Sequence |
|---|---|
| Example Soluble CNTFR Polypeptide (SEQ ID NO: 2) (R110Q, T174P, Y177H, K178N, S237F, T268A, D269A, I287F) | <u>MAAPVPWACCAVLAAAAAVVY</u>AQRHSPQEAPHVQYERLGSDVTLPCGTA NWDAAVTWRVNGTDLAPDLLNGSQLVLHGLELGHSGLYACFHRDSWHLR HQVLLHVGLPPQEPVLSCRSNTYPKGFYCSWHLPTPTYIPNTFNVTVLH GSKIMVCEKDPALKNRCHIRYMHLFSPI KHNVSISVSNALGHNATAITF DEFTIVKPDPPENVVARPVPSNPRRLEVTWQTPSTWPDPEFFPLKFFLR YRPLILDQWQHVELSDGTAHTIAAAYAGKEYIIQVAAKDNEFGTWSDWS VAAHATPWTEEPRHLTTEAQAAETTTSTTSSLAPPPTTKICDPGELGS |

In certain aspects, an antibody that specifically binds a ligand of CNTFR specifically binds to CLCF1 preferentially as compared to CNTF or NP1. According to certain embodiments, an antibody that specifically binds a ligand of CNTFR specifically binds to CLCF1 and not CNTF or NP1.

Engineering/Development and Production of CNTFR Ligand-Binding Agents

Also provided by the present disclosure are methods of engineering/developing additional CNTFR ligand-binding agents having one or more desired functionalities. The manner in which the CNTFR ligand-binding agents are developed may vary. Rational and combinatorial approaches may be used to engineer CNTFR ligand-binding agents with novel properties, e.g., reduced binding affinity for one or more ligand-CNTFR complex subunits (e.g., LIFR, gp130, or both), increased binding affinity and/or specificity for a CNTFR ligand (e.g., CLCF1), reduced binding affinity for a CNTFR ligand (e.g., CNTF, NP, etc.), and any combination thereof. For example, to develop a soluble CNTFR polypeptide or antibody, a library of CNTFR polypeptides or antibodies may be created and screened, e.g., by bacterial display, phage display, yeast surface display, fluorescence-activated cell sorting (FACS), and/or any other suitable screening method.

Yeast surface display is a powerful combinatorial technology that has been used to engineer proteins with novel molecular recognition properties, increased target binding affinity, proper folding, and improved stability. In this platform, libraries of protein variants are generated and screened in a high-throughput manner to isolate mutants with desired biochemical and biophysical properties. As demonstrated in the Examples section below, the present inventors have successfully employed yeast surface display for engineering CNTFR polypeptides with altered binding affinities for CLCF1, LIFR and gp130 in a desirable manner. Yeast surface display benefits from quality control mechanisms of the eukaryotic secretory pathway, chaperone-assisted folding, and efficient disulfide bond formation.

One example approach for developing a soluble CNTFR polypeptide having a desirable property of interest involves genetically fusing a CNTFR polypeptide to the yeast mating agglutinin protein Aga2p, which is attached by two disulfide binds to the yeast cell wall protein Aga1p. This Aga2p-fusion construct, and a chromosomally integrated Aga1p expression cassette, may be expressed under the control of a suitable promoter, such as a galactose-inducible promoter. N- or C-terminal epitope tags may be included to measure cell surface expression levels by flow cytometry using fluorescently labeled primary or secondary antibodies. This construct represents the most widely used display format, where the N-terminus of the CNTFR polypeptide (or other protein to be engineered) is fused to Aga2, but several alternative variations of the yeast surface display plasmid have been described and may be employed to develop a soluble CNTFR polypeptide of the present disclosure. One of the benefits of this screening platform over panning-based methods used with phage or mRNA display is that two-color FACS can be used to quantitatively discriminate clones that differ by as little as two-fold in binding affinity to a particular target.

To selectively mutate CNTFR at the DNA level, an example approach is error prone PCR, which can be used to introduce mutations by any number of altered reaction conditions including using a polymerase that does not possess proofreading (i.e. exonuclease) activity, using mixtures of triphosphate derivatives of nucleoside analogues, using altered ratios of dNTPs, varying concentrations of magnesium or manganese, or the like. Alternatively, degenerate codons can be introduced by oligonucleotide assembly using, e.g., overlap extension PCR. Next, the genetic material may be amplified using flanking primers with sufficient overlap with the yeast display vector for homologous recombination in yeast. These methods allow CNTFR libraries to be created at relatively low cost and effort. Synthetic libraries and recent methods have been developed that allow defined control over library composition.

In certain aspects, a display library (e.g., a yeast display library) is screened for binding to the target of interest (e.g., CNTFR ligand of interest, such as CLCF1) by FACS. Two-color FACS may be used for library screening, where one fluorescent label can be used to detect the c-myc epitope tag and the other to measure interaction of the CNTFR polypeptide against the binding target of interest. Different instrument lasers and/or filter sets can be used to measure excitation and emission properties of the two fluorophores at single-cell resolution. This enables yeast expression levels to be normalized with binding. That is, a CNTFR polypeptide that exhibits poor yeast expression but binds a high amount of a target can be distinguished from a CNTFR polypeptide that is expressed at high levels but binds weakly to a target. Accordingly, a two-dimensional flow cytometry plot of expression versus binding will result in a diagonal population of yeast cells that bind to target antigen. High-affinity binders can be isolated using library sort gates. Alternatively, in an initial sort round it could be useful to clear the library of undesired clones that do not express full-length protein.

Following enrichment of CNTFR libraries for clones encoding CNTFR polypeptides of interest, the yeast plasmids are recovered and sequenced. Additional rounds of FACS can be performed under increased sorting stringency. The binding affinities or kinetic off-rates of individual yeast-displayed CNTFR clones may then be measured.

Once CNTFR polypeptides of interest have been identified by surface display (e.g., yeast surface display), the engineered CNTFR polypeptides may be produced using a suitable method. According to certain embodiments, the CNTFR polypeptide is produced by solid phase peptide synthesis. CNTFR polypeptide sequences may be synthesized using solid phase peptide chemistry on an automated synthesizer. For example, standard 9-fluorenylmethyloxy-carbonyl (Fmoc)-based solid phase peptide chemistry may be employed. Solid phase synthesis may be followed by purification, e.g., by reversed-phase high-performance liquid chromatography (RP-HPLC).

In certain aspects, soluble CNTFR polypeptides are produced using a recombinant DNA approach. Strategies have been developed for producing proteins such as CNTFR polypeptides using recombinant methods in a variety of host cell types. For example, functional soluble CNTFR polypeptides may be produced with barnase as a genetic fusion partner, which promotes folding in the *E. coli* periplasmic space and serves as a useful purification handle. According to certain embodiments, the engineered soluble CNTFR polypeptide is expressed in yeast (e.g., the yeast strain *Pichia pastoris* or *Saccharomyces* cerevesiae) or mammalian cells (e.g. human embryonic kidney cells or Chinese hamster ovary cells). The expression construct may encode one or more tags (e.g., a C-terminal hexahistidine tag for purification by, e.g., metal chelating chromatography (Ni-NTA)). Size exclusion chromatography may then be used to remove aggregates, misfolded multimers, and the like.

Aspects of the present disclosure include nucleic acids that encode the CNTFR ligand binding agents of the present disclosure. That is, provided are nucleic acids that encode any of the CNTFR ligand binding agents described herein (e.g., any of the soluble CNTFR polypeptides, antibodies, etc. described herein). In certain aspects, such a nucleic acid is present in an expression vector. The expression vector includes a promoter operably linked to the nucleic acid encoding the agent (e.g., soluble CNTFR polypeptide), the promoter being selected based on the type of host cell selected to express the agent. Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance, neomycin resistance, and/or the like) to permit detection of those cells transformed with the desired DNA sequences.

Also provided are host cells that include a nucleic acid that encodes any of the CNTFR ligand binding agents described herein (e.g., any of the soluble CNTFR polypeptides, antibodies, etc. described herein), as well as any expression vectors including the same. *Escherichia coli* is an example of a prokaryotic host cell that can be used for cloning a nucleic acid encoding a CNTFR ligand binding agent of the present disclosure. Other microbial hosts suitable for use include bacilli, such as *Bacillus subtilis*, and other enterobacteriaceae, such as *Salmonella, Serratia,* and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* (e.g., *S. cerevisiae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells (e.g., mammalian cells grown in in vitro cell culture) can also be used to express and produce the CNTFR ligand binding agents of the present disclosure. Suitable mammalian host cells include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like. Expression vectors for these cells can include expression control sequences, such as an origin of replication, a promoter, and an enhancer, and necessary processing information sites, such as ribosome binding sites, RNA splice sites, polyadenylation sites, and transcriptional terminator sequences. Examples of suitable expression control sequences are promoters derived from immunoglobulin genes, SV40, adenovirus, bovine papilloma virus, cytomegalovirus and the like.

Once synthesized (either chemically or recombinantly), the CNTFR ligand binding agents can be purified according to standard procedures known in the art, including ammonium sulfate precipitation, affinity columns, column chromatography, high performance liquid chromatography (HPLC) purification, gel electrophoresis, and the like. A subject CNTFR ligand binding agent can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than the CNTFR ligand binding agent, etc.

Fusion Proteins and Conjugates

In certain aspects, provided are CNTFR ligand-binding agents (e.g., any of the soluble CNTFR polypeptides or antibodies described herein) stably associated with (e.g., fused, conjugated, or otherwise attached to) a heterologous moiety.

In some embodiments, provided are fusion proteins in which a polypeptide CNTFR ligand-binding agent (e.g., any of the soluble CNTFR polypeptides or antibodies of the present disclosure) is fused to a heterologous polypeptide. Heterologous polypeptides of interest include, but are not limited to, an Fc domain (e.g., a human or mouse Fc domain), an albumin, a transferrin, XTEN, a homo-amino acid polymer, a proline-alanine-serine polymer, an elastin-like peptide, or any combination thereof. In certain aspects, the heterologous polypeptide increases the stability and/or serum half-life of the CNTFR ligand-binding agent upon its administration to an individual in need thereof, as compared to the same CNTFR ligand-binding agent which is not fused to the heterologous polypeptide. In certain aspects, provided are fusion proteins that include any of the soluble CNTFR polypeptides of the present disclosure fused to a human Fc domain (e.g., a full-length human Fc domain or fragment thereof). According to certain embodiments, such a fusion protein finds use, e.g., in administering to an individual in need thereof in accordance with the methods of the present disclosure (e.g., an individual having a cell proliferative disorder associated with CNTFR signaling). A non-limiting example of a human Fc domain that may be fused to any of the soluble CNTFR polypeptides of the present disclosure is a human IgG1 Fc domain having the sequence set forth in Table 3 below (SEQ ID NO:3), or a fragment thereof.

TABLE 3

Amino Acid Sequence of an Example Human Fc Domain

| | Amino Acid Sequence |
|---|---|
| Example Human Fc Domain (SEQ ID NO: 3) | DKTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSR WQQGNVFSCSVMHEALHNHYTQKSLSLSPGK |

According to certain embodiments, provided are conjugates in which a CNTFR ligand-binding agent of the present disclosure is conjugated to a moiety. Moieties of interest include, but are not limited to, polyethylene glycol (PEG), an anti-cancer drug, a detectable label, and combinations thereof.

Anti-cancer drugs of interest include agents that inhibit cell proliferation and/or kill cancer cells. Such agents may vary and include cytostatic agents and cytotoxic agents (e.g., an agent capable of killing a target cell tissue with or without being internalized into a target cell). In certain aspects, the therapeutic agent is a cytotoxic agent selected from an enediyne, a lexitropsin, a duocarmycin, a taxane, a puromycin, a dolastatin, a maytansinoid, and a *vinca* alkaloid. In some embodiments, the cytotoxic agent is paclitaxel, docetaxel, CC-1065, CPT-11 (SN-38), topotecan, doxorubicin, morpholino-doxorubicin, rhizoxin, cyanomorpholino-doxorubicin, dolastatin-10, echinomycin, combretastatin, calicheamicin, maytansine, maytansine DM1, maytansine DM4, DM-1, an auristatin or other dolastatin derivatives, such as auristatin E or auristatin F, AEB (AEB-071), AEVB (5-benzoylvaleric acid-AE ester), AEFP (antibody-endostatin fusion protein), MMAE (monomethylauristatin E), MMAF (monomethylauristatin F), pyrrolobenzodiazepines (PBDs), eleutherobin, netropsin, or any combination thereof. According to certain embodiments, the agent is a protein toxin selected from hemiasterlin and hemiasterlin analogs such as HTI-286 (e.g., see U.S. Pat. No. 7,579,323; WO 2004/026293; and U.S. Pat. No. 8,129,407, the full disclosures of which are incorporated herein by reference), abrin, brucine, cicutoxin, diphtheria toxin, batrachotoxin, botulism toxin, shiga toxin, endotoxin, *Pseudomonas* exotoxin, *Pseudomonas* endotoxin, tetanus toxin, pertussis toxin, anthrax toxin, cholera toxin, falcarinol, fumonisin BI, fumonisin B2, afla toxin, maurotoxin, agitoxin, charybdotoxin, margatoxin, slotoxin, scyllatoxin, hefutoxin, calciseptine, taicatoxin, calcicludine, geldanamycin, gelonin, lotaustralin, ocratoxin A, patulin, ricin, strychnine, trichothecene, zearlenone, and tetradotoxin. Enzymatically active toxins and fragments thereof which may be employed include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes.

Detectable labels include labels that may be detected in an application of interest (e.g., in vitro and/or in vivo research and/or clinical applications). Detectable labels of interest include radioisotopes, enzymes that generate a detectable product (e.g., horseradish peroxidase, alkaline phosphatase, etc.), fluorescent proteins, paramagnetic atoms, and the like. In certain aspects, the CNTFR ligand-binding agent is conjugated to a specific binding partner of detectable label (e.g., conjugated to biotin such that detection may occur via a detectable label that includes avidin/streptavidin).

According to certain embodiments, the agent is a labeling agent that finds use in in vivo imaging, such as near-infrared (NIR) optical imaging, single-photon emission computed tomography (SPECT)/CT imaging, positron emission tomography (PET), nuclear magnetic resonance (NMR) spectroscopy, or the like. Labeling agents that find use in such applications include, but are not limited to, fluorescent labels, radioisotopes, and the like. In certain aspects, the labeling agent is a multi-modal in vivo imaging agent that permits in vivo imaging using two or more imaging approaches (e.g., see Thorp-Greenwood and Coogan (2011) *Dalton Trans.* 40:6129-6143).

In certain aspects, the labeling agent is an in vivo imaging agent that finds use in near-infrared (NIR) imaging applications, which agent is selected from a Kodak X-SIGHT dye, Pz 247, DyLight 750 and 800 Fluors, Cy 5.5 and 7 Fluors, Alexa Fluor 680 and 750 Dyes, IRDye 680 and 800CW Fluors. According to certain embodiments, the labeling agent is an in vivo imaging agent that finds use in SPECT imaging applications, which agent is selected from $^{99m}$Tc, $^{111}$In, $^{123}$In, $^{201}$Tl, and $^{133}$Xe. In certain aspects, the labeling agent is an in vivo imaging agent that finds use in positron emission tomography (PET) imaging applications, which agent is selected from $^{11}$C, $^{13}$N, $^{15}$O, $^{18}$F, $^{64}$Cu, $^{62}$Cu, $^{124}$I, $^{76}$Br, $^{82}$Rb and $^{68}$Ga.

Linkers that find use in the conjugates of the present disclosure include ester linkers, amide linkers, maleimide or maleimide-based linkers; valine-citrulline linkers; hydrazone linkers; N-succinimidyl-4-(2-pyridyldithio)butyrate (SPDB) linkers; Succinimidyl-4-(N-maleimidomethyl)cyclohexane-1-carboxylate (SMCC) linkers; vinylsulfone-based linkers; linkers that include polyethylene glycol (PEG), such as, but not limited to tetraethylene glycol; linkers that include propanoic acid; linkers that include caproleic acid, and linkers including any combination thereof.

Numerous strategies are available for linking a CNTFR ligand-binding agent to a moiety of interest through a linker. For example, the moiety of interest may be derivatized by covalently attaching the linker to the drug, where the linker has a functional group capable of reacting with a "chemical handle" on the CNTFR ligand-binding agent. The functional group on the linker may vary and may be selected based on compatibility with the chemical handle on the CNTFR ligand-binding agent. According to one embodiment, the chemical handle on the CNTFR ligand-binding agent is provided by incorporation of an unnatural amino acid having the chemical handle into the CNTFR ligand-binding agent. Such an unnatural amino acid may be incorporated into a CNTFR ligand-binding agent, e.g., via chemical synthesis or recombinant approaches (e.g., using a suitable orthogonal amino acyl tRNA synthetase-tRNA pair for incorporation of the unnatural amino acid during translation in a host cell).

The functional group of an unnatural amino acid present in the CNTFR ligand-binding agent may be an azide, alkyne, alkene, amino-oxy, hydrazine, aldehyde, nitrone, nitrile oxide, cyclopropene, norbornene, iso-cyanide, aryl halide, boronic acid, or other suitable functional group, and the functional group on the linker is selected to react with the functional group of the unnatural amino acid (or vice versa).

Compositions

Also provided are compositions that include a CNTFR ligand-binding agent of the present disclosure. The compositions may include any of the CNTFR ligand-binding agents described herein, including any of the soluble CNTFR polypeptides and antibodies described herein.

In certain aspects, the compositions include a CNTFR ligand-binding agent of the present disclosure present in a liquid medium. The liquid medium may be an aqueous liquid medium, such as water, a buffered solution, and the like. One or more additives such as a salt (e.g., NaCl, $MgCl_2$, KCl, $MgSO_4$), a buffering agent (a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.), a protease inhibitor, glycerol, and the like may be present in such compositions.

Pharmaceutical compositions are also provided. The pharmaceutical compositions include any of the CNTFR ligand-binding agents of the present disclosure (e.g., any of the soluble CNTFR polypeptides and antibodies of the present disclosure), and a pharmaceutically-acceptable carrier. The pharmaceutical compositions generally include a therapeutically effective amount of the CNTFR ligand-binding agent. By "therapeutically effective amount" is meant a dosage sufficient to produce a desired result, e.g., an amount sufficient to effect beneficial or desired therapeutic (including preventative) results, such as a reduction in cellular proliferation in an individual having a cell proliferative disorder associated with CNTFR signaling.

A CNTFR ligand-binding agent of the present disclosure can be incorporated into a variety of formulations for therapeutic administration. More particularly, the CNTFR ligand-binding agent can be formulated into pharmaceutical compositions by combination with appropriate pharmaceutically acceptable excipients or diluents, and may be formulated into preparations in solid, semi-solid, liquid or gaseous forms, such as tablets, capsules, powders, granules, ointments, solutions, injections, inhalants and aerosols.

Formulations of the CNTFR ligand-binding agents of the present disclosure suitable for administration to an individual (e.g., suitable for human administration) are generally sterile and may further be free of detectable pyrogens or other contaminants contraindicated for administration to an individual according to a selected route of administration.

In pharmaceutical dosage forms, the CNTFR ligand-binding agent can be administered alone or in appropriate association, as well as in combination, with other pharmaceutically-active compounds. The following methods and excipients are merely examples and are in no way limiting.

For oral preparations, the CNTFR ligand-binding agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The CNTFR ligand-binding agents can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The pharmaceutical composition may be in a liquid form, a lyophilized form or a liquid form reconstituted from a lyophilized form, where the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration.

An aqueous formulation of the CNTFR ligand-binding agent may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

Methods of Use

Also provided are methods of using the CNTFR ligand-binding agents and compositions of the present disclosure. According to certain embodiments, provided are methods that include administering to an individual in need thereof a therapeutically effective amount of a CNTFR ligand-binding agent or pharmaceutical composition of the present disclosure, where binding of the agent to the ligand inhibits binding of the ligand to CNTFR. In certain aspects, the individual in need thereof has a cell proliferative disorder associated with CNTFR signaling, and the administering is effective in treating the cell proliferative disorder. In certain aspects, the cell proliferative disorder is cancer.

For example, in some embodiments, a CNTFR ligand-binding agent or pharmaceutical composition of the present disclosure inhibits growth, metastasis and/or invasiveness of a cancer cell(s) in a host when the CNTFR ligand-binding agent or pharmaceutical composition is administered in an effective amount. By "cancer cell" is meant a cell exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth and/or development in an immunocompromised non-human animal model, and/or any appropriate indicator of cellular transformation. "Cancer cell" may be used interchangeably herein with "tumor cell", "malignant cell" or "cancerous cell", and encompasses cancer cells of a solid tumor, a semi-solid tumor, a primary tumor, a metastatic tumor, and the like.

Cancers which may be treated using the methods of the present disclosure include, but are not limited to, solid tumors, lung cancer (e.g., non-small cell lung cancer (NSCLC), breast cancer, prostate cancer, pancreatic cancer, colorectal carcinoma, renal cell carcinoma, Hodgkin's lymphoma, Non-Hodgkin's lymphoma, anaplastic large cell lymphoma, acute myelogenous leukemia, multiple myeloma, and any other type of cancer which may be treated using a CNTFR ligand-binding agent or pharmaceutical composition of the present disclosure.

The CNTFR ligand-binding agent may be administered alone (e.g., in monotherapy) or in combination (e.g., in combination therapy) with one or more additional therapeutic agents.

In some embodiments, an effective amount of the CNTFR ligand-binding agent (or pharmaceutical composition including same) is an amount that, when administered alone (e.g., in monotherapy) or in combination (e.g., in combination therapy) with one or more additional therapeutic agents, in one or more doses, is effective to reduce the symptoms of a cell proliferative disorder (e.g., cancer) in the individual by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the symptoms in the individual in the absence of treatment with the CNTFR ligand-binding agent or pharmaceutical composition.

In certain aspects, the methods of the present disclosure inhibit growth, metastasis and/or invasiveness of cancer cells in the individual when the CNTFR ligand-binding agent or pharmaceutical composition is administered in an effective amount.

The CNTFR ligand-binding agent or pharmaceutical composition may be administered to an individual using any available method and route suitable for drug delivery, including in vivo and ex vivo methods, as well as systemic and localized routes of administration. Conventional and pharmaceutically acceptable routes of administration include intranasal, intramuscular, intra-tracheal, subcutaneous, intradermal, topical application, ocular, intravenous, intra-arterial, nasal, oral, and other enteral and parenteral routes of administration. Routes of administration may be combined, if desired, or adjusted depending upon the CNTFR ligand-binding agent and/or the desired effect. The CNTFR ligand-binding agents or pharmaceutical compositions may be administered in a single dose or in multiple doses. In some embodiments, the CNTFR ligand-binding agent or pharmaceutical composition is administered intravenously. In some embodiments, the CNTFR ligand-binding agent or pharmaceutical composition is administered by injection, e.g., for systemic delivery (e.g., intravenous infusion) or to a local site.

A variety of individuals are treatable according to the subject methods. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the individual will be human.

By "treating" or "treatment" is meant at least an amelioration of the symptoms associated with the cell proliferative disorder (e.g., cancer) of the individual, where amelioration is used in a broad sense to refer to at least a reduction in the magnitude of a parameter, e.g. symptom, associated with the cell proliferative disorder being treated. As such, treatment also includes situations where the cell proliferative disorder, or at least symptoms associated therewith, are completely inhibited, e.g., prevented from happening, or stopped, e.g., terminated, such that the individual no longer suffers from the cell proliferative disorder, or at least the symptoms that characterize the cell proliferative disorder.

Dosing is dependent on severity and responsiveness of the disease state to be treated. Optimal dosing schedules can be calculated from measurements of drug accumulation in the body of the patient. The administering physician can determine optimum dosages, dosing methodologies and repetition rates. Optimum dosages may vary depending on the relative potency of individual CNTFR ligand-binding agents, and can generally be estimated based on $EC_{50}$s found to be effective in in vitro and in vivo animal models, etc. In general, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, where the CNTFR ligand-binding agent or pharmaceutical composition is administered in maintenance doses, ranging from 0.01 μg to 100 g per kg of body weight, once or more daily, to once every several months, once every six months, once every year, or at any other suitable frequency.

The therapeutic methods of the present disclosure may include administering a single type of CNTFR ligand-binding agent to a subject, or may include administering two or more types of CNTFR ligand-binding agents to a subject by administration of a cocktail of different CNTFR ligand-binding agents, where the CNTFR ligand-binding agents are engineered to bind to, e.g., distinct CNTFR ligands.

In some embodiments, the methods include, prior to the administering the CNTFR ligand-binding agent or pharmaceutical composition, identifying the individual as having a cell proliferative disorder associated with CNTFR signaling. Identifying the individual as having a cell proliferative disorder associated with CNTFR signaling may be carried out using a variety of approaches and combinations thereof. In certain aspects, the identifying is based on CNTFR ligand abundance in a sample obtained from the individual. The CNTFR ligand may be one or more of CNTF, CLCF1, NP, etc., and any combinations thereof. In certain aspects, the sample includes cancer-associated fibroblasts (CAFs, such as normal lung fibroblasts (NLFs)), and identifying the individual as having a cell proliferative disorder associated with CNTFR signaling is based on the level of CLCF1 expression in the CAFs. In some embodiments, the CNTFR ligand abundance is quantified using a soluble CNTFR polypeptide as a CNTFR ligand capture agent, e.g., any of the soluble CNTFR polypeptides of the present disclosure. For example, the soluble CNTFR polypeptide used as a CNTFR ligand capture agent may be any of the soluble CNTFR polypeptides described herein.

According to certain embodiments, the identifying is based on CNTFR abundance and/or the abundance of CNTFR-gp130-LIFR tripartite receptor complexes in a sample obtained from the individual. In certain aspects, the identifying is based on the level of CNTFR signaling in a sample obtained from the individual. The level of CNTFR signaling may be based on the phosphorylation status of one or more CNTFR signaling pathway molecules. For example, the present inventors have determined that binding of CNTFR to CLCF1 results in activation of the Jak-STAT and Ras-Raf-MEK-ERK signaling pathways. As such, the abundance, activity, phosphorylation status, and/or the like of any of Jak, STAT, Ras, Raf, MEK, ERK, or any combination thereof, may be assessed to determine aberrant CNTFR signaling in the individual.

The identifying may be based on ligands, CNTFR molecules, CNTFR-gp130-LIFR tripartite receptor complexes, etc. quantified using any suitable approaches. According to certain embodiments, the identifying is based on an immunoassay. A variety of suitable immunoassay formats are available, including ELISA, flow cytometry assays, immunohistochemistry on tissue section samples, immunofluorescence on tissue section samples, Western analysis, and/or the like.

In some embodiments, the identifying is based on nucleic acid sequencing. For example, the number of sequencing reads corresponding to an mRNA encoding a protein of interest may be used to determine the expression level of the protein. In certain aspects, the sequencing is performed using a next-generation sequencing system, such as on a sequencing platform provided by Illumina® (e.g., the HiSeq™, MiSeq™ and/or Genome Analyzer™ sequencing systems); Ion Torrent™ (e.g., the Ion PGM™ and/or Ion Proton™ sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems); or any other sequencing platform of interest. Protocols for isolating nucleic acids from tissue or fluid samples, as well as protocols for preparing sequencing libraries having sequencing adapters appropriate for the desired sequencing platform are readily available.

In some embodiments, methods that include identifying the individual as having a cell proliferative disorder associated with CNTFR signaling further include obtaining the sample from the individual.

Also provided are methods that include identifying an individual as having a cell proliferative disorder associated with CNTFR signaling. Identifying the individual as having a cell proliferative disorder associated with CNTFR signaling may be carried out using a variety of approaches and combinations thereof. In certain aspects, the identifying is based on CNTFR ligand abundance in a sample obtained from the individual. The CNTFR ligand may be one or more of CNTF, CLCF1, NP, etc., and any combinations thereof. In certain aspects, the sample includes cancer-associated fibroblasts (CAFs, such as normal lung fibroblasts (NLFs)), and identifying the individual as having a cell proliferative disorder associated with CNTFR signaling is based on the level of CLCF1 expression in the CAFs. In some embodiments, the CNTFR ligand abundance is quantified using a soluble CNTFR polypeptide as a CNTFR ligand capture agent, e.g., any of the soluble CNTFR polypeptides of the present disclosure. For example, the soluble CNTFR polypeptide used as a CNTFR ligand capture agent may be any of the soluble CNTFR polypeptides described herein. According to certain embodiments, the identifying is based on CNTFR abundance and/or the abundance of CNTFR-gp130-LIFR tripartite receptor complexes in a sample obtained from the individual. In certain aspects, the identifying is based on the level of CNTFR signaling in a sample obtained from the individual. The level of CNTFR signaling may be based on the phosphorylation status of one or more CNTFR signaling pathway molecules. For example, the present inventors have determined that binding of CNTFR to CLCF1 results in activation of the Jak-STAT and Ras-Raf-MEK-ERK signaling pathways. As such, the abundance, activity, phosphorylation status, and/or the like of any of Jak, STAT, Ras, Raf, MEK, ERK, or any combination thereof, may be assessed to determine aberrant CNTFR signaling in the individual. The identifying may be based on ligands, CNTFR molecules, CNTFR-gp130-LIFR tripartite receptor complexes, etc. quantified using any suitable approaches, such as by immunoassay, nucleic acid sequencing, and/or the like. In some embodiments, the methods further include obtaining the sample from the individual.

The sample obtained from the individual may be any sample suitable for determining whether the individual has a cell proliferative disorder associated with CNTFR signaling. In certain aspects, the sample is a fluid sample, such as whole blood, serum, plasma, or the like. In some embodiments, the sample is a tissue sample. Tissue samples of interest include, but are not limited to, tumor biopsy samples, and the like.

Kits

Also provided by the present disclosure are kits. According to certain embodiments, the kits include a therapeutically effective amount of any of the CNTFR ligand-binding agents described herein, or any of the pharmaceutical compositions described herein, and instructions for administering the CNTFR ligand-binding agent or pharmaceutical composition to an individual in need thereof (e.g., an individual identified as having a cell proliferative disorder associated with CNTFR signaling. In certain aspects, the kits include a CNTFR ligand-binding agent or a pharmaceutical composition of the present disclosure, present in a container. The container may be a tube, vial, or the like. According to certain embodiments, the kit includes the CNTFR ligand-binding agent or the pharmaceutical composition present in one or more unit dosages, such as 1, 2 or more, 3 or more, 4 or more, 5 or more, etc. unit dosages.

Components of the kits may be present in separate containers, or multiple components may be present in a single container.

The instructions for administering the CNTFR ligand-binding agent or pharmaceutical composition to an individual may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

In some embodiments, provided are kits that include a CNTFR ligand capture agent and instructions for using the capture agent to quantify a CNTFR ligand abundance present in a biological sample. The CNTFR ligand may be one or more of CNTF, CLCF1, NP, etc., and any combinations thereof. In some embodiments, the CNTFR ligand abundance is quantified using a soluble CNTFR polypeptide as a CNTFR ligand capture agent, e.g., any of the soluble CNTFR polypeptides of the present disclosure. For example, the soluble CNTFR polypeptide used as a CNTFR ligand capture agent may be any of the soluble CNTFR polypeptides described herein.

The following examples are offered by way of illustration and not by way of limitation.

EXPERIMENTAL

Introduction

The communication between epithelial cells and their underlying stroma is an important but poorly understood aspect of organismal biology. If aberrantly regulated, these interactions can prove to be tumorigenic. Although cancer-associated fibroblasts (CAFs) are known to promote and sustain the growth of tumors, the underlying mechanisms remain incompletely understood. The inventors have identified a novel mechanism of communication in which CAFs secrete cardiotrophin-like cytokine factor 1 (CLCF1), a cytokine that binds ciliary neurotrophic factor receptor (CNTFR) on tumor cells and promotes neoplastic growth.

It was hypothesized that a soluble CNTFR polypeptide could be employed as a therapeutic to reduce CNTFR signaling, and that a soluble CNTFR polypeptide having a greater binding affinity for CLCF1 as compared to wild-type CNTFR would be desirable. To engineer a soluble CNTFR polypeptide having a greater binding affinity for CLCF1, mutations were randomly introduced into CNTFR through error-prone PCR. The resulting library was displayed as fusion proteins on the yeast cell surface (schematically illustrated in FIG. 4, panel A), where a subset retained binding to CLCF1.

Example 1—Recombinant Expression of Functional CLCF1

Figure 2:
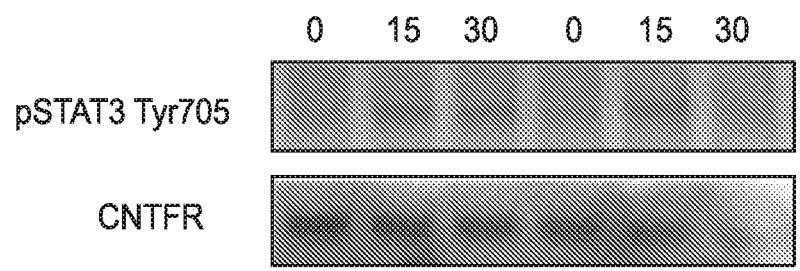
FIG. 2 provides data demonstrating that recombinant CLCF1 activates STAT3. Panel A: The level of p-STAT3 at Tyr705 in the NSCLC cell line A549 was detected 15 min and 30 min after treatment. Panel B: Intensity of p-STAT3 signal was quantified after normalized by CNTFR expression. Panel C: STAT3 activation was detected in other NSCLC cell lines such as H23 and H358.
Figure 2:
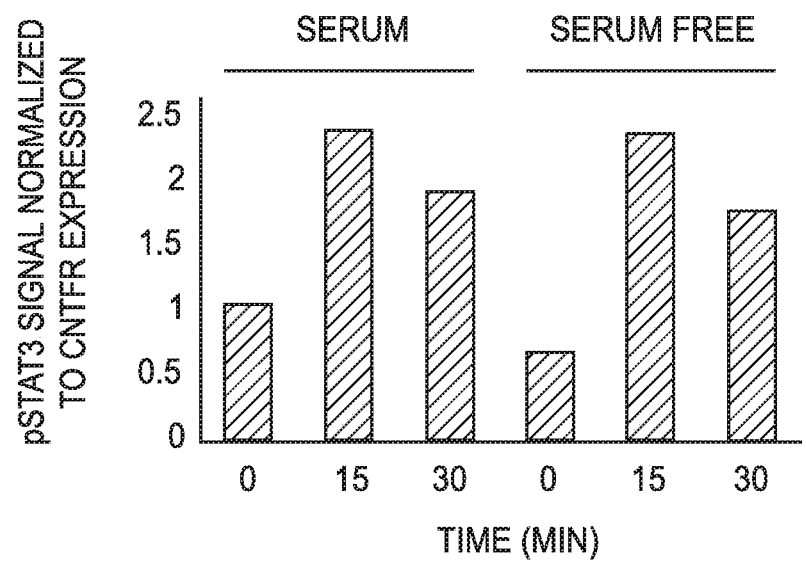
Figure 2:
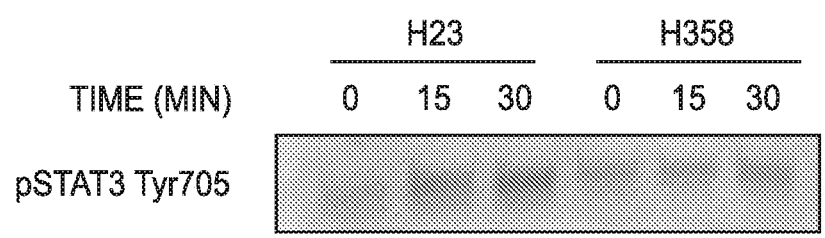

CLCF1 was cloned into the bacterial expression plasmid pET28b and transformed into Rosetta-gami 2(DE)3 cells. When expressed, recombinant CLCF1 accumulated in inclusion bodies, which were solubilized in 60% ddH2O, 40% acetonitrile, 0.1% TFA) containing 5 mM DTT. Reversed-phase high performance liquid chromatography was used to purify CLCF1. Treatment of the human non-small cell lung cancer cell line A549 with CLCF1 induced phosphorylation of STAT3 at Tyr705 within minutes (FIG. 2, panel A). Activation of STAT3 was also detected in two other cell lines H23 and H358 (FIG. 2, panel B). These results show that CLCF1 triggers an increase in phosphorylation of Tyr705 in STAT3.

Example 2—Recombinant CLCF1 Increases Cell Survival

Figure 3:
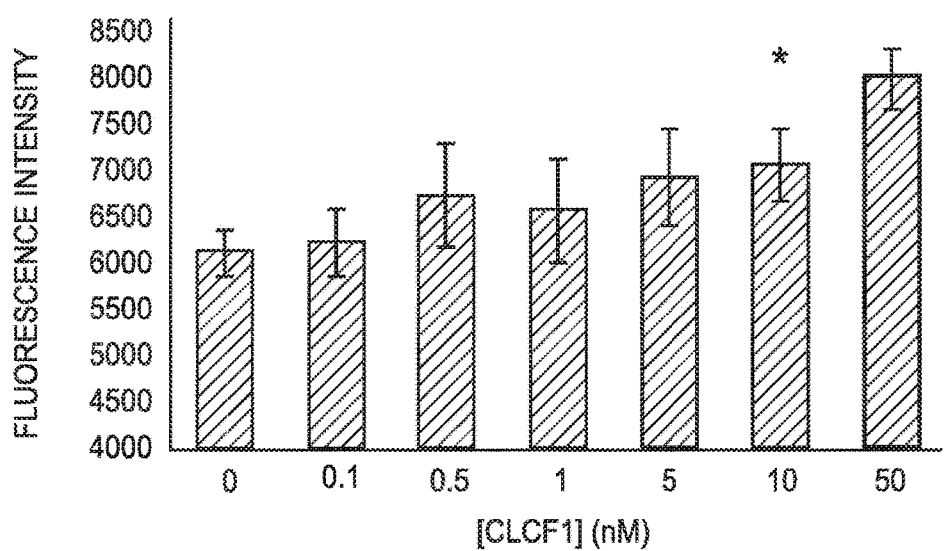
FIG. 3 shows data demonstrating the effect of CLCF1 treatment on A549 and H23 cell survival. After 24 hours of starvation in serum-free conditions, cells were treated with CLCF1 in serum free media for 72 h. CLCF1 increased A549 (panel A) and H23 (panel B) cell survival in a concentration dependent manner.
Figure 3:
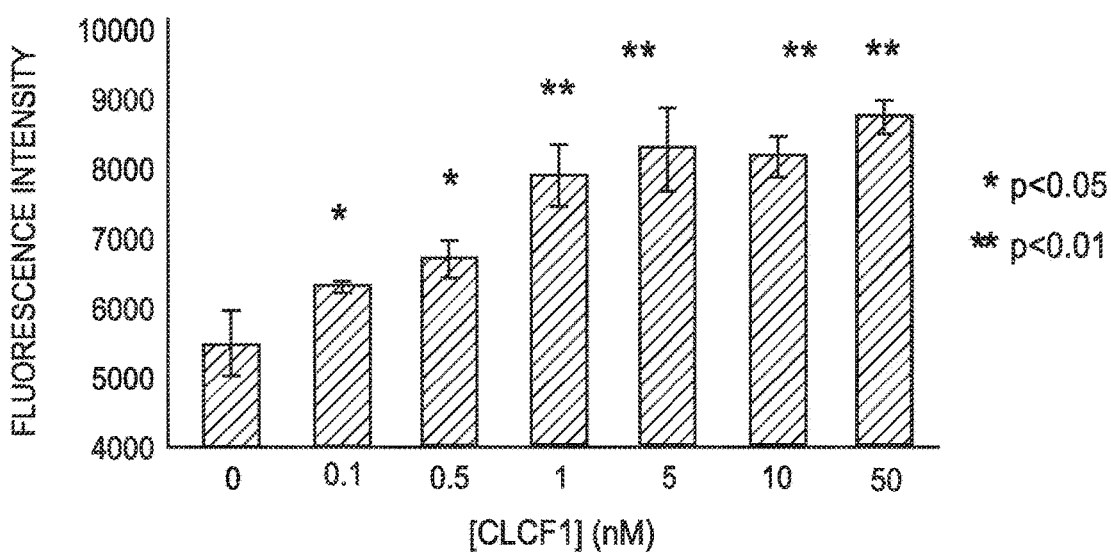

Cytokine mediated STAT3 activation has been shown to protect cells from apoptosis. To test whether CLCF1 can also increase cell survival, A549 cells were treated with CLCF1 following 24 hours of serum starvation. After 72 hours of incubation, CLCF1 was shown to increase cell survival in a concentration dependent manner (FIG. 3, panel A). When tested on H23 cells, again, higher CLCF1 concentration led to increased survival (FIG. 3, panel B). Such effect of CLCF1 treatment was not seen when serum was included in the assay suggesting that the effect is more apparent in stressor-induced conditions such as serum starvation.

Example 3—Yeast-Displayed CNTFR Binds to Recombinantly Expressed CLCF1

Figure 4:
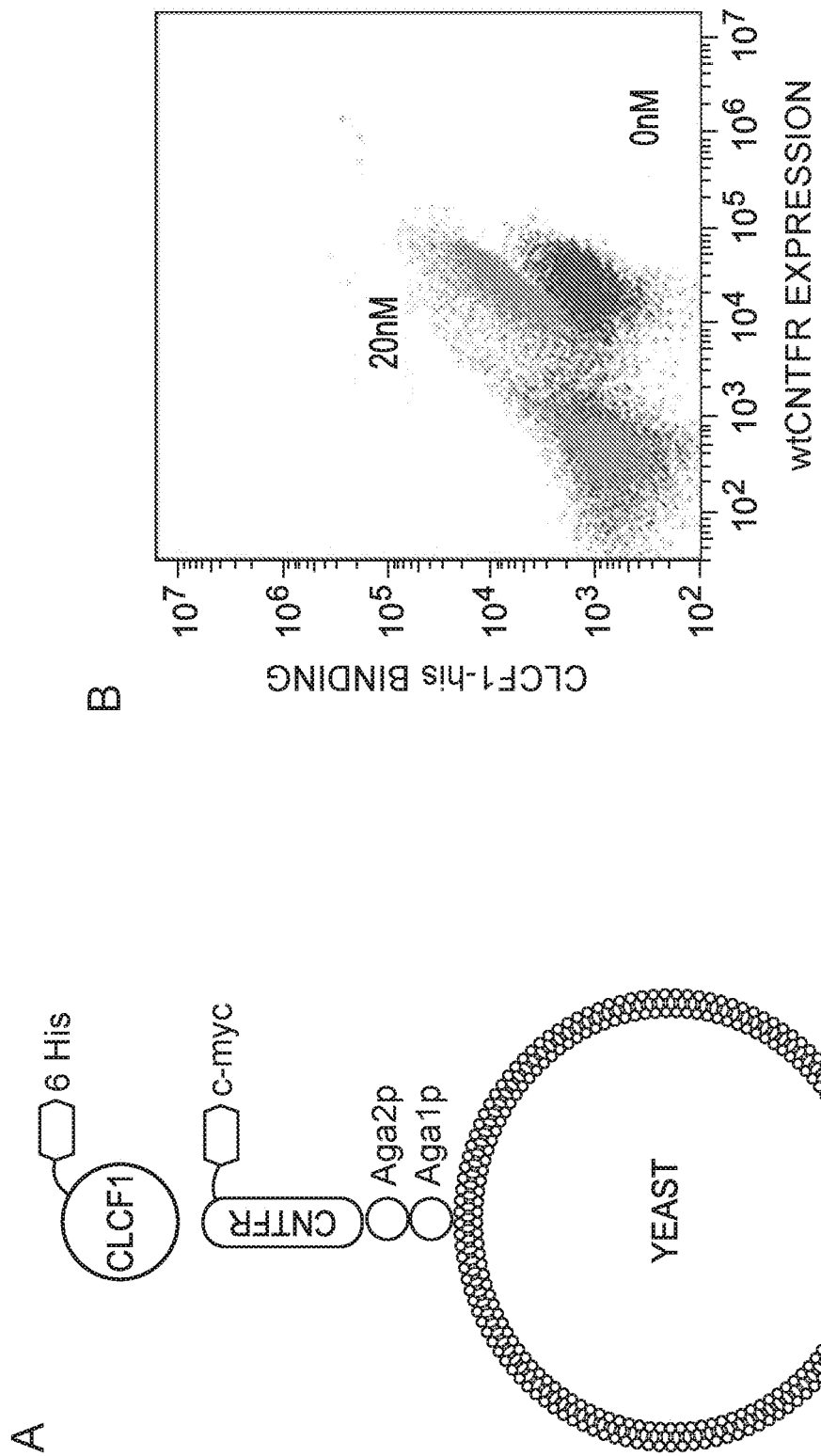
FIG. 4 Yeast surface display of CNTFR. Panel A: CNTFR was displayed as a fusion to yeast surface protein Aga2p. The displayed protein contains a c-terminal c-myc tag, which allows expression levels to be measured. Panel B: Flow cytometry scatter plot showing that when treated with 20 nM CLCF1, the yeast population expressing CNTFR has increased signal for CLCF1 binding.
Figure 5A:
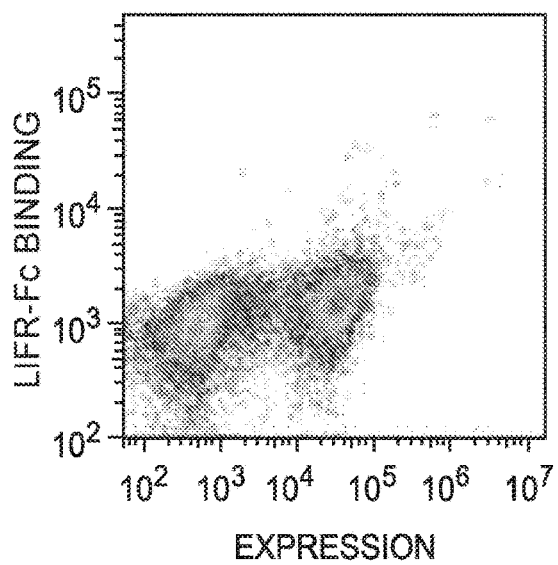
FIGS. 5A-5E Yeast-displayed CNTFR binds to the beta receptors in the presence of CLCF1. Scatter plots showing CNTFR displaying yeast incubated with anti-cMyc antibody only (panel A), with LIFR-Fc (panel B), with CLCF1 and LIFR-Fc (panel C), and with CLCF1, LIFR-Fc, and gp130-HIS (panel D). Fluorescently labeled secondary antibodies were used to detect binding of the various components by flow cytometry. Panel E: Overlay of the plots from panels B, C, and D.
Figure 5B:
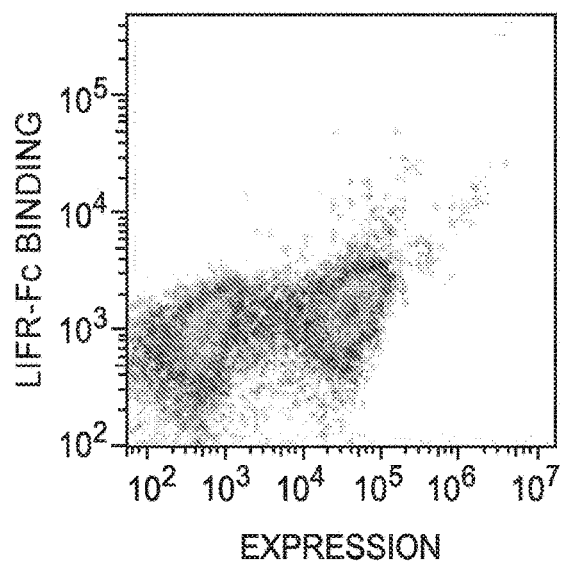
Figure 5C:
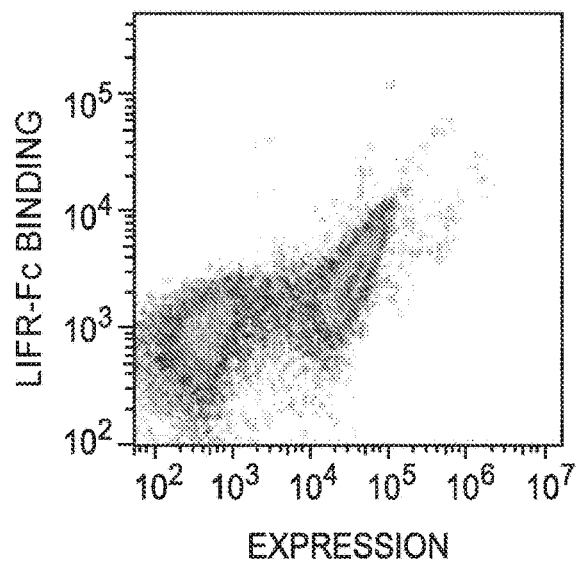
Figure 5D:
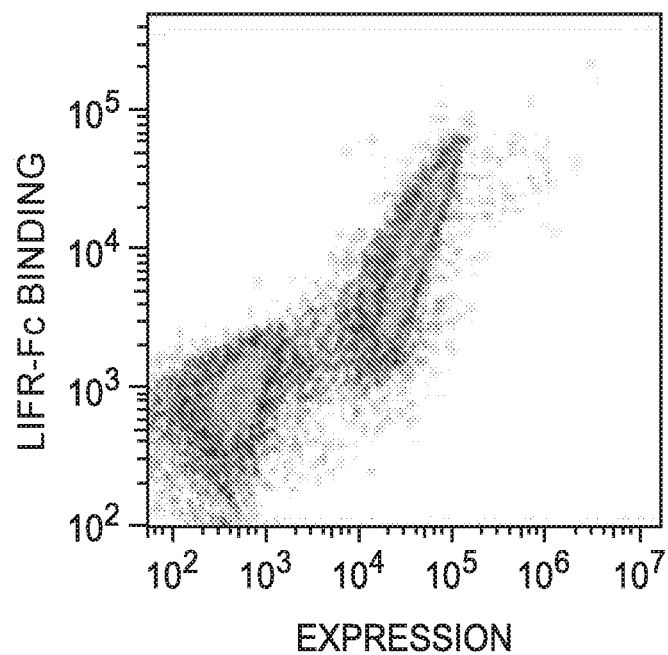
Figure 5E:
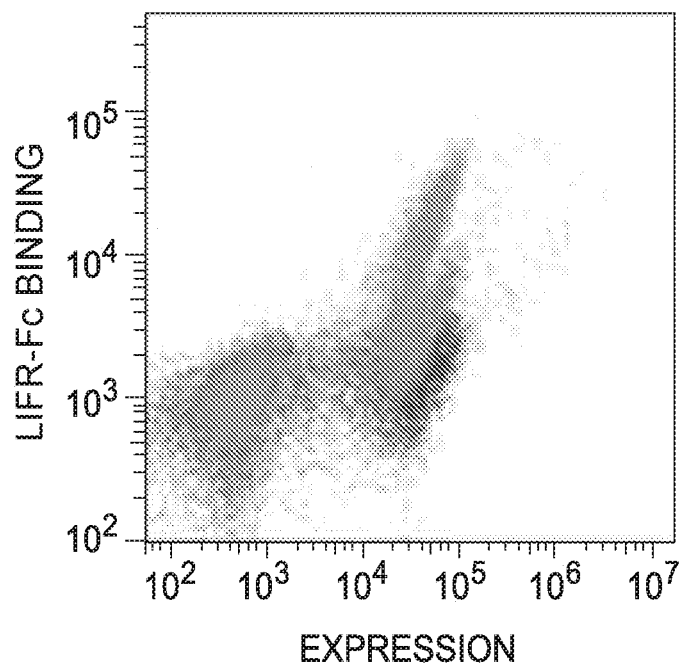
Figure 6A:
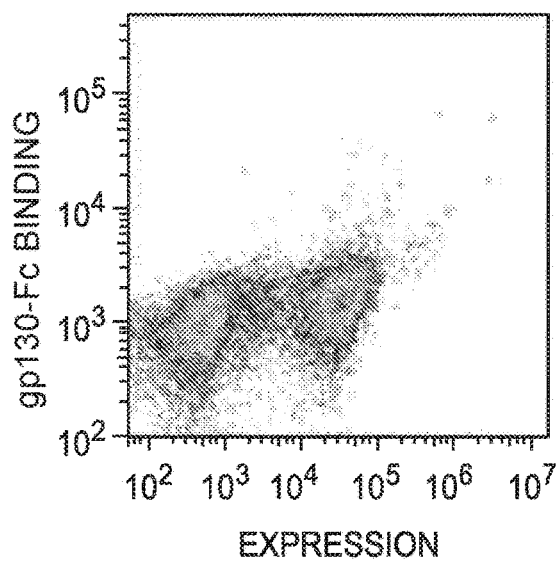
FIGS. 6A-6E Yeast-displayed CNTFR-CLCF1 can bind to gp130 without LIFR. Scatter plots showing CNTFR displaying yeast incubated with anti-cMyc antibody only (panel A), with gp130-Fc (panel B), with CLCF1 and gp130-Fc (panel C), and with CLCF1, gp130-Fc, and LIFR-HIS (panel D). Fluorescently labeled secondary antibodies were used to detect binding of the various components by flow cytometry. Panel E: Overlay of the plots from panels B, C, and D.
Figure 6B:
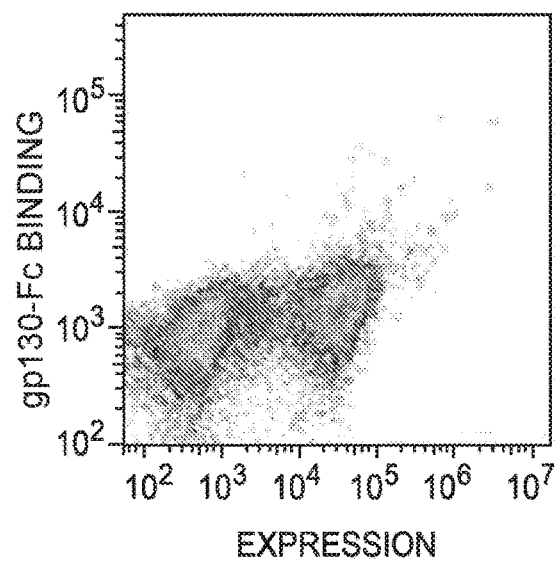
Figure 6C:
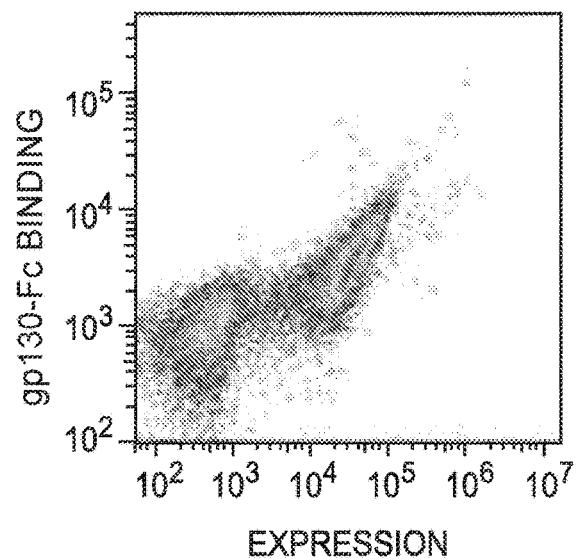
Figure 6D:
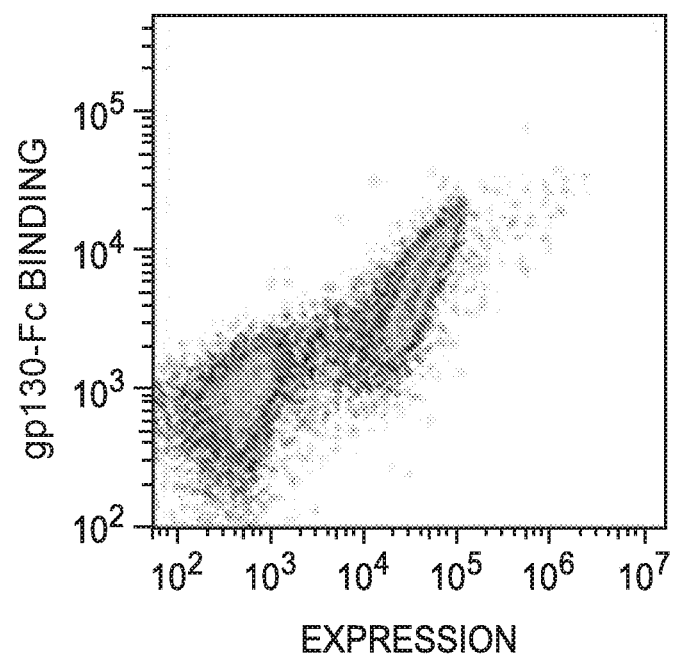
Figure 6E:
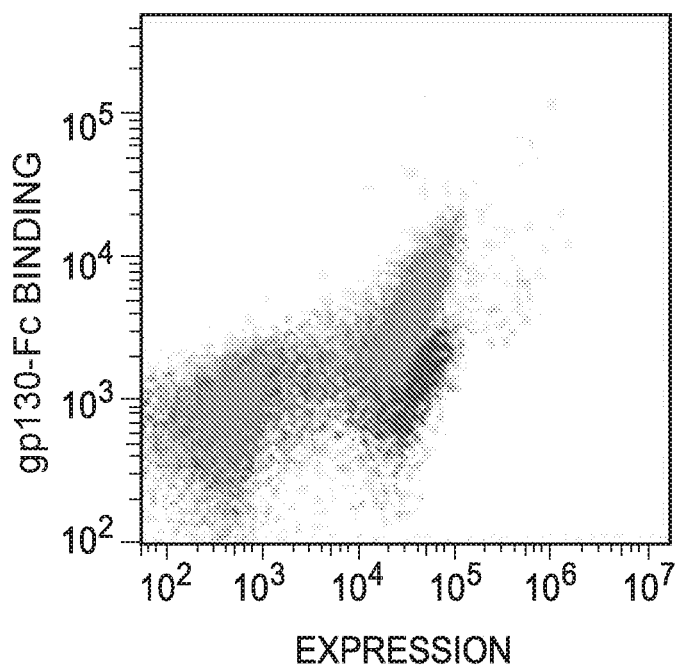

The extracellular domain of CNTFR was cloned into the yeast surface display plasmid pCTCON2 and transformed into the *Saccharomyces cerevisiae* strain EBY 100. This plasmid enables expression of CNTFR on the yeast cell surface through genetic linkage to the yeast agglutinin protein Aga2p (FIG. 4, panel A). CNTFR was flanked by N-terminal hemagglutinin (HA) and C-terminal c-Myc tags, which allows for detection of full-length protein by antibody labeling and flow cytometry detection. Induced yeast demonstrated an expression percentage of 50%, and the expressing population mostly bound recombinantly expressed CLCF1 when incubated with 20 nM CLCF, as measured by flow cytometry using a secondary antibody (FIG. 4, panel B).

Example 4—Yeast-Displayed CNTFR Forms a Tripartite Receptor Complex with CLCF1, gp130, and LIFR As mentioned previously, the CNTFR-CLCF1 complex binds to gp130 and LIFR to form a tripartite receptor complex. Therefore, a fully functional CNTFR is expected to bind to the two beta subunits when incubated with CLCF1. To prepare soluble constructs of LIFR and gp130, the extracellular domains were cloned into mammalian expression plasmid Add2 and transfected into human embryonic kidney (HEK) 293 suspension cells. The constructs were prepared as His-tag and mouse IgG2a fusions to facilitate purification. The His-tagged constructs were purified using nickel affinity chromatography, and the Fc-fusion constructs were purified using protein A affinity chromatography. When yeast-displayed CNTFR was incubated with LIFR-Fc, no binding signal was detected, which was expected since without CLCF1, CNTFR does not bind to the beta receptors to activate the downstream signaling pathways (FIG. 5, panels A and B). However, upon addition of CLCF1, LIFR-Fc binding signaling increased, indicating that in the presence of CLCF1, CNTFR indeed interacts with LIFR (FIG. 5, panel C). When yeast displayed-CNTFR was incubated with CLCF1 and gp130, LIFR-Fc binding signal increased even higher, indicating that gp130 further contributes to binding between LIFR and CNTFR (FIG. 5, panels D and E).

Several previous studies suggest that CNTFR interaction with the beta receptors may occur in a specific order. For example, it has been proposed that CNTF first binds to CNTFR, then recruits gp130, and finally complex with LIFR. The above experiments show that binding of CNTFR to LIFR can occur in the absence gp130 as long as CLCF1 binds first. In addition, without CLCF1, gp130-Fc showed no detectable binding to yeast-displayed CNTFR (FIG. 6, panels A and B). Upon addition of CLCF1 gp130-Fc signal increased significantly, indicating that gp130 can bind to CNTFR without LIFR (FIG. 6, panel C). When LIFR was added, there was a slight increase of gp130 binding signal. Together, the set of binding experiments shown in FIG. 6 suggests that there is synergistic or additive binding between LIFR and gp130 to CNTFR-CLCF1 (FIG. 6, panels D and E).

Example 5—Affinity Maturation of CNTFR to CLCF1 Using Yeast Surface Display

A protein engineering strategy was designed in which mutations were randomly introduced into the extracellular domain of CNTFR (20-342) using error-prone PCR. The resulting library, with an estimated diversity of about $1 \times 10^8$ transformants, was displayed as fusion proteins on the yeast cell surface as previously described. Using equilibrium binding conditions and screened by flow cytometric sorting (FACS), the library was enriched for variants showing increased CLCF1 binding, normalized for a given amount of c-Myc expression. Screening stringency was imparted by decreasing the concentration of CLCF1 incubated with the library in each successive round of sorting. After 3 rounds of screening using FACS, three yeast populations with different levels of CLCF1 binding signals were observed. Consensus mutations appeared in the two highest CLCF1 binding populations: T174P was observed in the intermediate affinity population, while S237F was observed in the highest affinity population (FIG. 7 and FIG. 8).

Example 6—Screening a Shuffled CNTFR Library to Identify High Affinity CLCF1 Variants Despite the enriched consensus mutations, the sorted library still contained substantial diversity. To test additive effects of the mutations found in the two higher binding populations, the clones were shuffled using Staggered Extension Process (StEP) method. To impose increased stringency with this library, a combination of equilibrium binding and kinetic off-rate screens were used. After 3 rounds of screening, a combination of four mutations (R110Q, T174P, S237F, and I287F) emerged (FIG. 9).

Figures 10A, 10B:
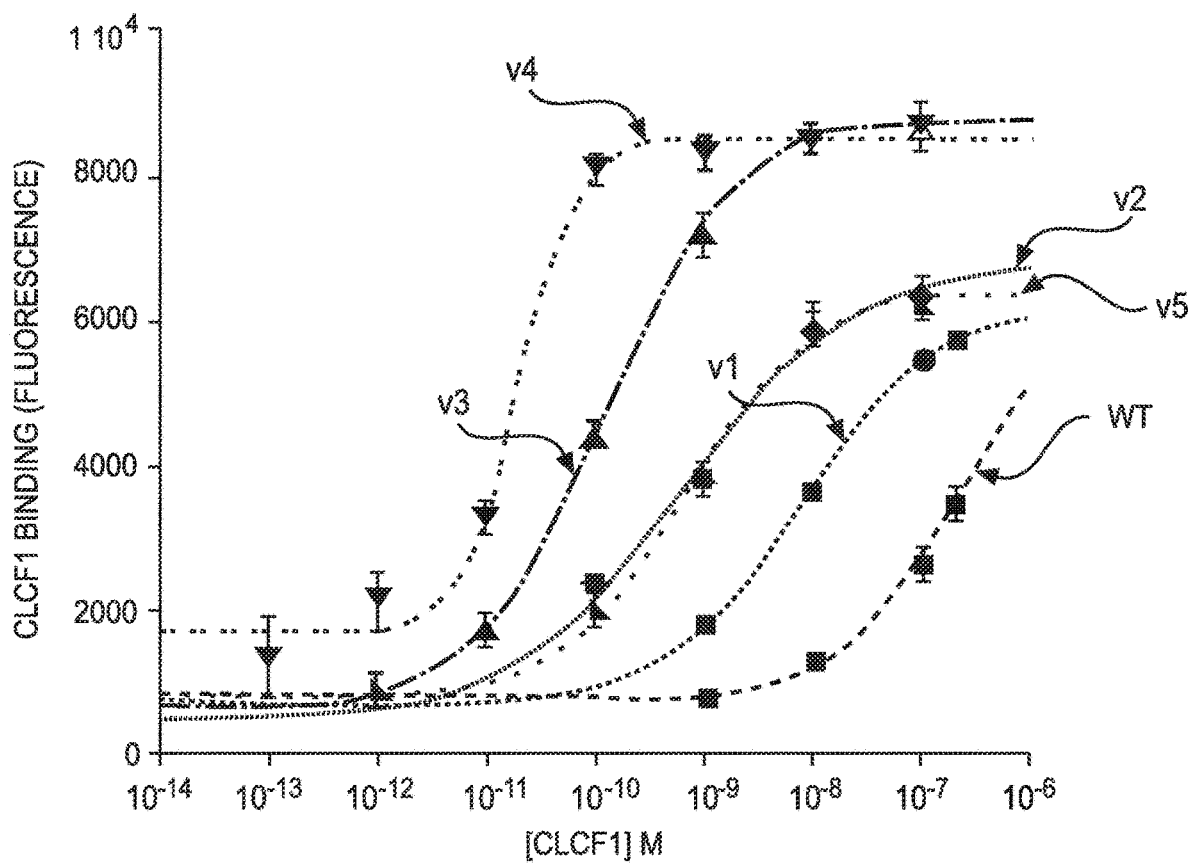
FIGS. 10A-10D characterization of affinity matured CNTFR variants. Panel A: CLCF1 binding to yeast expressing CNTFR constructs isolated from affinity maturation screens. Panel B: Apparent Kd values of yeast displayed CNTFR constructs. Panel C: CNTF binding to yeast displayed wild-type CNTFR and variant 4. Panel D: Variant 4 bound to mCLCF1 in addition to hCLCF1.
Figure 10C:
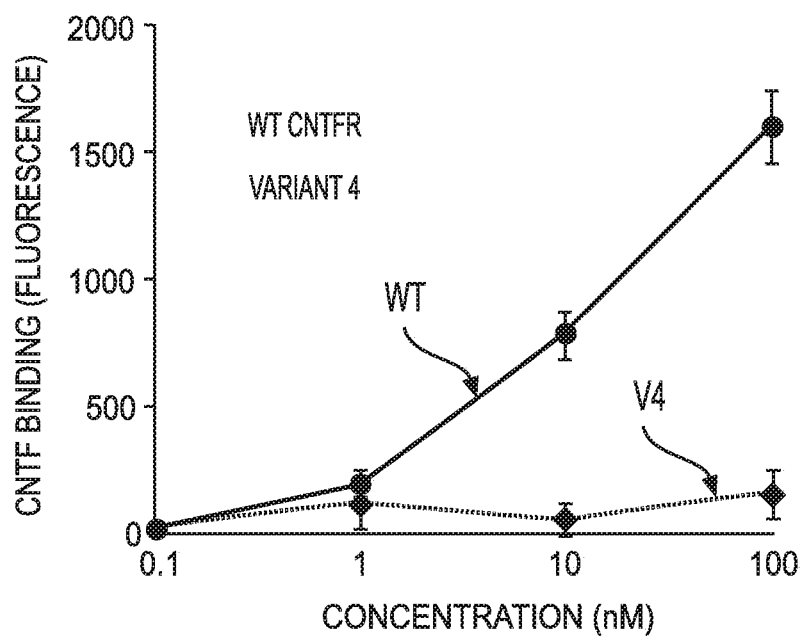
Figure 10D:
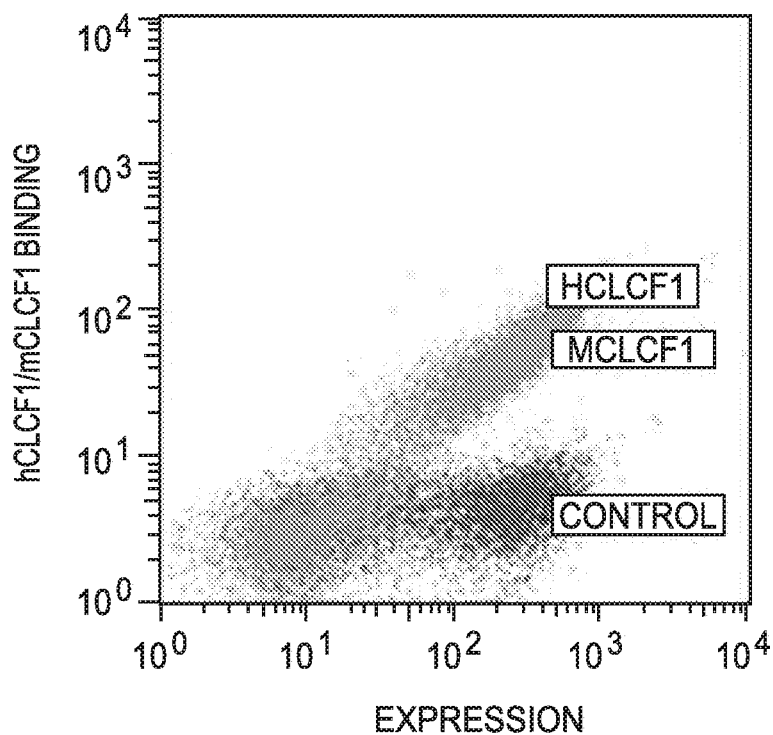

Qualitative yeast-displayed binding studies suggested that each of these mutations contributed to the binding affinity for CLCF1, and thus the clone (variant 4) containing all four mutations was chosen for further experiments (FIG. 10, panels A and B). Interestingly, while yeast displayed wild-type CNTFR bound to CNTF, variant 4 did not bind to CNTF indicating that the process of directed evolution led to increased specificity for CLCF1 (FIG. 10, panel C). Variant 4 still bound to mCLCF1 in addition to hCLCF1 (FIG. 10, panel D).

Figure 11:
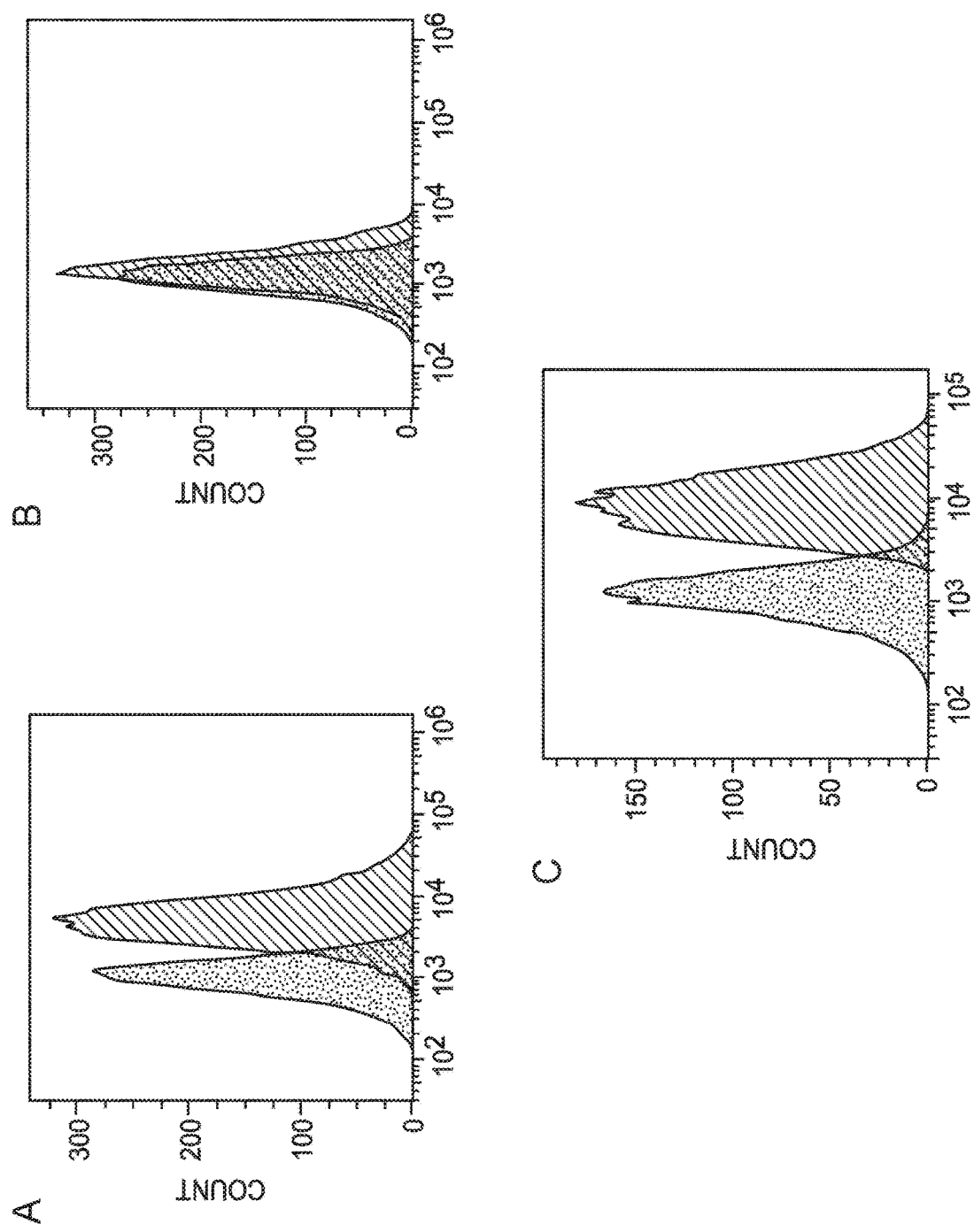
FIG. 11 A CNTFR variant containing T268A and D269A mutations binds to CLCF1 and LIFR, but not gp130. CNTFR T268A D269A construct binding signals to CLCF1 (panel A), gp130-Fc (panel B), and LIFR-Fc (panel C).
Figures 12A, 12B:
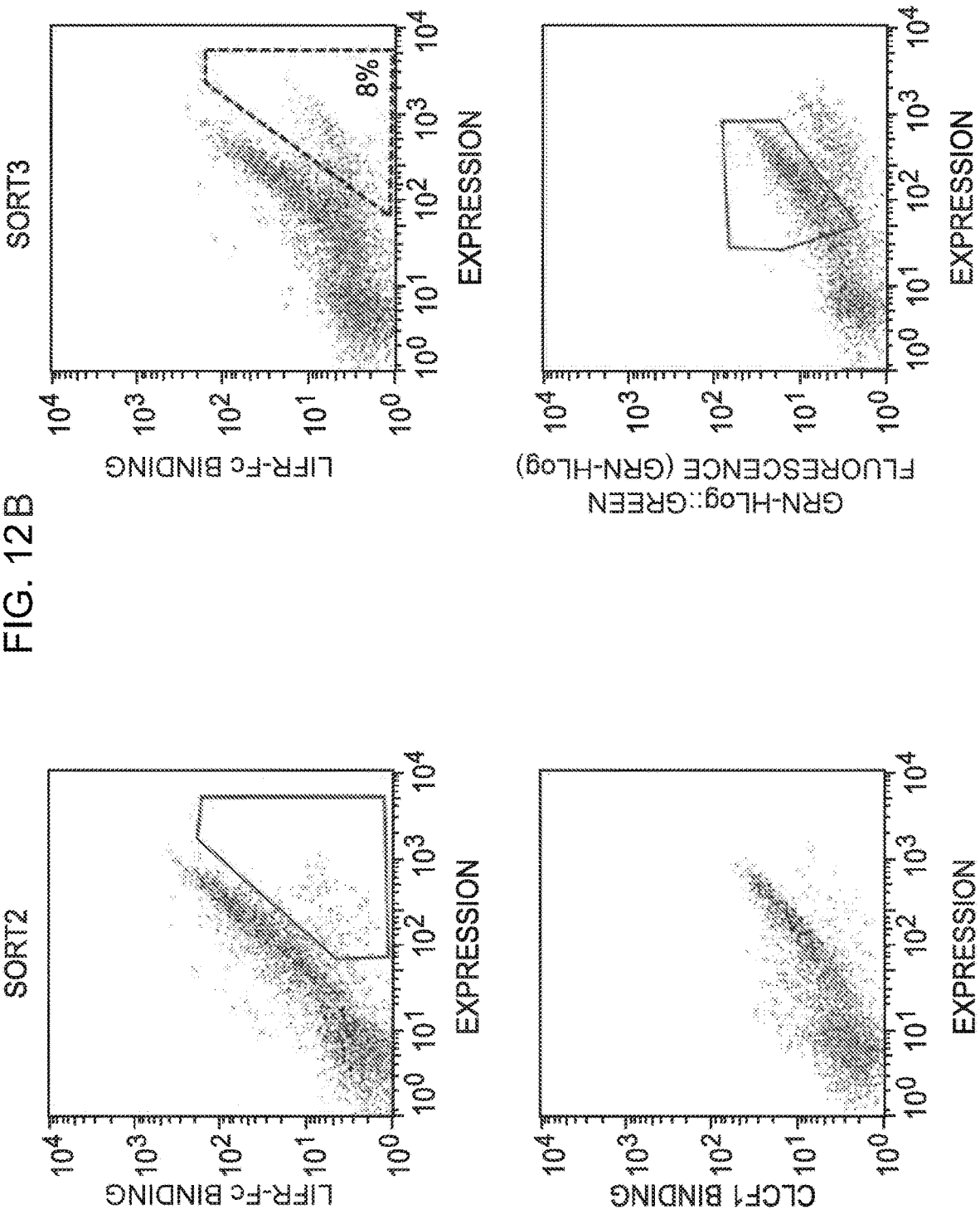
FIGS. 12A-12D Library screening for CNTFR variants that do not bind to LIFR. After the initial screening was carried out for high affinity CLCF1 binders, a population with low LIFR-Fc signal was isolated (panel A). This was followed by another screening for CLCF1 binders (panel C) and a screening for non-LIFR binders. Panel D: After 6 rounds of sorting the screened library shows decreased LIFR binding while it had unchanged CLCF1 binding. Gates in approximately the number that the term precedes. In determining whether a number is near to or approximately a specifically recited number, the near or approximating unrecited number may be a number which, in the context in which it is presented, provides the substantial equivalent of the specifically recited number.
Figure 12C:
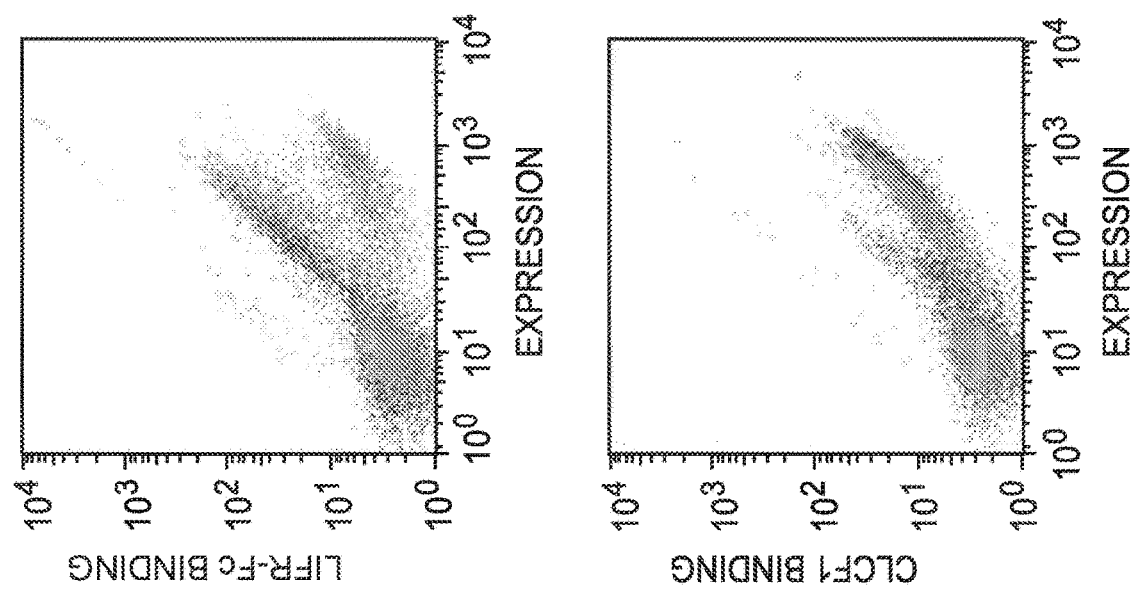
Figure 12D:
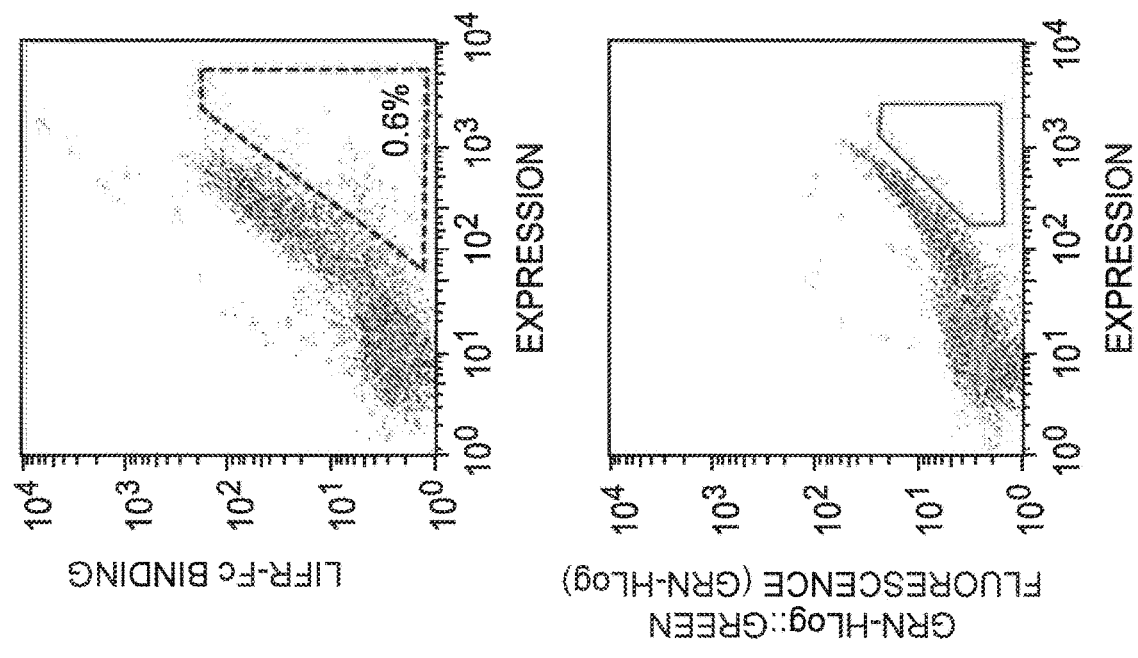
Figure 13:
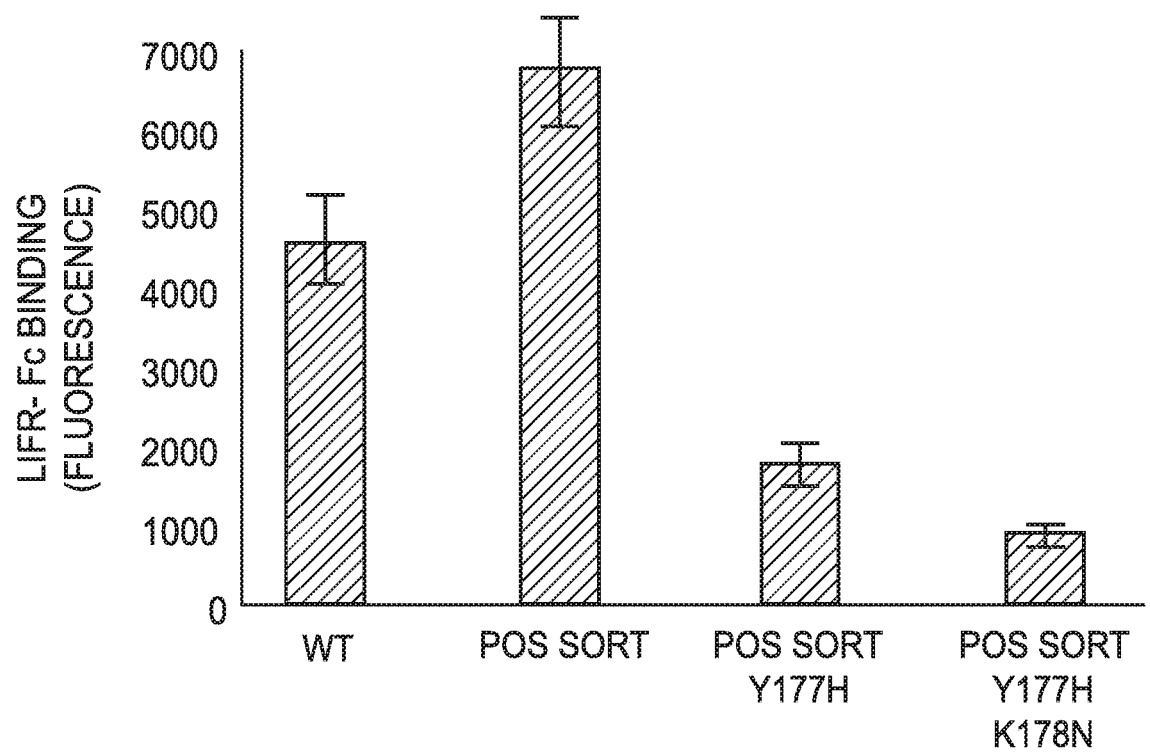

Example 7—Negative Screening of Affinity Matured CNTFR for Reduced Binding to LIFR Alanine substitutions at CNTFR amino acid residues 268 and 269 were previously shown to decrease CNTFR interaction with the beta receptors. When T268A and D269A were introduced into CNTFR displayed on the yeast cell surface, we discovered that these mutations reduced binding for gp130 but significant binding to LIFR remained (FIG. 11). Thus, to further engineer CNTFR to decrease its binding for LIFR, another random mutation using error-prone PCR introduced into variant 4 from FIG. 10, panel B. The resulting library was again displayed on yeast, but this time screened for the population that had decreased binding signal for LIFR in the presence of CLCF1. To retain the binding affinity for CLCF1, the screening was performed by alternating between positive selection for CLCF1 binding and negative selection for LIFR (FIG. 12). After six rounds of sorting, two consensus mutation emerged (Y177H and K178N) (FIG. 13, panel A). Because these mutations additively contributed to decreased LIFR binding a clone with both mutations (named eCNTFR) was chosen for further characterization. eCNTFR contains the four mutations that confer high affinity CLCF1 binding from variant 4, as well as the two new mutations that decrease binding to LIFR.

Example 8—Characterization of Soluble Engineered CNTFR

Figure 14:
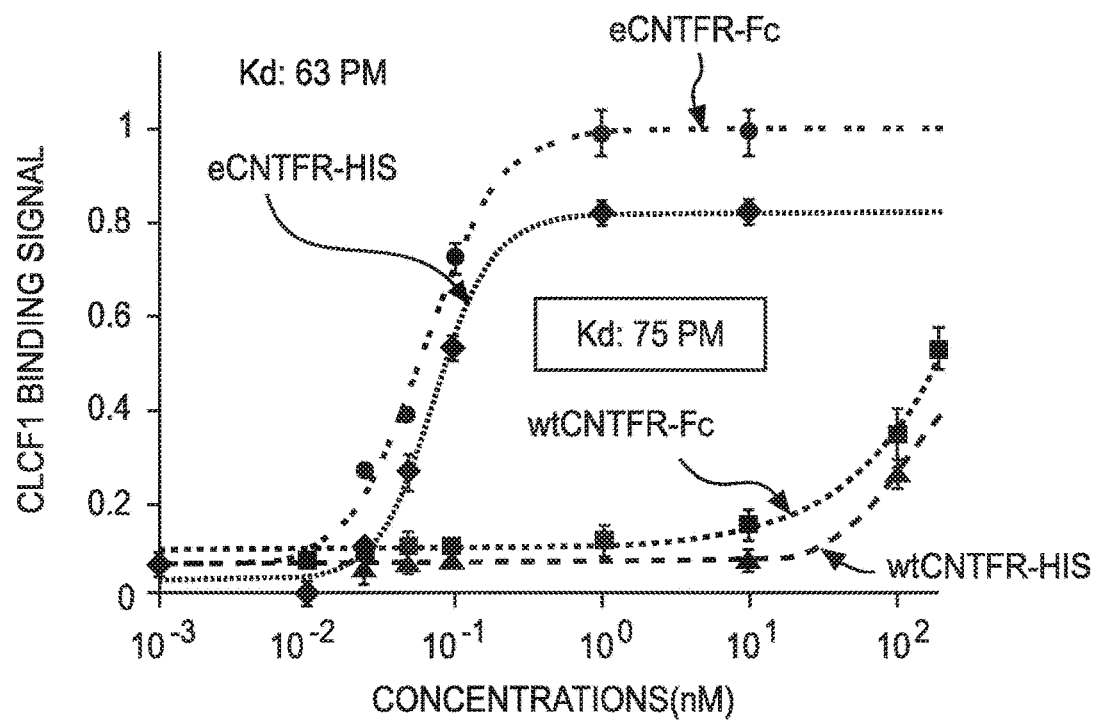
Figure 14:
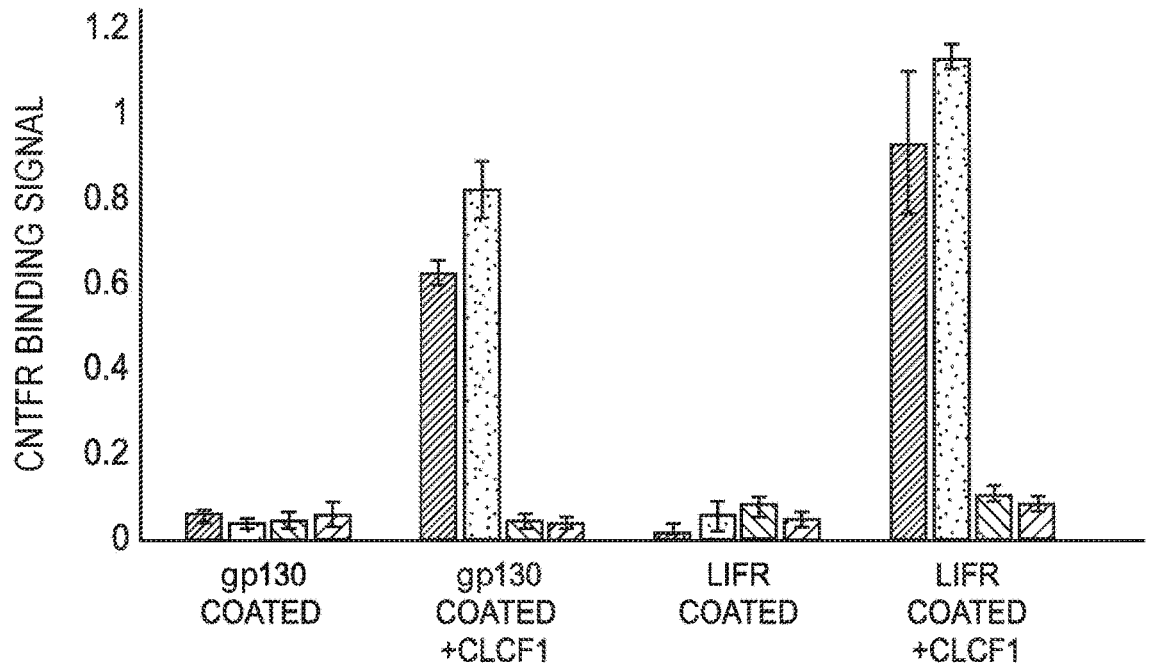

The eCNTFR variant was cloned into the Add2 mammalian expression vector and transfected into HEK293 cells to produce soluble constructs fused to His-tag and mouse IgG2a Fc. While wild-type CNTFR (wtCNTFR) yielded 8 milligrams per liter of cell culture, eCNTFR yielded 4 milligrams per liter. To measure the binding affinity of the soluble CNTFR constructs, they were first incubated with CLCF1 at room temperature for 4 hours. Then the complexes were captured using microtiter plates coated with anti-his antibody or anti-mouse Fc antibody. Using a rabbit anti-CLCF1 primary antibody, followed by an HRP tagged anti-rabbit secondary antibody, a binding interaction between CLCF1 and soluble CNTFR was able to be measured. Both His tagged and Fc fusion eCNTFR showed picomolar binding affinity to CLCF1 (FIG. 14, panel B). In comparison, the CLCF1 binding affinity was too weak to be quantified for wtCNTFR. The same approach was used to characterize binding interaction with the beta receptors. In these experiments, eCNTFR-His and eCNTFR-Fc showed no detectable binding signal to gp130 and LIFR, unlike wtCNTFR which bound both receptors (FIG. 13, panel B). These results were consistent with the results observed from the yeast-displayed constructs. Because increasing the size of a small protein to avoid glomerular filtration can significantly increase serum half-life, we chose eCNTFR-Fc, fused to mouse IgG2a Fc domain, for evaluating downstream effects of CLCF1 inhibition. This Fc fusion would also benefit from FcRn-mediated recycling for half-life extension in vivo.

The amino acid sequence of the example soluble CNTFR polypeptide-Fc fusion ("eCNTFR-Fc"—SEQ ID NO:4) is set forth in Table 4 below. In this example, the soluble CNTFR polypeptide of SEQ ID NO:2 is fused to a full-length mouse Fc region (underlined in Table 4).

TABLE 4

| Amino Acid Sequence of an Example Soluble CNTFR Polypeptide-Fc Fusion | |
|---|---|
| | Amino Acid Sequence |
| Example Soluble CNTFR Polypeptide (SEQ ID NO: 4) (R110Q, T174P, Y177H, K178N, S237F, T268A, D269A, I287F) | MAAPVPWACCAVLAAAAAVVYAQRHSPQEAPHVQYERLGSDVTLPCGTA NWDAAVTWRVNGTDLAPDLLNGSQLVLHGLELGHSGLYACFHRDSWHLR HQVLLHVGLPPQEPVLSCRSNTYPKGFYCSWHLPTPTYIPNTFNVTVLH GSKIMVCEKDPALKNRCHIRYMHLFSPIKHNVSISVSNALGHNATAITF DEFTIVKPDPPENVVARPVPSNPRRLEVTWQTPSTWPDPEFFPLKFFLR YRPLILDQWQHVELSDGTAHTIAAAYAGKEYIIQVAAKDNEFGTWSDWS VAAHATPWTEEPRHLTTEAQAAETTTSTTSSLAPPPTTKICDPGELGS<u>R RLEPRGPTIKPCPPCKCPAPNLLGGPSVFIFPPKIKDVLMISLSPIVTC VVVDVSEDDPDVQISWFVNNVEVHTAQTQTHREDYNSTLRVVSALPIQH QDWMSGKEFKCKVNNKDLPAPIERTISKPKGSVRAPQVYVLPPPEEEMT KKQVTLTCMVTDFMPEDIYVEWTNNGKTELNYKNTEPVLDSDGSYFMYS KLRVEKKNWVERNSYSCSVVHEGLHNHHTTKSFSRTPGK</u> |

Example 9—eCNTFR-Fc Inhibits STAT3 Activation in Human NSCLC Cells

Figure 15A:
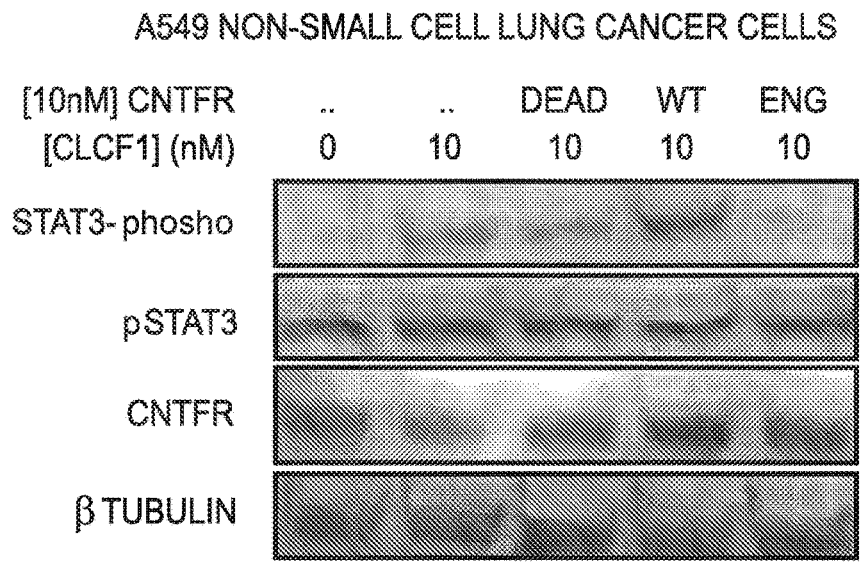
Figure 15B:
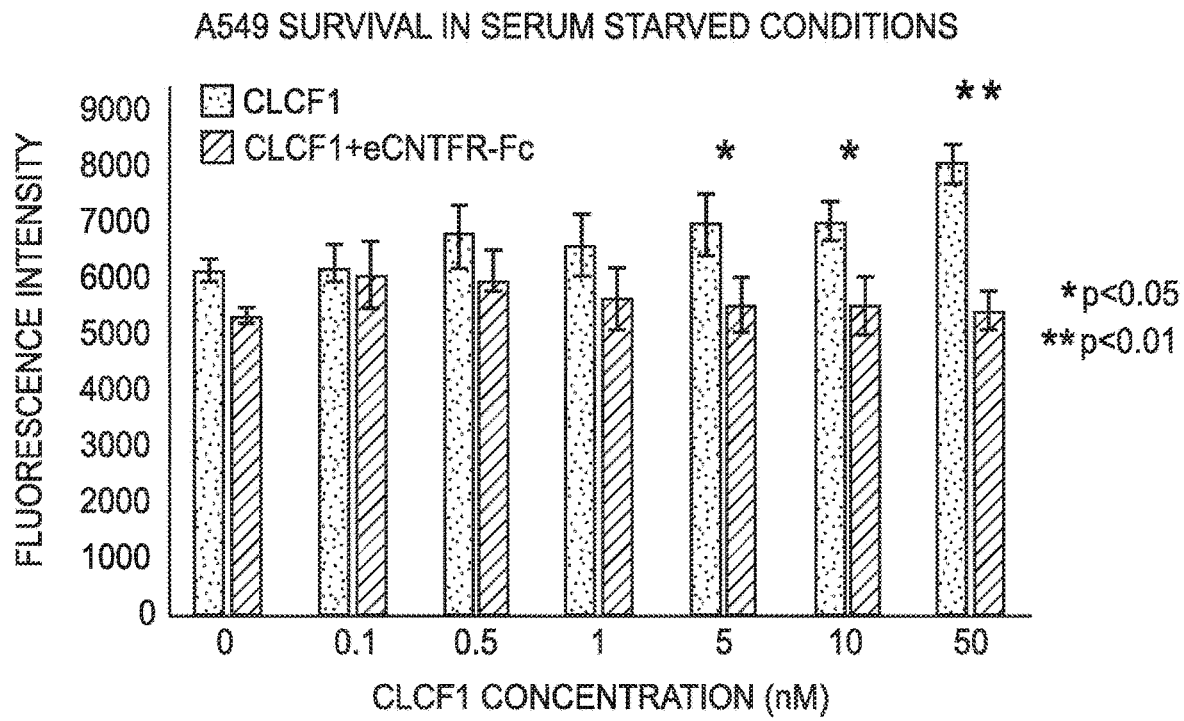
Figure 15C:
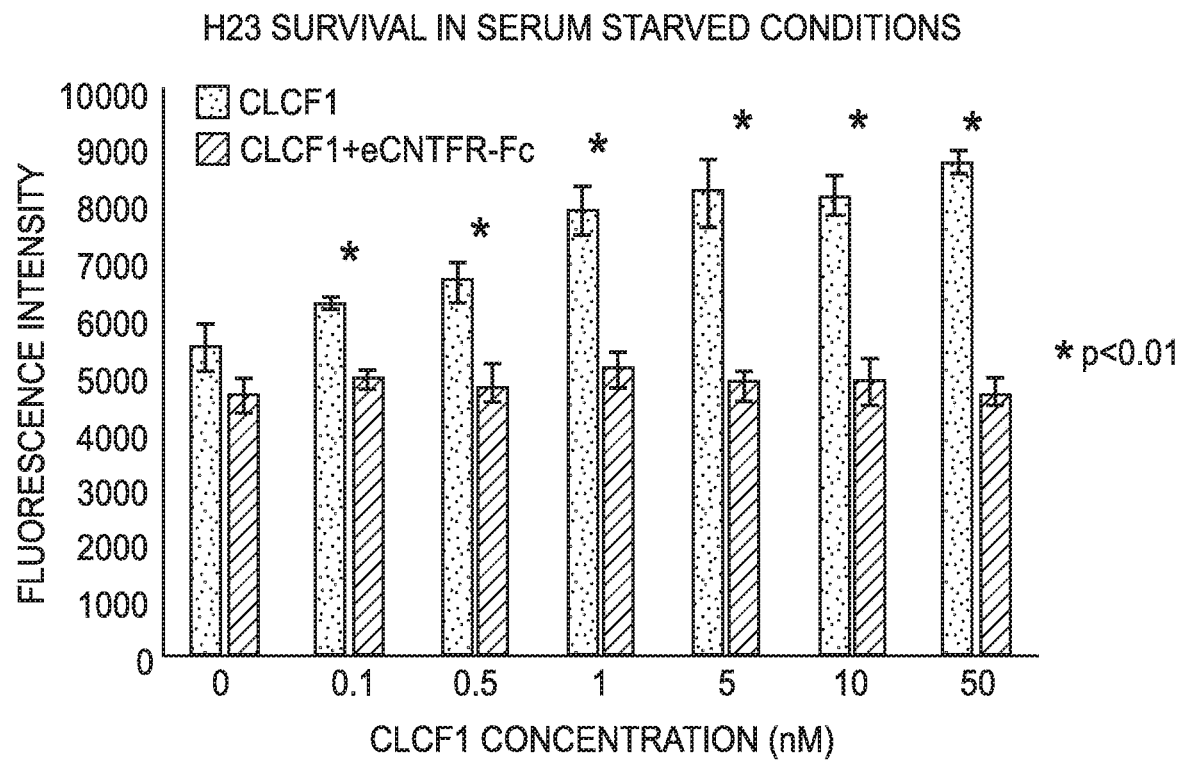

To determine whether eCNTFR-Fc could effectively neutralize CLCF1 and inhibit STAT3 phosphorylation we tested its effect on two human NSCLC cell lines, A549 and H23. The cells were stimulated with CLCF1 in the presence and absence of the soluble CNTFR constructs. Strikingly, wtCNTFR-Fc increased phosphorylation of STAT3 (Tyr705) while treatment with eCNTFR-Fc effectively decreased the STAT3 phosphorylation (FIG. 15, panel A). Furthermore, incubation with eCNTFR-Fc inhibited CLCF1-mediated cell survival in serum starved conditions in both A549 and H23 cells (FIG. 15, panels B and C, respectively).

Example 10—eCNTFR-Fc Decreases Tumor Growth in Mouse Xenograft Models

Figure 16A:
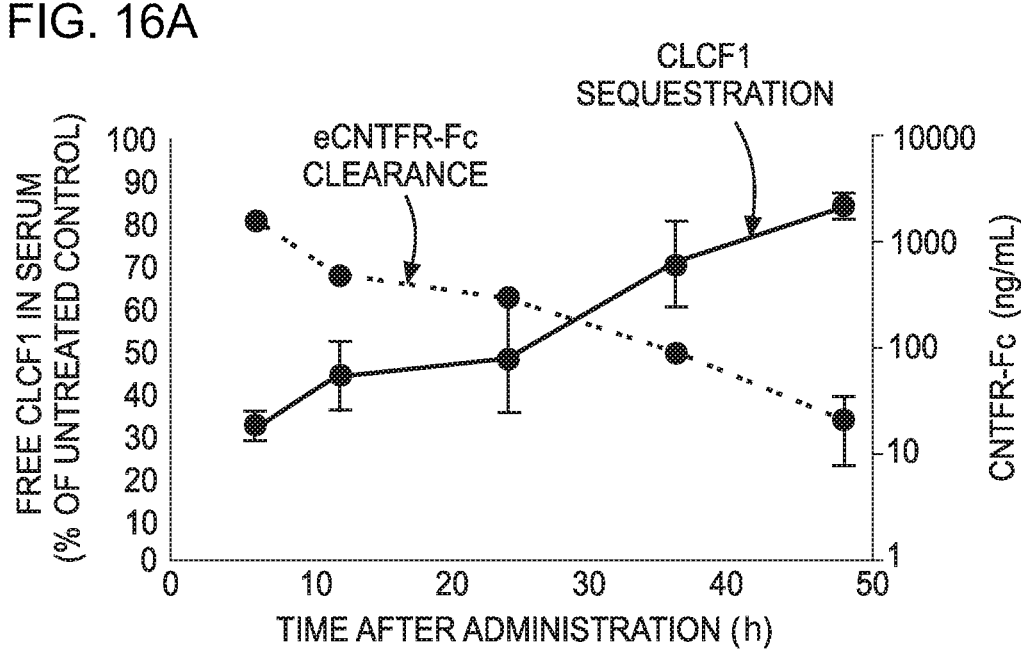
Figure 16B:
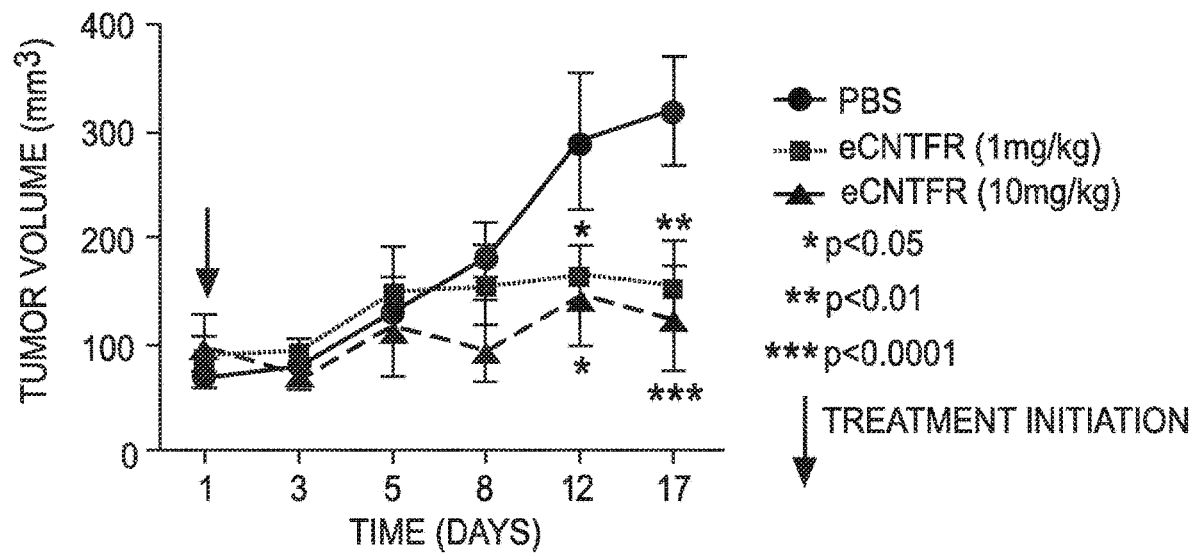
Figure 16C:
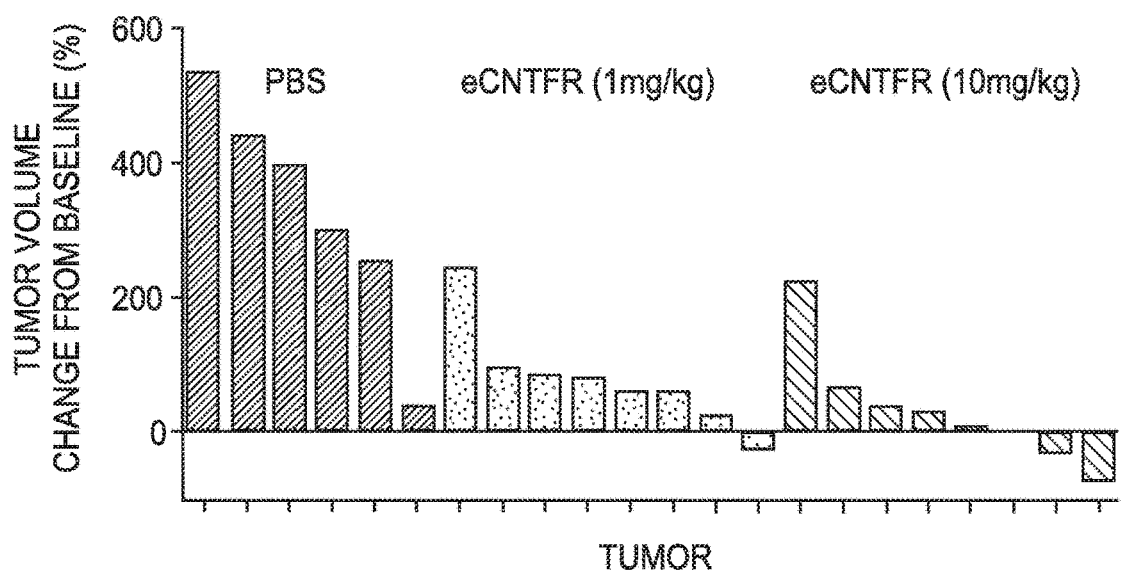

Next, we tested whether eCNTFR-Fc retained its ability to sequester CLCF1 and decrease tumor growth in vivo. Non-tumor bearing mice were given a single dose of eCNTFR-Fc at 1 mg/kg body weight and the amount of unbound CLCF1 in the serum at different time points was measured with ELISA using eCNTFR-Fc as a capturing agent. Serum samples were collected and analyzed 6, 12, 24, 36, and 48 hours after injection. Serum CLCF1 was rapidly sequestered by injected eCNTFR-Fc, but after 48 h CLCF1 levels approached the untreated baseline (FIG. 16, panel A). Starting from 6 h after injection the measured eCNTFR-Fc level decreased with the estimated half-life of around 48 h, which correlated with the sequestration of serum CLCF1.

To test whether eCNTFR-Fc could affect tumor growth in vivo, two different models of non-small cell lung cancer were treated with eCNTFR-Fc. In the first model, A549 cells were subcutaneously injected and grown on two opposing flanks of each mouse. After the tumor sizes grew to approximately 100 mm$^3$ the mice were injected with 10 mg/kg or 1 mg/kg body weight or saline control, twice weekly for 4 weeks. Treatment with both concentrations of eCNTFR-Fc significantly decreased tumor growth after 17 days of treatment compared with saline control (FIG. 16, panels B and C).

Figure 17:
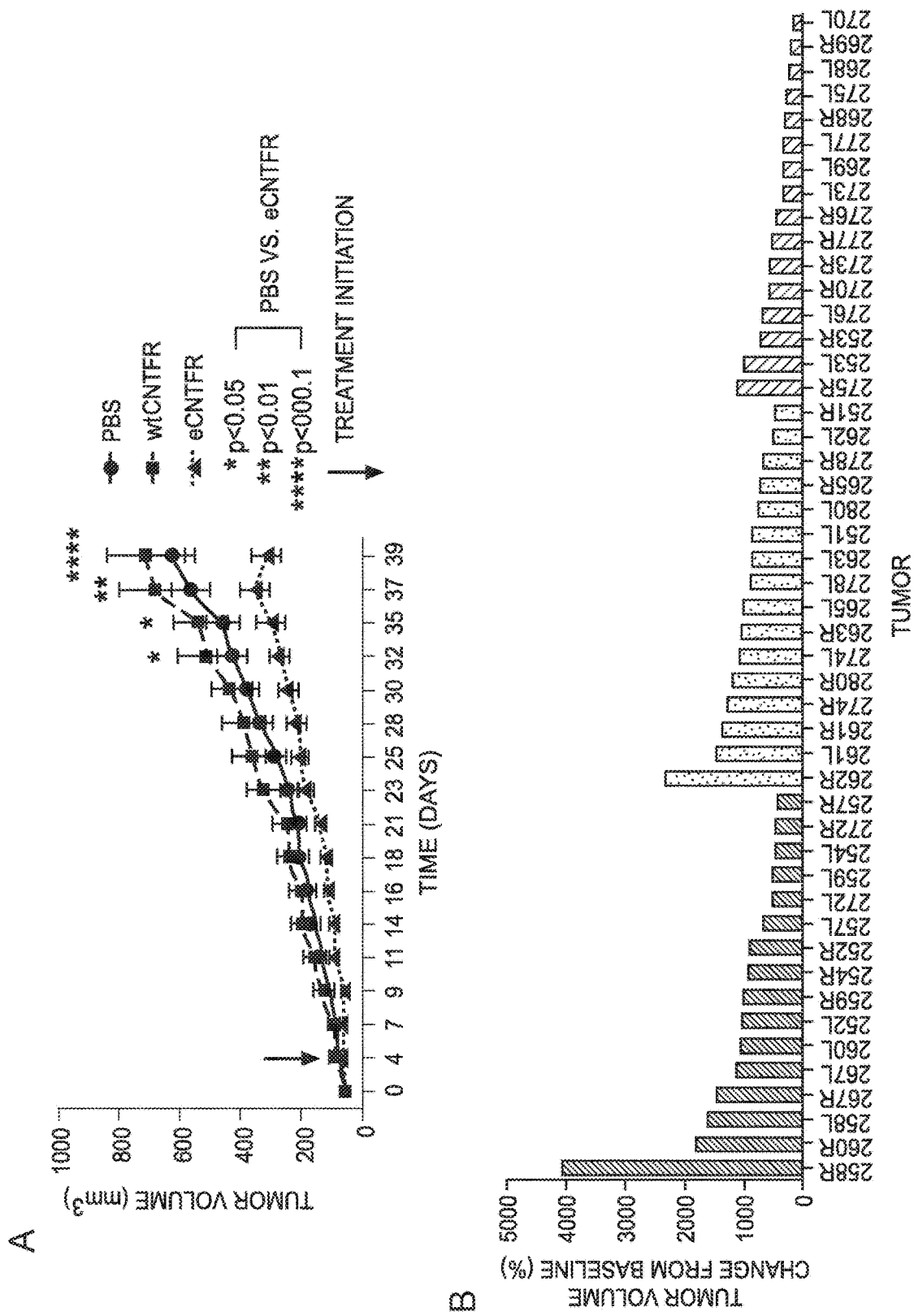

Another experiment was conducted in a similar manner, using a xenograft model with H23 cells. This time, eCNTFR-Fc treatment at 10 mg/kg was compared with wtCNTFR-Fc treatment and saline control, and injection frequency was increased to three times per week for 39 days. Similar results were observed, where eCNTFR-Fc decreased the tumor volume significantly by the end of the study while wtCNTFR-Fc seemed to slightly increase the tumor size although these results were statistically insignificant (FIG. 17).

Example 11—Specificity in Engineered CLCF1 Trap (eCNTFR)

Figure 18:
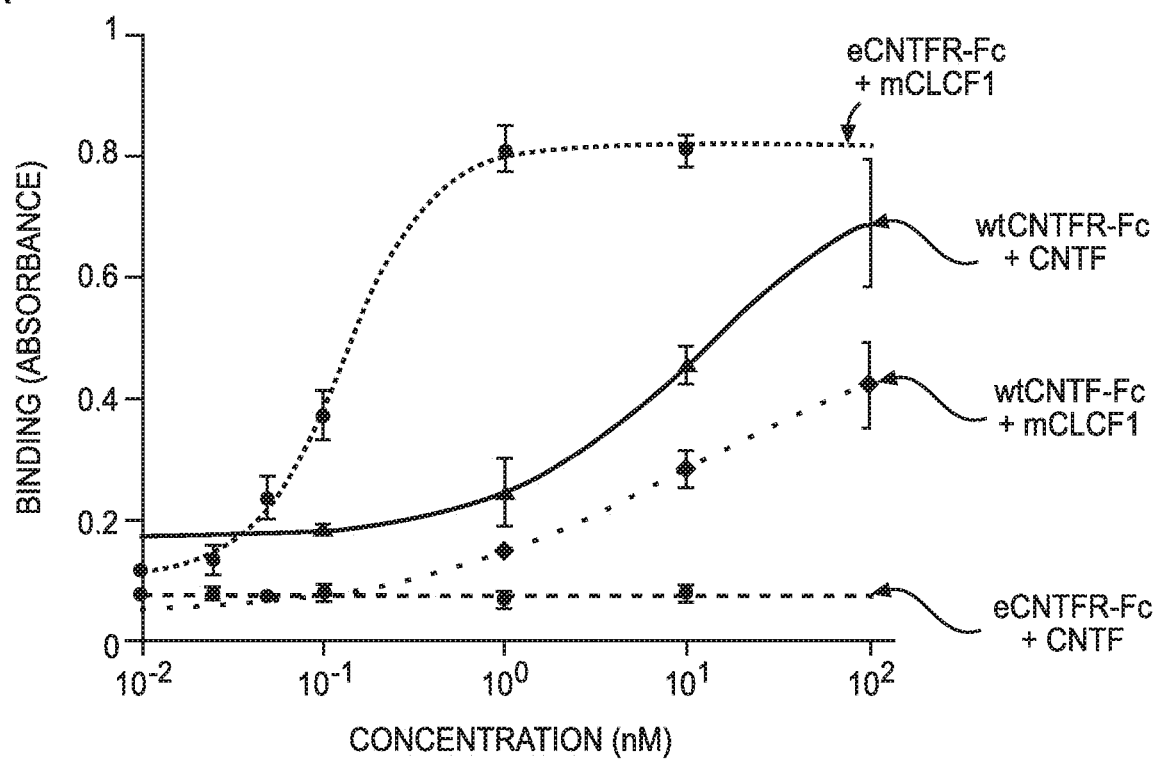
Figure 18:
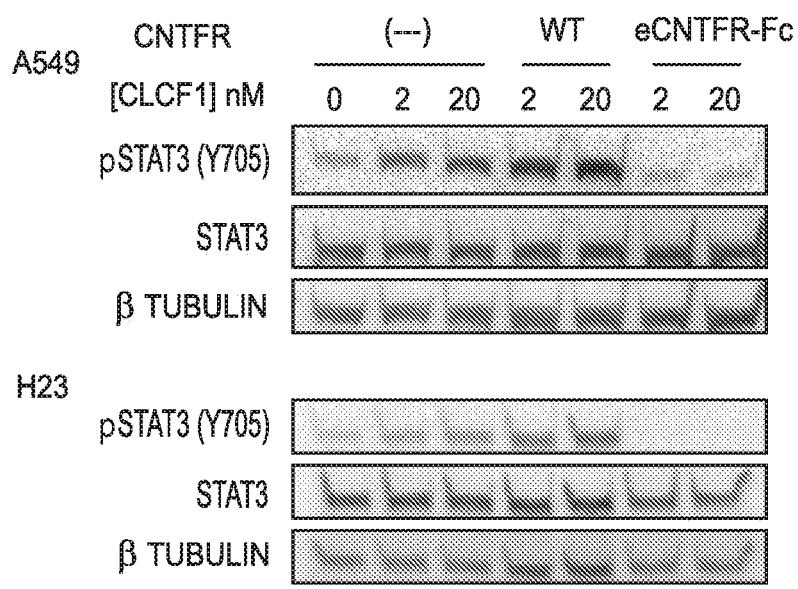
Figure 19A:
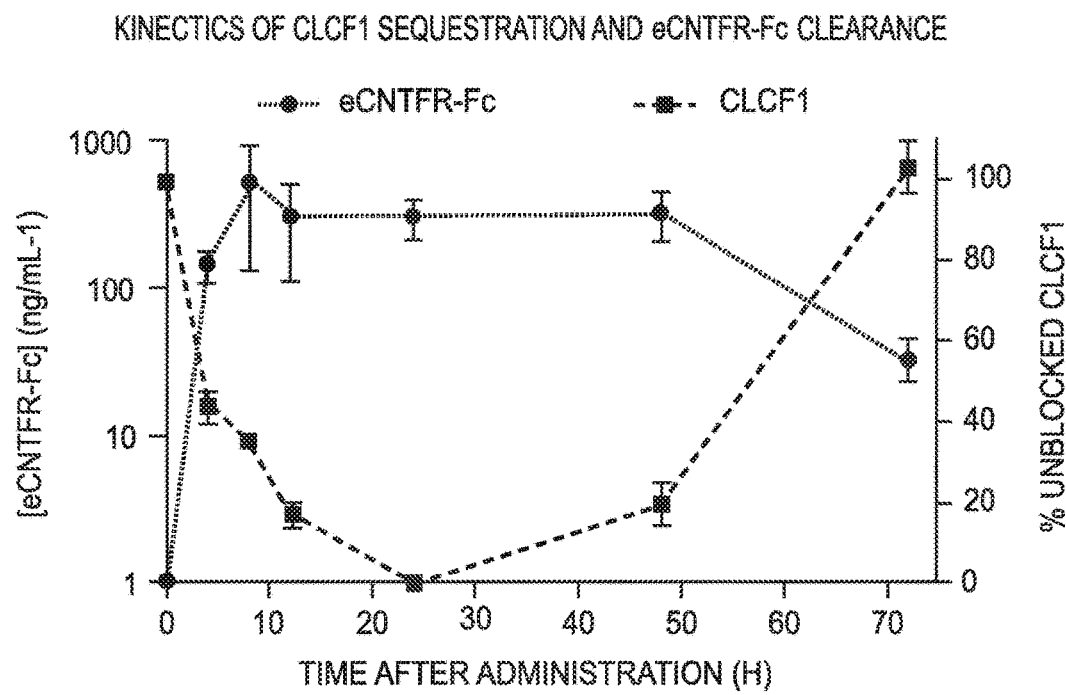
Figure 19B:
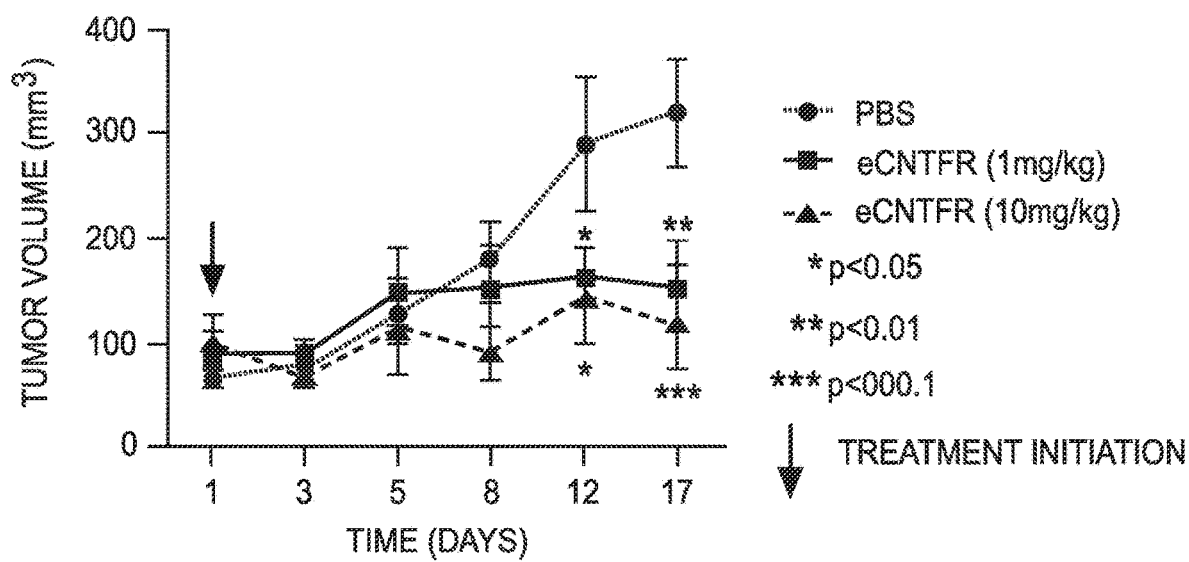
Figure 19C:
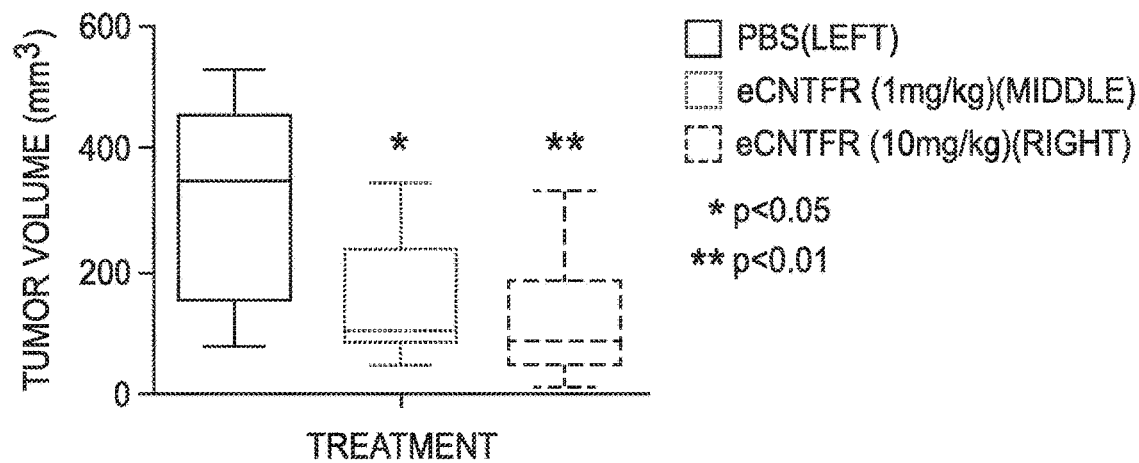
Figure 19D:
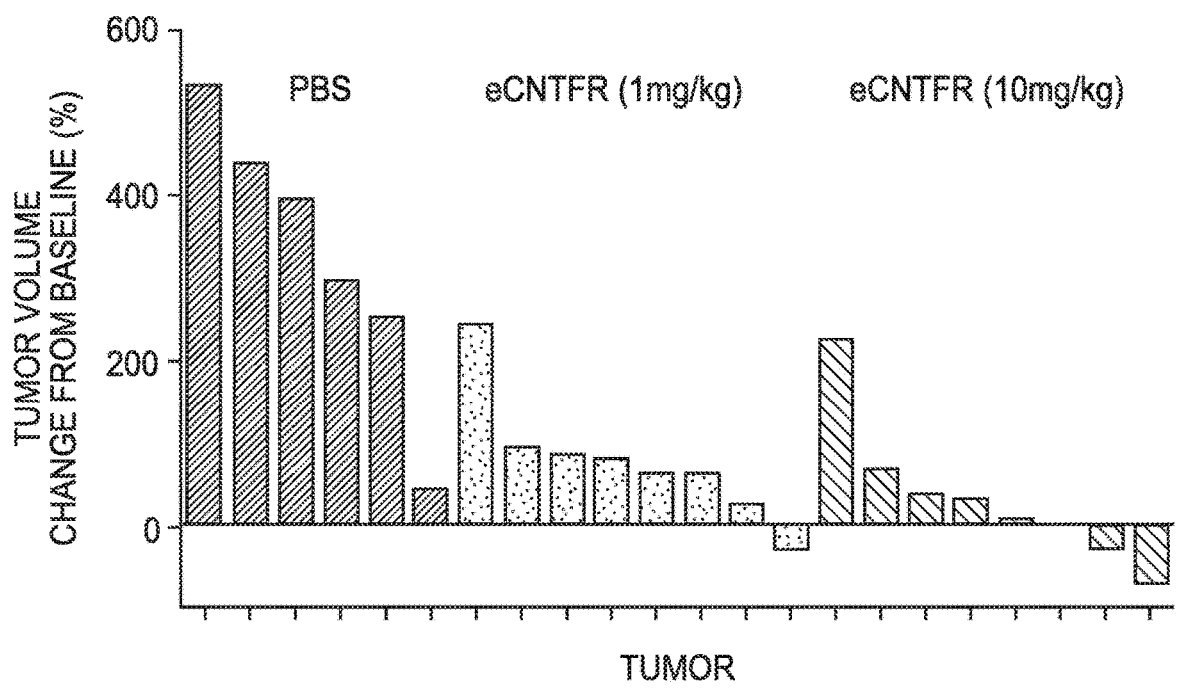
Figure 19E:
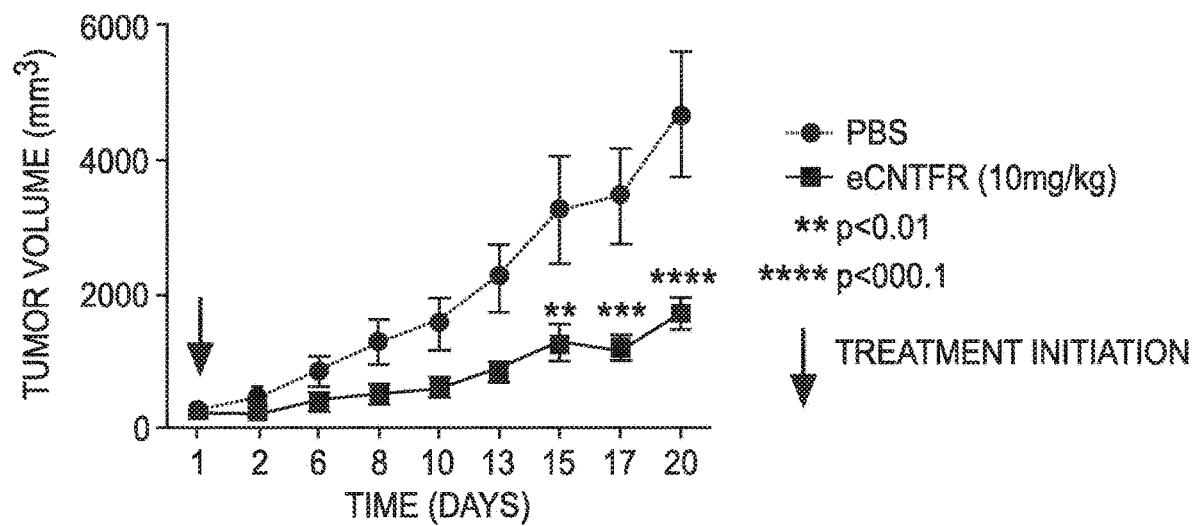
Figure 19F:
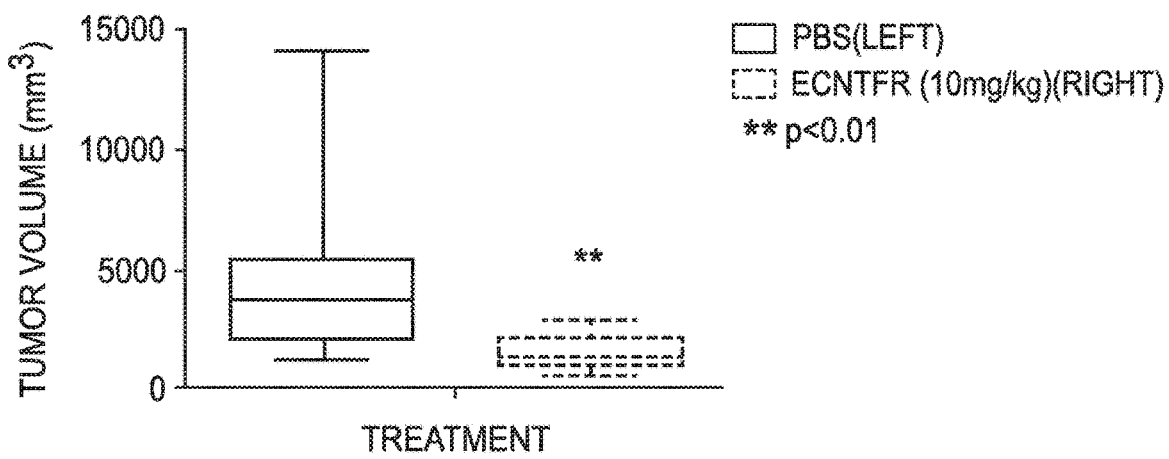
Figures 19G, 19H:
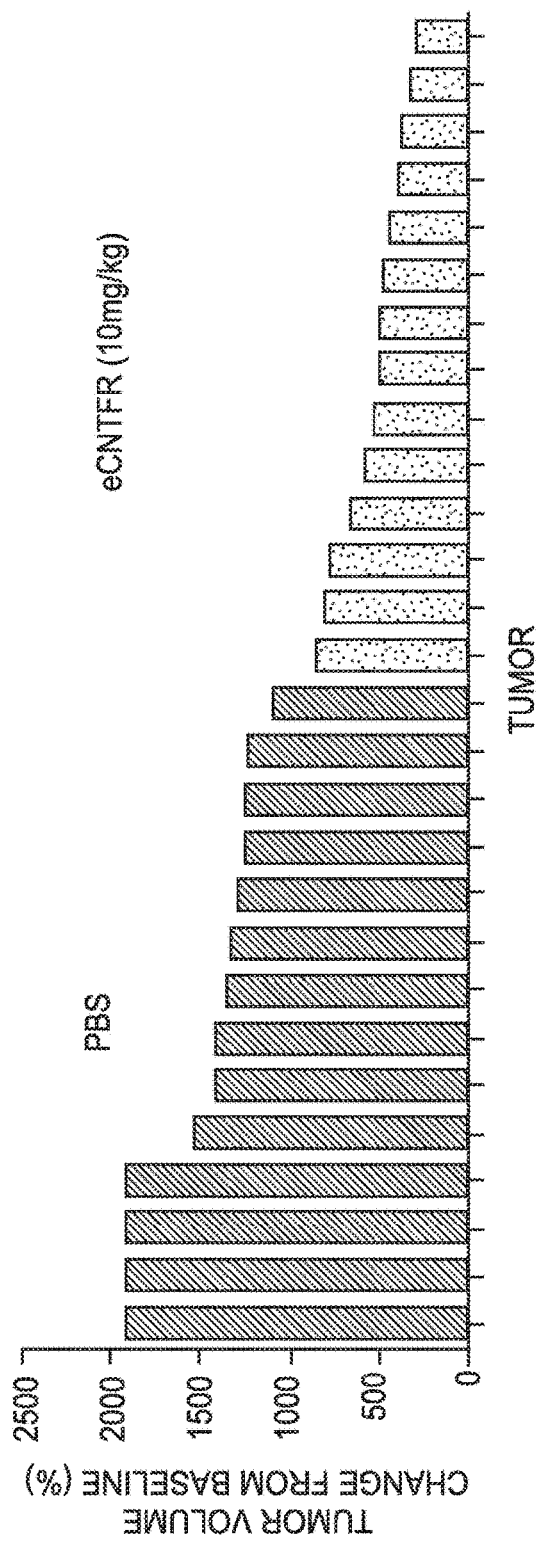
Figure 19I:
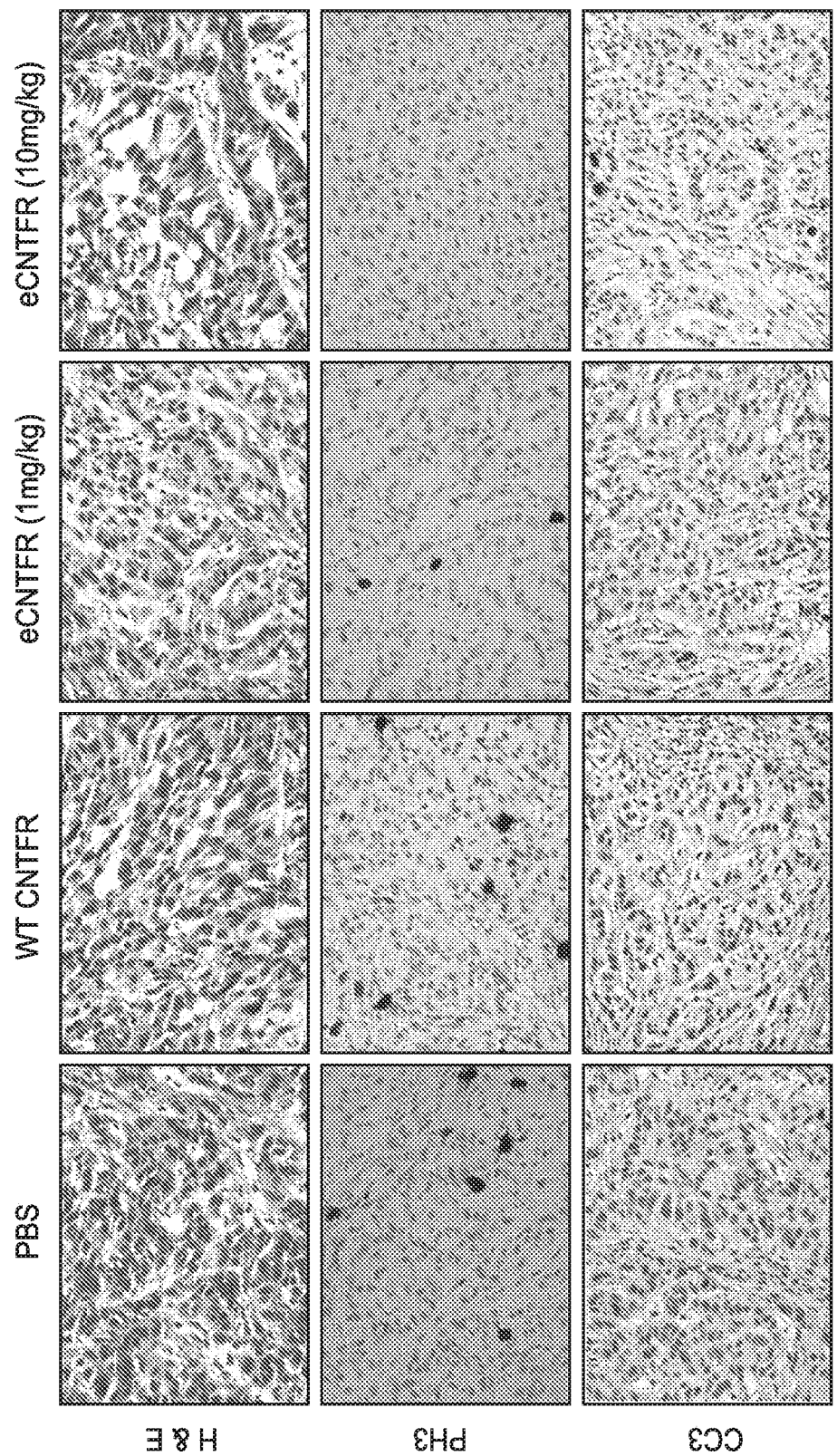
Figure 19I:
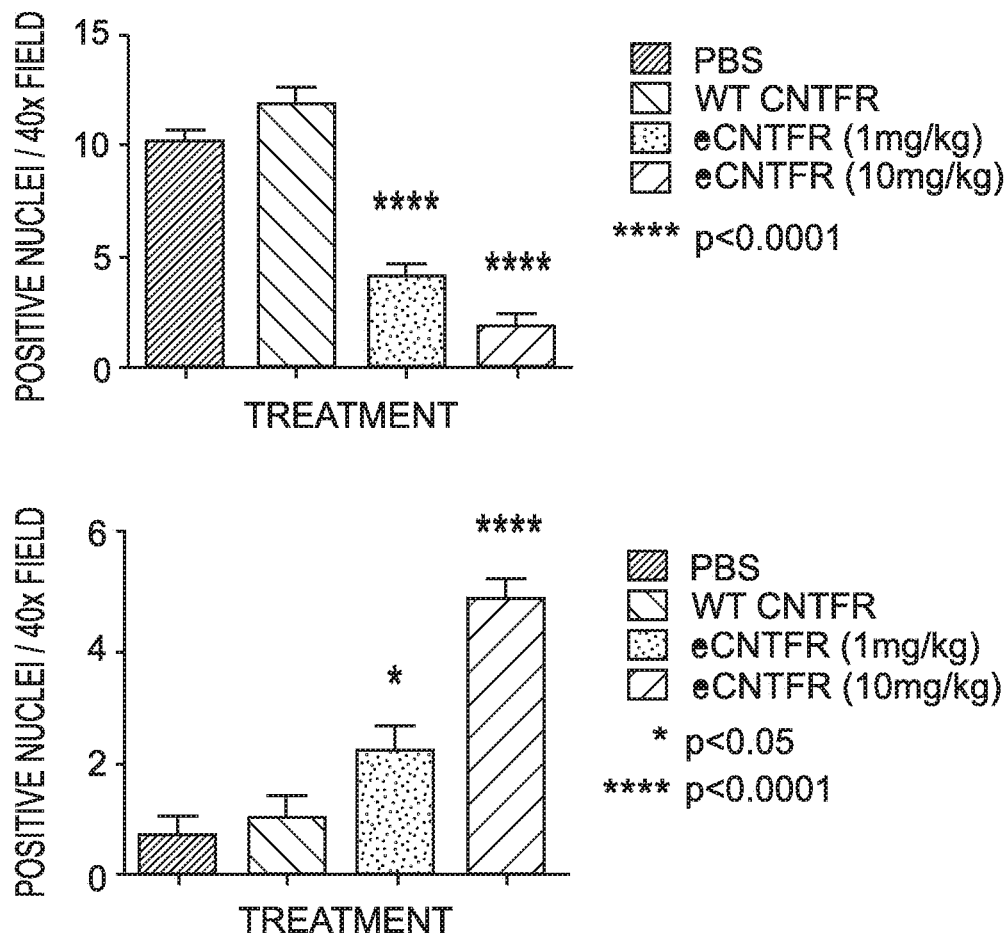
Figure 20A:
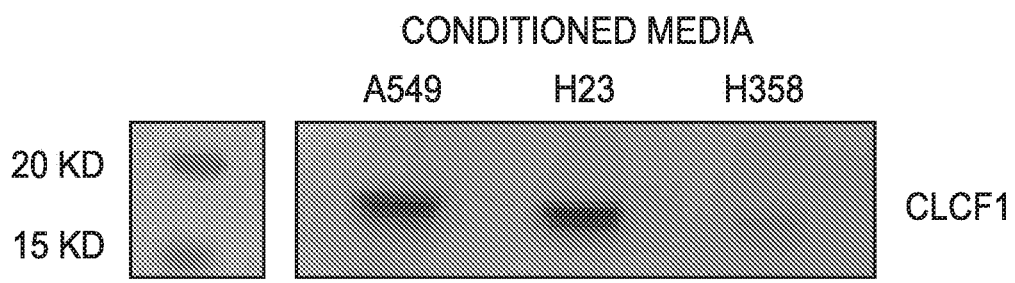
Figure 20B:
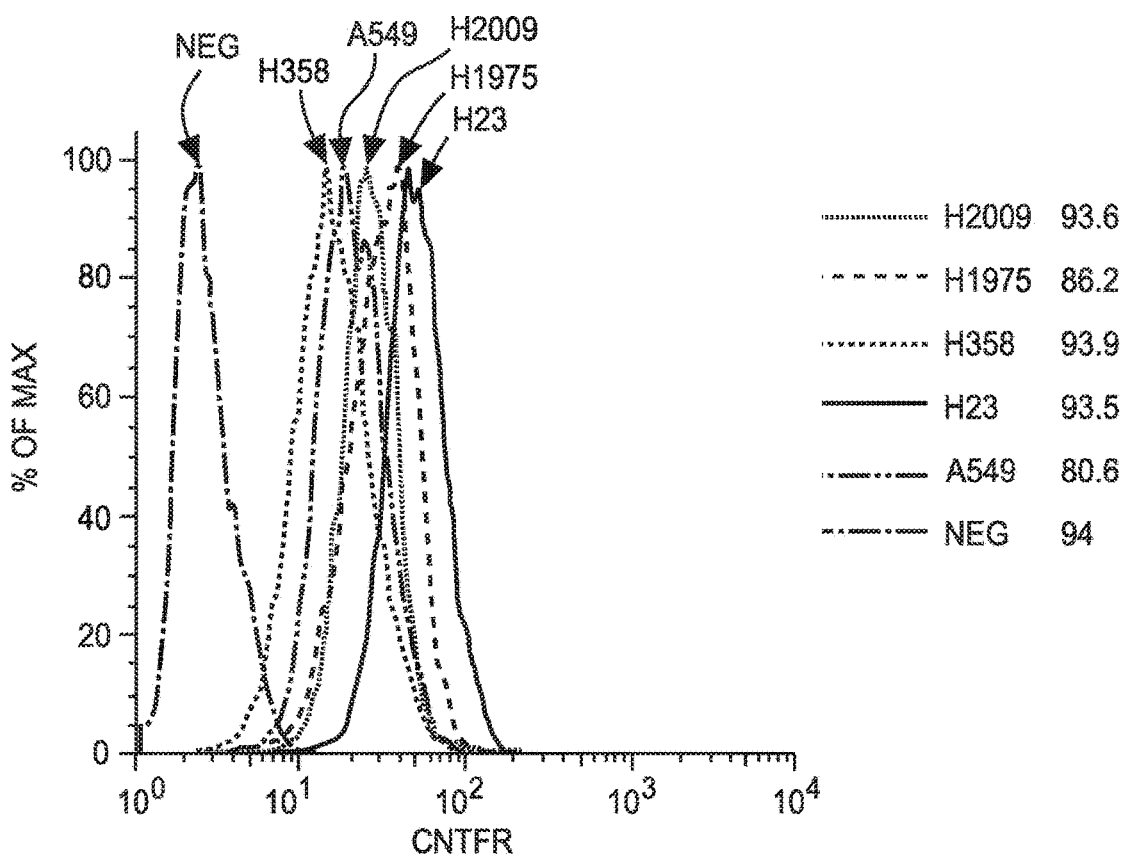
Figure 20C:
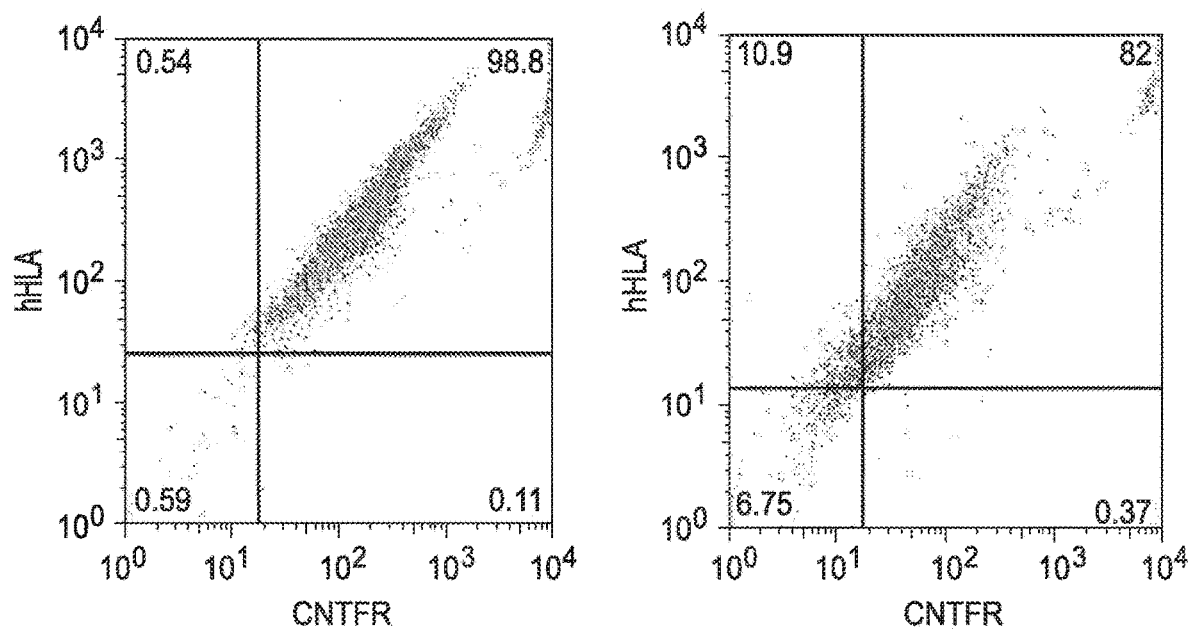
Figure 20D:
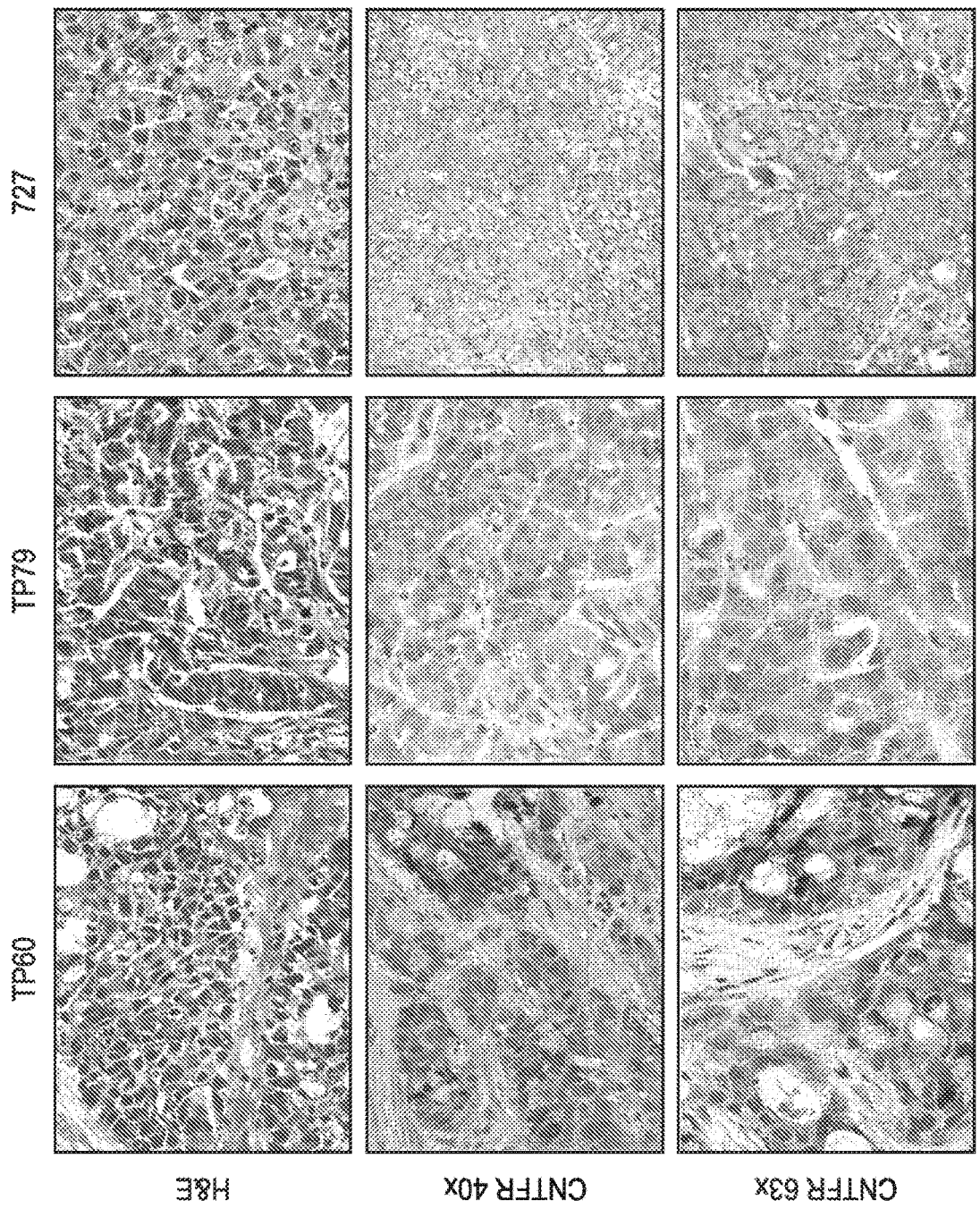

CNTF (ciliary neurotrophic factor) is another ligand for CNTFR that shares with CLCF1 the ligand binding motif of CNTFR. Since CNTF-mediated signaling is important for neuronal cell survival and may have cytoprotective effects induced by injury, binding affinity of eCNTFR-Fc to CLCF1 over CNTF can be favorable for preventing side effects from inhibiting CNTF. When the binding affinity of eCNTFR-Fc for recombinantly produced CNTF was measured using ELISA, while wtCNTFR-Fc demonstrated substantial binding for CNTF, eCNTFR-Fc lost its affinity for CNTF in the tested concentrations. On the other hand, eCNTFR-Fc showed high affinity for mouse CLCF1 (mCLCF1), which may be critical for in vivo mouse model experiments since mouse CLCF1 can phosphorylate STAT3 in human cells. Data is shown in FIG. 18, panel A.

To determine whether eCNTFR-Fc could effectively neutralize CLCF1 and inhibit STAT3 phosphorylation, its effect was tested on two human NSCLC cell lines: A549 and H23. The cells were stimulated with CLCF1 in the presence and absence of soluble CNTFR constructs. While wtCNTFR-Fc increased phosphorylation of STAT3 (Tyr705), eCNTFR-Fc effectively decreased the phosphorylation in both cell lines. Data is shown in FIG. 18, panel B.

Example 12—Pharmacokinetics of CLCF1 Sequestration and eCNTFR-Fc Clearance

To test whether eCNTFR-Fc retained its ability to sequester CLCF1 in vivo, blood clearance and CLCF1 sequestration after intraperitoneal (i.p.) dosing of 10 mg/kg eCNTFR-Fc in NOD/SCID/gamma mice were quantified. Serum samples were collected post injection and unbound CLCF1 (squares) was measured by ELISA using eCNTFR-Fc as the capturing agent. Vehicle treated mice were used to determined baseline CLCF1 levels. eCNTFR-Fc levels (circles) in the blood were quantified by ELISA using an anti-Fc antibody as the capturing agent. Serum CLCF1 was rapidly sequestered by injected eCNTFR-Fc, however, at 72 hours, CLCF1 levels approached the untreated baseline. (FIG. 19, panel A). These data demonstrate that eCNTFR-Fc effectively binds to mouse CLCF1 and suggest that any significant toxicities in vivo should be observable in mice.

Example 13—eCNTFR-Fc Inhibits In Vivo Tumor Growth

To test the pharmacological efficacy of eCNTFR in vivo, NSCLC cell lines were engrafted in immunodeficient mice. Primary tumors were allowed to grow to an approximate size of 100-150 mm3. Initially, mice were randomized into one of four groups: vehicle (PBS), wildtype CNTFR (wtCNTFR-Fc), a low dose (1 mg/kg) of eCNTFR-Fc, and a high dose (10 mg/kg) of eCNTFR-Fc (FIG. 21, panel B). Mice were injected twice per week by intraperitoneal (i.p.) injection for 18 days. Administration of eCNTFR-Fc demonstrated dose-dependent tumor inhibition (FIG. 19, panels B-D). Comparable effects were observed in a second NSCLC cell line.

Increasing evidence suggests that PDTXs faithfully recapitulate human tumor biology and predict responses to therapy. PDTXs obtained by direct implants of surgically resected tumors from humans into mice are known to maintain morphological similarities and recapitulate molecular profiles of the original tumors. As such, to validate our findings in a clinically relevant setting, we generated NSCLC PDTX models to test eCNTFR-Fc. One LUAD PDTX model showed significant tumor growth inhibition upon eCNTFR-Fc treatment three times per week by i.p. injection for three weeks or until control (PBS) mice showed signs of morbidity (FIG. 19, panels E-H).

In each xenograft model, proliferation and apoptosis in response to eCNTFR were assayed by PH3 and CC3 immunostaining, respectively. A significant decrease in proliferation and an increase in apoptosis was observed after treatment with eCNTFR-Fc (FIG. 19, panel I). In the lower left and right bar graphs in panel I, the results for PBS, WT CNTFR, eCNTFR (1 mg/kg), and eCNTFR (10 mg/kg), are provided from left to right. Taken together, these results indicate that disruption of CLCF1-induced signaling in tumor cells can be effectively achieved using eCNTFR.

Example 15—Expression of CLCF1 and CNTFR in Lung Cancer

While cancer-associated fibroblasts (CAFs) express CLCF1 and may be the source for this cytokine in vivo, the present study determined that NSCLC cell lines also secrete CLCF1, suggesting the existence of both paracrine and autocrine signaling mechanisms for this cytokine (FIG. 20, panel A). The receptor for CLCF1, CNTFR, was also determined to be expressed on all NSCLC cell lines and patient-derived xenograft (PDTX) models tested (FIG. 20, panels B and C). Expression of CNTFR was also observed by immunohistochemistry in PDTX models and in tumors generated in the KrasG12D;P53f/f genetically-engineered mouse model (FIG. 20, panel D). Taken together these results suggest that the CLCF1-CNTFR signaling axis is active in lung adenocarcinoma and that it may have a role in oncogenesis, particularly in tumors driven by oncogenic Kras.

Notwithstanding the appended claims, the disclosure is also defined by the following clauses:

1. A pharmaceutical composition, comprising:
an agent that specifically binds a ligand of ciliary neurotrophic factor receptor (CNTFR); and
a pharmaceutically acceptable carrier.
2. The pharmaceutical composition of Clause 1, wherein the agent that specifically binds a ligand of CNTFR specifically binds a ligand selected from the group consisting of: ciliary neurotrophic factor (CNTF), cardiotrophin-like cytokine factor 1 (CLCF1), neuropoetin (NP), and any combination thereof.
3. The pharmaceutical composition of Clause 1 or Clause 2, wherein the agent that specifically binds a ligand of CNTFR is a soluble CNTFR polypeptide.
4. The pharmaceutical composition of Clause 3, wherein the soluble CNTFR polypeptide comprises a mutation that reduces binding affinity of the soluble CNTFR polypeptide for a ligand-CNTFR complex subunit relative to a wild-type CNTFR polypeptide.
5. The pharmaceutical composition of Clause 4, wherein the ligand-CNTFR complex subunit is glycoprotein 130 (gp130), leukemia inhibitory factor receptor (LIFR), or both.
6. The pharmaceutical composition of Clause 5, wherein the ligand-CNTFR complex subunit is LIFR.
7. The pharmaceutical composition of Clause 6, wherein the mutation that reduces binding affinity for LIFR is at amino acid position 177, 178, or both, relative to a CNTFR polypeptide having the amino acid sequence set forth in SEQ ID NO:1.
8. The pharmaceutical composition of Clause 5, wherein the ligand-CNTFR complex subunit is gp130.
9. The pharmaceutical composition of Clause 8, wherein the mutation that reduces binding affinity for gp130 is at amino acid position 268, 269, or both, relative to a CNTFR polypeptide having the amino acid sequence set forth in SEQ ID NO:1.
10. The pharmaceutical composition of any one of Clauses 3 to 9, wherein the soluble CNTFR polypeptide comprises a solubility-conferring mutation in the domain that anchors wild-type CNTFR to a cell membrane.
11. The pharmaceutical composition of Clause 10, wherein the soluble CNTFR polypeptide comprises a truncation in the domain that anchors wild-type CNTFR to a cell membrane.
12. The pharmaceutical composition of Clause 10, wherein the soluble CNTFR polypeptide lacks the domain that anchors wild-type CNTFR to a cell membrane.
13. The pharmaceutical composition of one of Clauses 3 to 12, wherein the soluble CNTFR polypeptide comprises a mutation that increases binding affinity of the soluble CNTFR polypeptide for a CNTFR ligand relative to a wild-type CNTFR polypeptide.
14. The pharmaceutical composition of Clause 13, wherein the CNTFR ligand is selected from the group consisting of: ciliary neurotrophic factor (CNTF), cardiotrophin-like cytokine factor 1 (CLCF1), neuropoetin (NP), and any combination thereof.
15. The pharmaceutical composition of Clause 13, wherein the CNTFR ligand is CLCF1.
16. The pharmaceutical composition of Clause 15, wherein the mutation that increases binding affinity for CLCF1 is at amino acid position 110, 174, 237, 287, or any combination thereof, relative to a CNTFR polypeptide having the amino acid sequence set forth in SEQ ID NO:1.
17. The pharmaceutical composition of Clause 1 or Clause 2, wherein the agent is an antibody.
18. The pharmaceutical composition of any one of Clauses 1 to 17, wherein the agent is a polypeptide fused to a heterologous polypeptide.
19. The pharmaceutical composition of Clause 18, wherein the heterologous polypeptide is an Fc domain, an albumin, a transferrin, XTEN, a homo-amino acid polymer, a proline-alanine-serine polymer, an elastin-like peptide, or any combination thereof.
20. The pharmaceutical composition of Clause 19, wherein the heterologous polypeptide is an Fc domain.
21. The pharmaceutical composition of Clause 20, wherein the Fc domain is a human Fc domain.
22. The pharmaceutical composition of any one of Clauses 1 to 21, wherein the agent is conjugated to a moiety.
23. The pharmaceutical composition of Clause 22, wherein the moiety is polyethylene glycol (PEG), an anti-cancer drug, a detectable label, or any combination thereof.
24. A method, comprising:
administering to an individual in need thereof a therapeutically effective amount of the pharmaceutical composition of any one of Clauses 1 to 23 or the soluble CNTFR polypeptide of any one of Clauses 58 to 74, wherein binding of the agent to the ligand inhibits binding of the ligand to CNTFR.
25. The method according to Clause 24, wherein the individual in need thereof has a cell proliferative disorder associated with CNTFR signaling, and the administering is effective in treating the cell proliferative disorder.
26. The method according to Clause 24 or Clause 25, further comprising, prior to the administering, identifying the individual as having a cell proliferative disorder associated with CNTFR signaling.
27. The method according to Clause 26, wherein the identifying is based on CNTFR ligand abundance in a sample obtained from the individual.
28. The method according to Clause 27, wherein the abundance is of a CNTFR ligand selected from the group consisting of: CNTF, CLCF1, NP, and any combination thereof.
29. The method according to Clause 27 or Clause 28, wherein the CNTFR ligand abundance is quantified using a soluble CNTFR polypeptide as a CNTFR ligand capture agent.
30. The method according to Clause 29, wherein the soluble CNTFR polypeptide used as a CNTFR ligand capture agent is the soluble CNTFR polypeptide of any one of Clauses 58 to 74.
31. The method according to Clause 26, wherein the identifying is based on CNTFR abundance in a sample obtained from the individual.
32. The method according to Clause 26, wherein the identifying is based on the level of CNTFR signaling in a sample obtained from the individual.
33. The method according to Clause 32, wherein quantifying CNTFR signaling in the sample comprises quantifying the phosphorylation status of one or more CNTFR signaling pathway molecules.
34. The method according to any one of Clauses 27 to 33, wherein the identifying is based on an immunoassay.
35. The method according to any one of Clauses 27 to 33, wherein the identifying is based on nucleic acid sequencing.
36. The method according to any one of Clauses 27 to 35, wherein the sample is a tissue sample.
37. The method according to any one of Clauses 27 to 35, wherein the sample is a fluid sample.
38. The method according to any one of Clauses 27 to 37, further comprising obtaining the sample from the individual.

39. The method according to any one of Clauses 25 to 38, wherein the cell proliferative disorder is cancer.
40. The method according to Clause 39, wherein the cancer is lung cancer.
41. The method according to Clause 40, wherein the lung cancer is non-small cell lung cancer (NSCLC).
42. A method, comprising:
   identifying an individual as having a cell proliferative disorder associated with CNTFR signaling.
43. The method according to Clause 42, wherein the identifying is based on CNTFR ligand abundance in a sample obtained from the individual.
44. The method according to Clause 43, wherein the abundance is of a CNTFR ligand selected from the group consisting of: CNTF, CLCF1, NP, and any combination thereof.
45. The method according to Clause 42 or Clause 43, wherein the CNTFR ligand abundance is quantified using a soluble CNTFR polypeptide as a CNTFR ligand capture agent.
46. The method according to Clause 45, wherein the soluble CNTFR polypeptide used as a CNTFR ligand capture agent is the soluble CNTFR polypeptide of any one of Clauses 58 to 74.
47. The method according to Clause 42, wherein the identifying is based on CNTFR abundance in a sample obtained from the individual.
48. The method according to Clause 42, wherein the identifying is based on the level of CNTFR signaling in a sample obtained from the individual.
49. The method according to Clause 48, wherein the level of CNTFR signaling in the sample is determined based on the phosphorylation status of one or more CNTFR signaling pathway molecules.
50. The method according to any one of Clauses 42 to 49, wherein the identifying is based on an immunoassay.
51. The method according to any one of Clauses 42 to 49, wherein the identifying is based on nucleic acid sequencing.
52. The method according to any one of Clauses 42 to 51, wherein the sample is a tissue sample.
53. The method according to any one of Clauses 42 to 51, wherein the sample is a fluid sample.
54. The method according to any one of Clauses 43 to 53, further comprising obtaining the sample from the individual.
55. The method according to any one of Clauses 42 to 54, wherein the cell proliferative disorder is cancer.
56. The method according to Clause 55, wherein the cancer is lung cancer.
57. The method according to Clause 56, wherein the lung cancer is non-small cell lung cancer (NSCLC).
58. A soluble CNTFR polypeptide, comprising:
   a mutation that reduces binding affinity of the soluble CNTFR polypeptide for a ligand-CNTFR complex subunit relative to a wild-type CNTFR polypeptide,
   a mutation that increases binding affinity of the soluble CNTFR polypeptide for a CNTFR ligand relative to a wild-type CNTFR polypeptide, or
   both.
59. The soluble CNTFR polypeptide of Clause 58, wherein the soluble CNTFR polypeptide comprises a mutation that reduces binding affinity of the soluble CNTFR polypeptide for a ligand-CNTFR complex subunit relative to a wild-type CNTFR polypeptide, and wherein the ligand-CNTFR complex subunit is glycoprotein 130 (gp130), leukemia inhibitory factor receptor (LIFR), or both.
60. The soluble CNTFR polypeptide of Clause 59, wherein the ligand-CNTFR complex subunit is LIFR.
61. The soluble CNTFR polypeptide of Clause 60, wherein the mutation that reduces binding affinity for LIFR is at amino acid position 177, 178, or both, relative to a CNTFR polypeptide having the amino acid sequence set forth in SEQ ID NO:1.
62. The soluble CNTFR polypeptide of Clause 59, wherein the ligand-CNTFR complex subunit is gp130.
63. The soluble CNTFR polypeptide of Clause 62, wherein the mutation that reduces binding affinity for gp130 is at amino acid position 268, 269, or both, relative to a CNTFR polypeptide having the amino acid sequence set forth in SEQ ID NO:1.
64. The soluble CNTFR polypeptide of any one of Clauses 58 to 63, wherein the soluble CNTFR polypeptide comprises a solubility-conferring mutation in the domain that anchors wild-type CNTFR to a cell membrane.
65. The soluble CNTFR polypeptide of Clause 64, wherein the soluble CNTFR polypeptide comprises a truncation in the domain that anchors wild-type CNTFR to a cell membrane.
66. The soluble CNTFR polypeptide of Clause 64, wherein the soluble CNTFR polypeptide lacks the domain that anchors wild-type CNTFR to a cell membrane.
67. The soluble CNTFR polypeptide of one of Clauses 58 to 66, wherein the soluble CNTFR polypeptide comprises a mutation that increases binding affinity of the soluble CNTFR polypeptide for a CNTFR ligand relative to a wild-type CNTFR polypeptide.
68. The soluble CNTFR polypeptide of Clause 67, wherein the CNTFR ligand is selected from the group consisting of: ciliary neurotrophic factor (CNTF), cardiotrophin-like cytokine factor 1 (CLCF1), neuropoetin (NP), and any combination thereof.
69. The soluble CNTFR polypeptide of Clause 67, wherein the CNTFR ligand is CLCF1.
70. The soluble CNTFR polypeptide of Clause 69, wherein the mutation that increases binding affinity for CLCF1 is at amino acid position 110, 174, 237, 287, or any combination thereof, relative to a CNTFR polypeptide having the amino acid sequence set forth in SEQ ID NO:1.
71. The soluble CNTFR polypeptide of one of Clauses 58 to 70, wherein the soluble CNTFR polypeptide is fused to a heterologous polypeptide.
72. The soluble CNTFR polypeptide of Clause 71, wherein the heterologous polypeptide is an Fc domain, an albumin, a transferrin, XTEN, a homo-amino acid polymer, a proline-alanine-serine polymer, an elastin-like peptide, or any combination thereof.
73. The soluble CNTFR polypeptide of Clause 71, wherein the heterologous polypeptide is an Fc domain.
74. The soluble CNTFR polypeptide of Clause 73, wherein the Fc domain is a human Fc domain.
75. A nucleic acid that encodes the soluble CNTFR polypeptide of any one of Clauses 58 to 74.
76. An expression vector comprising the nucleic acid of Clause 75.
77. A host cell comprising the soluble CNTFR polypeptide of any one of Clauses 58 to 70, the nucleic acid of Clause 75, the expression vector of Clause 76, or any combination thereof.
78. The host cell of Clause 77, wherein the host cell is a prokaryotic cell.
79. The host cell of Clause 77, wherein the host cell is a eukaryotic cell.
80. The host cell of Clause 79, wherein the eukaryotic cell is a mammalian cell.

81. The host cell of Clause 80, wherein the mammalian cell is a human cell.
82. A nucleic acid that encodes a CNTFR polypeptide fused to a cell surface display protein.
83. The nucleic acid of Clause 82, wherein the CNTFR polypeptide comprises one or more mutations relative to a CNTFR polypeptide having the amino acid sequence set forth in SEQ ID NO:1.
84. The nucleic acid of Clause 83, wherein the cell surface display protein is selected from the group consisting of: a bacterial surface display protein, a phage display protein, and a yeast display protein.
85. The nucleic acid of Clause 84, wherein the cell surface display protein is a yeast display protein.
86. The nucleic acid of Clause 85, wherein the yeast display protein is Aga2p.
87. An expression vector comprising the nucleic acid of any one of Clauses 82 to 86.
88. A host cell comprising the nucleic acid of any one of Clauses 82 to 86, or the expression vector of Clause 87.
89. A CNTFR polypeptide encoded by the nucleic acid of any one of Clauses 82 to 86, or the expression vector of Clause 87.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A soluble ciliary neurotrophic factor receptor (CNTFR) polypeptide comprising a CNTFR extracellular domain that specifically binds cardiotrophin-like cytokine factor 1 (CLCF1), wherein the extracellular domain comprises:
one or more mutations that reduce binding affinity of the soluble CNTFR polypeptide for leukemia inhibitory factor receptor (LIFR) relative to a wild-type CNTFR polypeptide;
one or more mutations that increase binding affinity of the soluble CNTFR polypeptide for CLCF1 relative to a wild-type CNTFR polypeptide; or both.

2. The soluble CNTFR polypeptide of claim 1, wherein the extracellular domain comprises:
one or more mutations that reduce binding affinity of the soluble CNTFR polypeptide for LIFR relative to a wild-type CNTFR polypeptide, wherein the one or more mutations comprise a mutation at amino acid position 177, 178, or both, relative to a CNTFR polypeptide having the amino acid sequence set forth in SEQ ID NO:1;
one or more mutations that increase binding affinity of the soluble CNTFR polypeptide for CLCF1 relative to a wild-type CNTFR polypeptide, wherein the one or more mutations comprise a mutation at amino acid position 110, 174, 237, 287, or any combination thereof, relative to a CNTFR polypeptide having the amino acid sequence set forth in SEQ ID NO:1; or both.

3. The soluble CNTFR polypeptide of claim 2, wherein the one or more mutations that reduce binding affinity of the soluble CNTFR polypeptide for LIFR comprise Y177H, K178N, or both.

4. The soluble CNTFR polypeptide of claim 2, wherein the one or more mutations that increase binding affinity of the soluble CNTFR polypeptide for CLCF1 comprise R110Q, T174P, S237F, I287F, or any combination thereof.

5. The soluble CNTFR polypeptide of claim 1, wherein the soluble CNTFR polypeptide comprises one or more mutations that reduce binding affinity of the soluble CNTFR polypeptide for glycoprotein 130 (gp130) relative to a wild-type CNTFR polypeptide.

6. The soluble CNTFR polypeptide of claim 5, wherein the one or more mutations that reduce binding affinity of the soluble CNTFR polypeptide for gp130 comprise a mutation at amino acid position 268, 269, or both, relative to a CNTFR polypeptide having the amino acid sequence set forth in SEQ ID NO:1.

7. The soluble CNTFR polypeptide of claim 6, wherein the one or more mutations that reduce binding affinity for gp130 comprise T268A, D269A, or both.

8. The soluble CNTFR polypeptide of claim 1, wherein the soluble CNTFR polypeptide is fused to a heterologous polypeptide.

9. The soluble CNTFR polypeptide of claim 8, wherein the heterologous polypeptide is an Fc domain.

10. The soluble CNTFR polypeptide of claim 9, wherein the Fc domain is a human Fc domain.

11. The soluble CNTFR polypeptide of claim 1, wherein the soluble CNTFR polypeptide is conjugated to a moiety, optionally wherein the moiety is polyethylene glycol (PEG), an anti-cancer drug, or a detectable label.

12. A pharmaceutical composition comprising the soluble CNTFR polypeptide of claim 1 and a pharmaceutically acceptable carrier.

13. A method, comprising:
   administering to an individual in need thereof a therapeutically effective amount of the pharmaceutical composition of claim 12, wherein binding of the soluble CNTFR polypeptide to CLCF1 inhibits binding of CLCF1 to CNTFR.

14. The method according to claim 13, wherein the individual in need thereof has a disorder associated with CNTFR signaling, and the administering is effective in treating the disorder.

15. The method according to claim 14, wherein the disorder is cancer.

16. The method according to claim 15, wherein the cancer is lung cancer.

17. The method according to claim 16, wherein the lung cancer is non-small cell lung cancer (NSCLC).

18. A nucleic acid that encodes a soluble ciliary neurotrophic factor receptor (CNTFR) polypeptide comprising a CNTFR extracellular domain that specifically binds cardiotrophin-like cytokine factor 1 (CLCF1), wherein the extracellular domain comprises:
   one or more mutations that reduce binding affinity of the soluble CNTFR polypeptide for leukemia inhibitory factor receptor (LIFR) relative to a wild-type CNTFR polypeptide;
   one or more mutations that increase binding affinity of the soluble CNTFR polypeptide for CLCF1 relative to a wild-type CNTFR polypeptide; or both.

19. An expression vector comprising the nucleic acid of claim 18.

20. A host cell comprising the nucleic acid of claim 18, optionally wherein the nucleic acid is present in an expression vector.

* * * * *